(12) United States Patent
Savall et al.

(10) Patent No.: US 10,568,704 B2
(45) Date of Patent: Feb. 25, 2020

(54) USER CONSOLE SYSTEM FOR ROBOTIC SURGERY

(71) Applicant: Verb Surgical Inc., Mountain View, CA (US)

(72) Inventors: Joan Savall, Palo Alto, CA (US); Pablo E. Garcia Kilroy, Menlo Park, CA (US); Brent Nobles, Palo Alto, CA (US); David Moore, Sausalito, CA (US)

(73) Assignee: VERB SURGICAL INC., Mountain View, CA (US)

( * ) Notice: Subject to any disclaimer, the term of this patent is extended or adjusted under 35 U.S.C. 154(b) by 204 days.

(21) Appl. No.: 15/712,052

(22) Filed: Sep. 21, 2017

(65) Prior Publication Data

US 2018/0078034 A1 Mar. 22, 2018

Related U.S. Application Data

(60) Provisional application No. 62/397,823, filed on Sep. 21, 2016.

(51) Int. Cl.
*A61B 34/00* (2016.01)
*A61B 90/60* (2016.01)
(Continued)

(52) U.S. Cl.
CPC .............. *A61B 34/25* (2016.02); *A47B 21/02* (2013.01); *A47B 21/03* (2013.01); *A47B 21/04* (2013.01);
(Continued)

(58) Field of Classification Search
CPC .................. A61B 34/25; A61B 90/60; A61B 2017/00199; A61B 90/37; A61B 50/10;
(Continued)

(56) References Cited

U.S. PATENT DOCUMENTS 9,079,089 B2 * 7/2015 Lokken ..................... A61G 5/14
9,474,580 B2 * 10/2016 Hannaford ............. A61B 90/60
(Continued)

FOREIGN PATENT DOCUMENTS

WO 2018/057814 A1 3/2018

OTHER PUBLICATIONS

Australian Full Examination Report dated Apr. 26, 2019 for related Australian Appln. No. 2017330370 3 Pages.
(Continued)

*Primary Examiner* — Milton Nelson, Jr.
(74) *Attorney, Agent, or Firm* — Womble Bond Dickinson (US) LLP

(57) ABSTRACT

A user console for controlling a remote surgical robotic instrument may include an adjustable ergonomic seat assembly comprising a seat pan, where the seat assembly is configurable between a seated configuration and an elevated configuration, and where the seat pan has a higher anteverted position in the elevated configuration than in the seated configuration. The user console may further include a display configured to receive real time surgical information, and one or more controls for remotely controlling the robotic instrument. The display and/or the one or more controls may have multiple positions and change position automatically according to a seating profile associated with at least one user.

29 Claims, 45 Drawing Sheets

(51) Int. Cl.
| | |
|---|---|
| *B25J 13/02* | (2006.01) |
| *A61B 34/30* | (2016.01) |
| *A47C 7/54* | (2006.01) |
| *B25J 13/06* | (2006.01) |
| *B25J 13/08* | (2006.01) |
| *A47B 21/02* | (2006.01) |
| *A47B 21/03* | (2006.01) |
| *A47B 21/04* | (2006.01) |
| *A61B 17/00* | (2006.01) |

(52) U.S. Cl.
CPC .............. *A47C 7/543* (2013.01); *A61B 34/30* (2016.02); *A61B 34/74* (2016.02); *A61B 90/60* (2016.02); *B25J 13/02* (2013.01); *B25J 13/06* (2013.01); *B25J 13/088* (2013.01); *A47B 2021/0392* (2013.01); *A61B 2017/00199* (2013.01); *A61B 2017/00973* (2013.01)

(58) Field of Classification Search
CPC .......... A61B 2017/00212; A61B 34/74; A61B 34/30; A61B 34/35; A61B 2017/00973; A47B 2021/0392; A47B 21/04; A47B 21/03; A47B 21/02; B25J 13/06; B25J 13/02; A47C 7/543
USPC ................................................ 297/313, 217.4
See application file for complete search history.

(56) References Cited

U.S. PATENT DOCUMENTS

| | | | |
|---|---|---|---|
| 2004/0111183 A1* | 6/2004 | Sutherland | A61B 90/25 700/245 |
| 2008/0125794 A1* | 5/2008 | Brock | B25J 3/04 606/130 |
| 2010/0217991 A1* | 8/2010 | Choi | B25J 9/1689 713/176 |
| 2010/0225209 A1 | 9/2010 | Goldberg et al. | |
| 2011/0118748 A1 | 5/2011 | Itkowitz | |
| 2014/0121834 A1 | 5/2014 | Ogawa et al. | |
| 2014/0243849 A1 | 8/2014 | Saglam et al. | |
| 2015/0066051 A1 | 3/2015 | Kwon et al. | |
| 2015/0248847 A1 | 9/2015 | Wang et al. | |
| 2018/0078319 A1 | 3/2018 | Nobles et al. | |
| 2018/0214226 A1* | 8/2018 | Kan | B25J 17/02 |

OTHER PUBLICATIONS

Written Opinion of the International Search Authority dated Dec. 14, 2017 for WO Application No. PCT/US17/052824.
Outgoing—ISA/210—International Search Report dated Dec. 14, 2017 for WO Application No. PCT/US17/052824.
CNET. "This Could Be the Desk of the Future." YouTube, YouTube, Jul. 20, 2016. 0:10, 1:19, 0:52-1 :00.www.youtube.com/watchy=UaNf50BAI8U.

\* cited by examiner

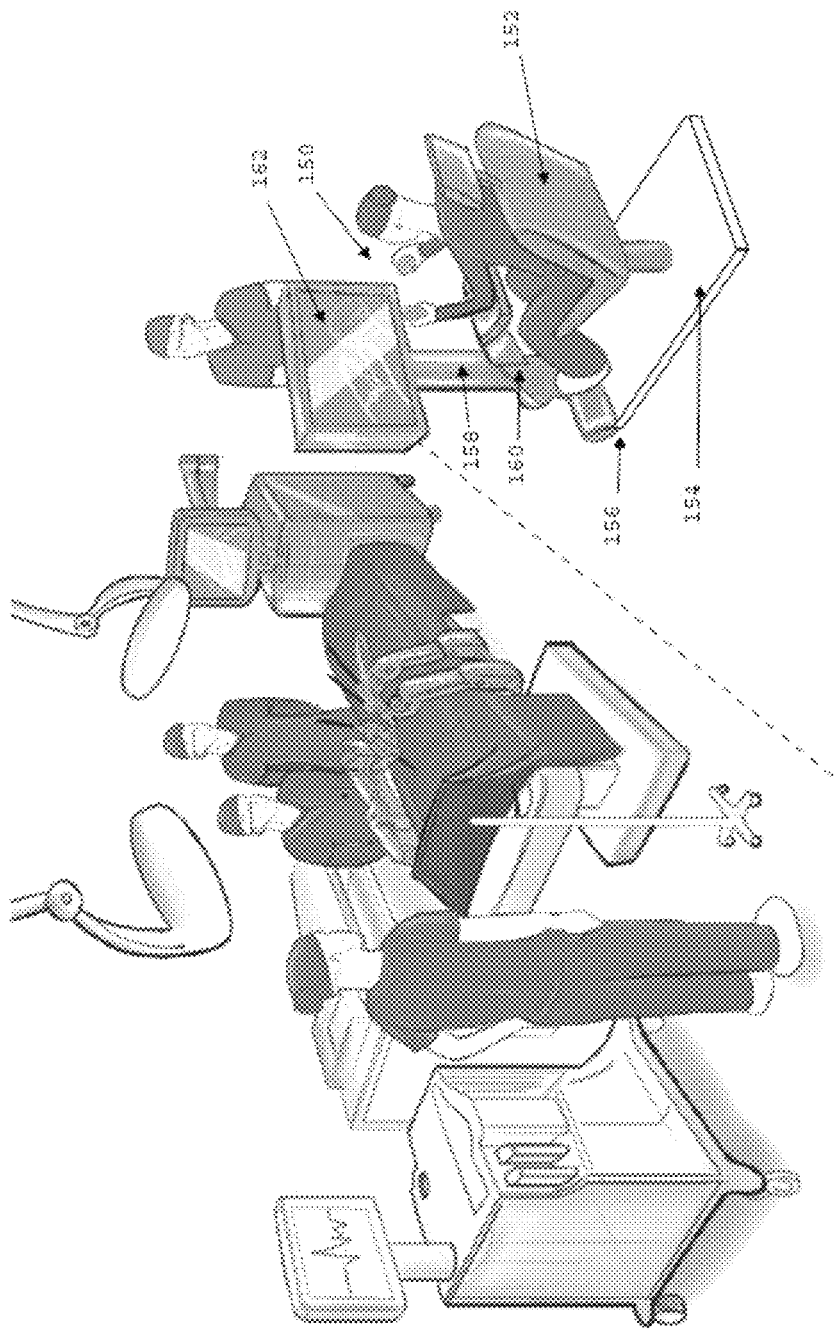

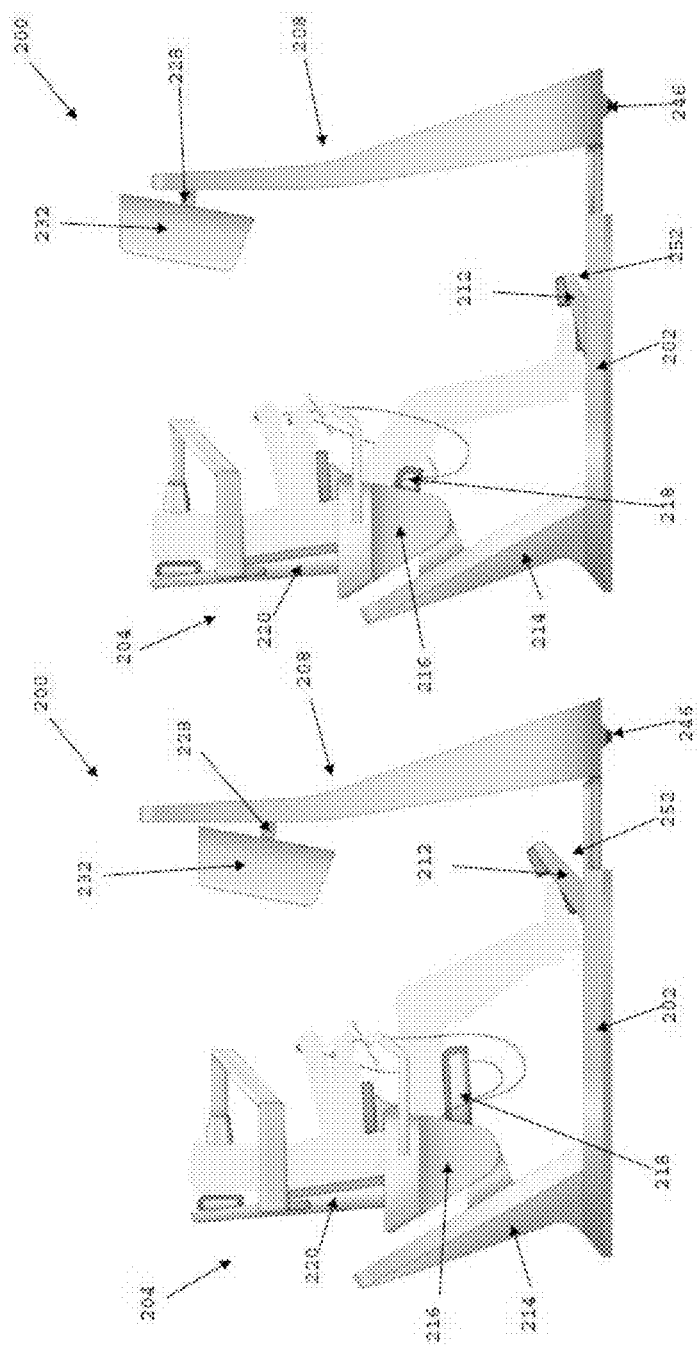

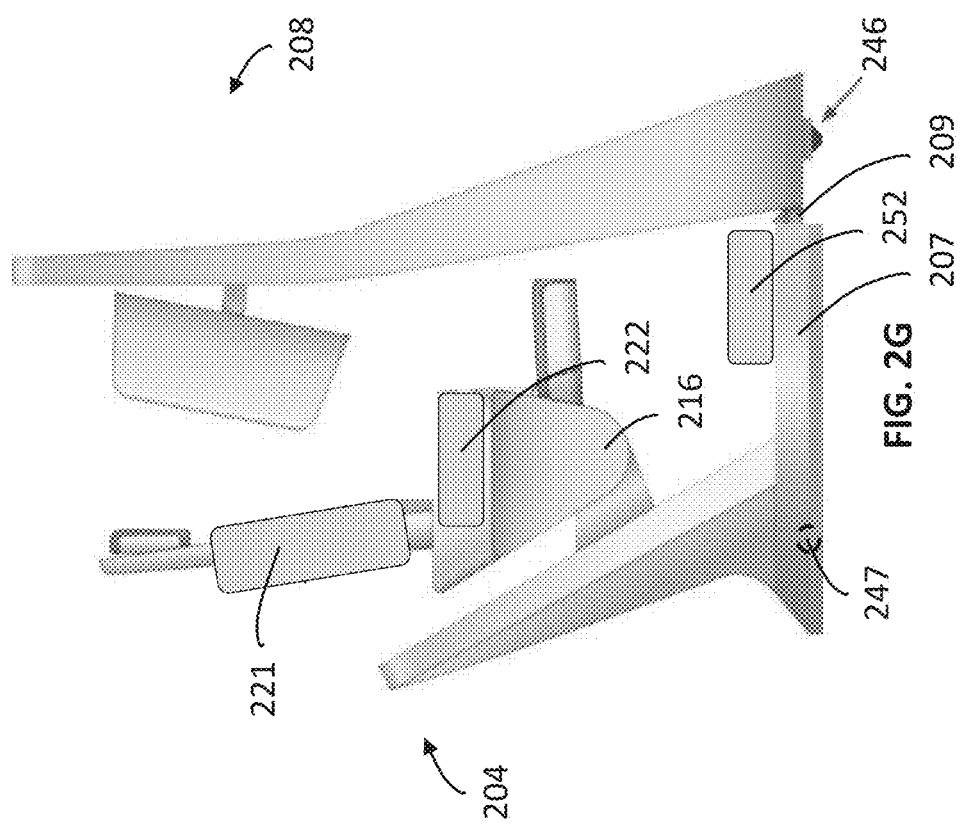

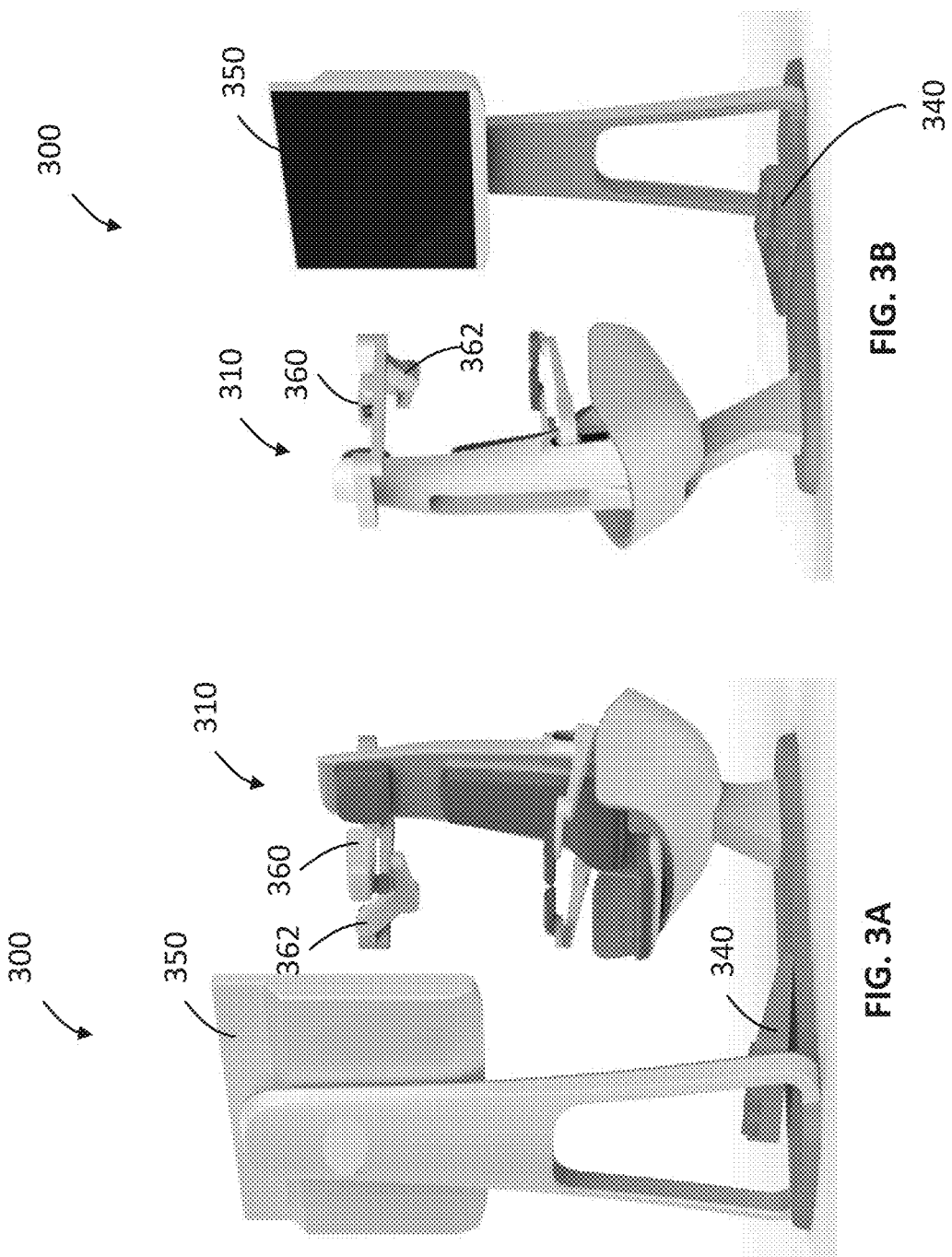

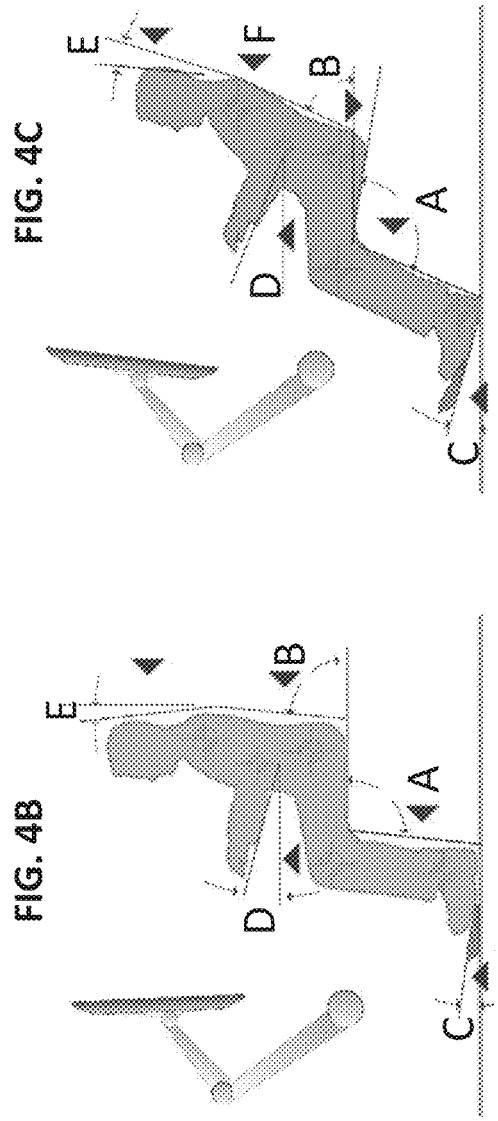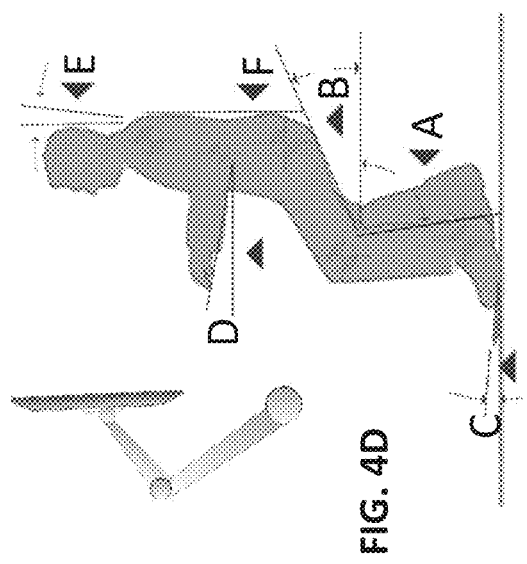

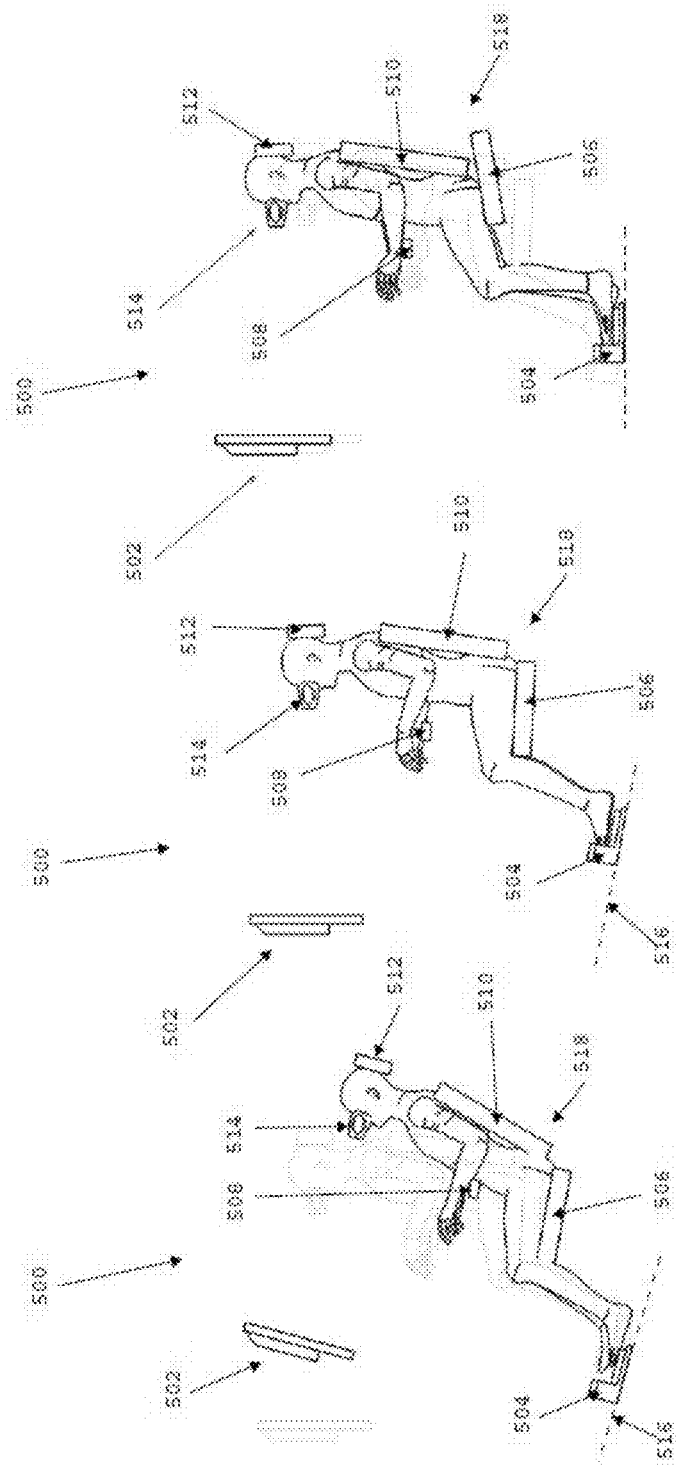

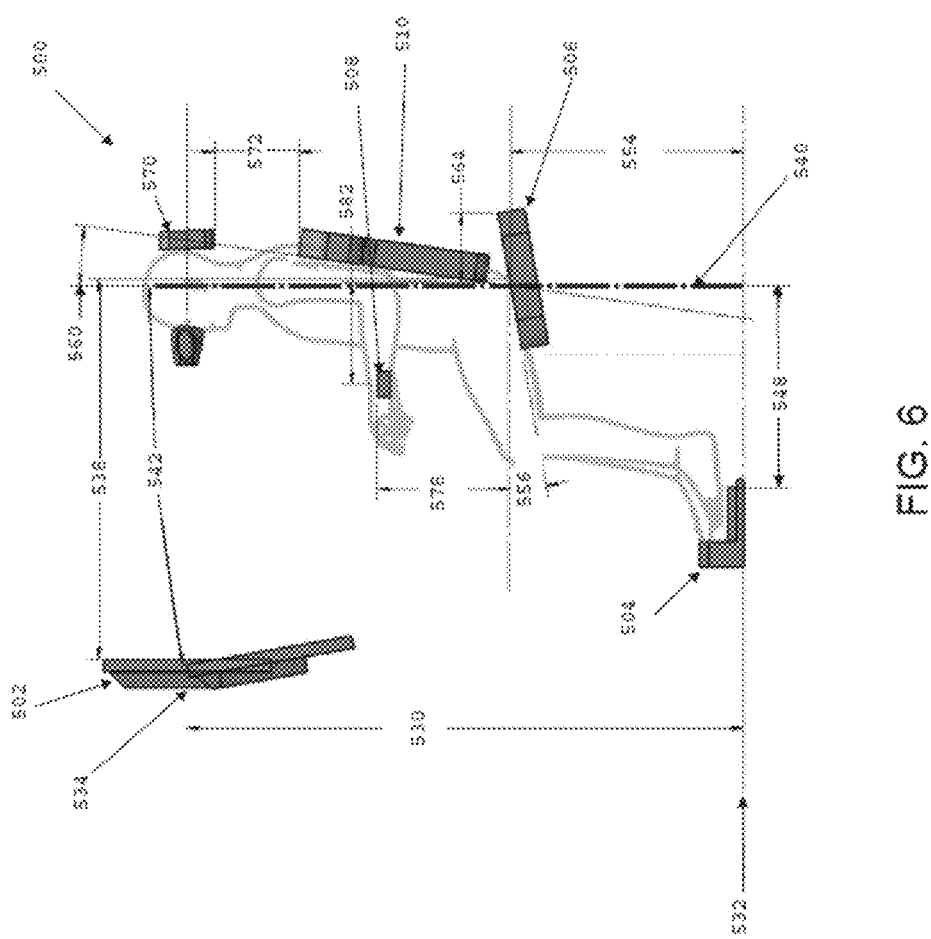

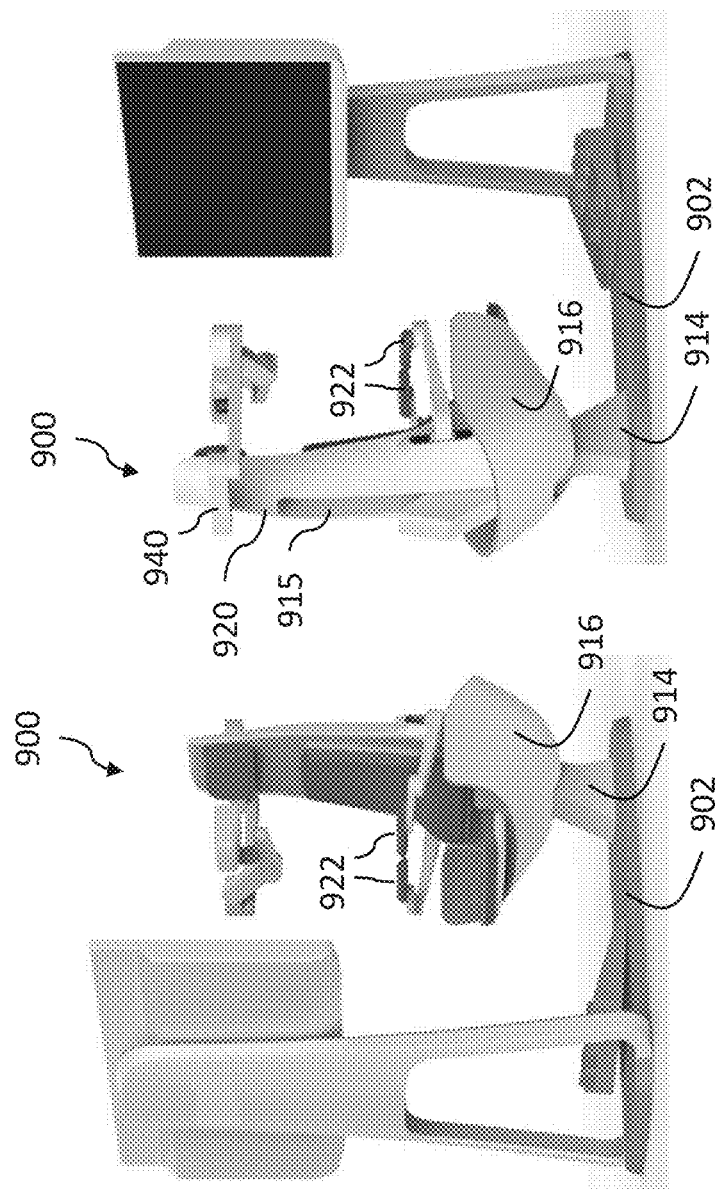

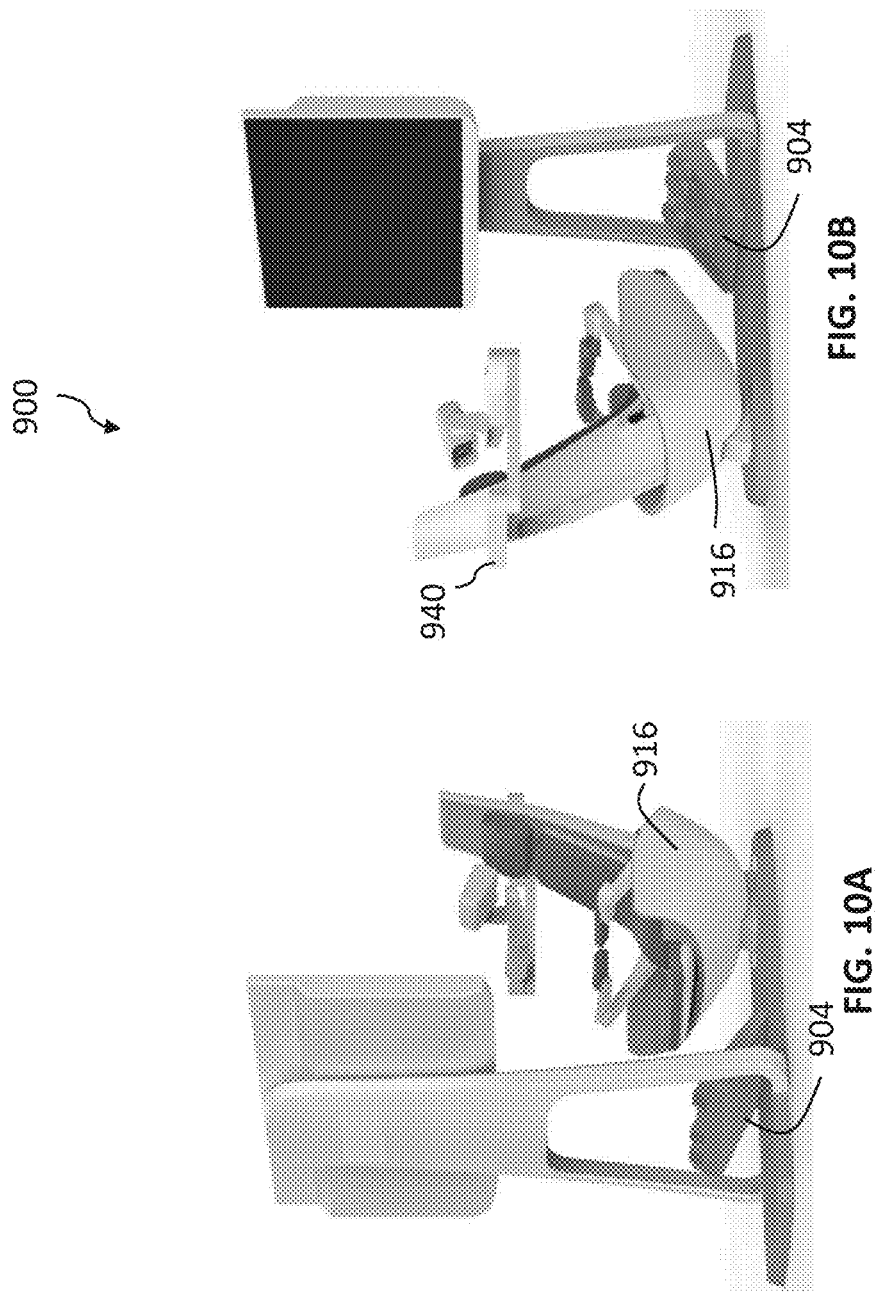

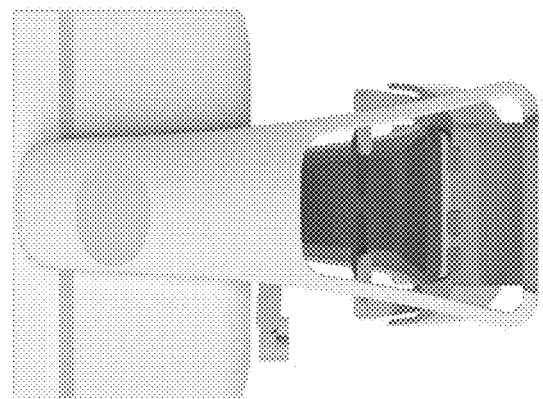
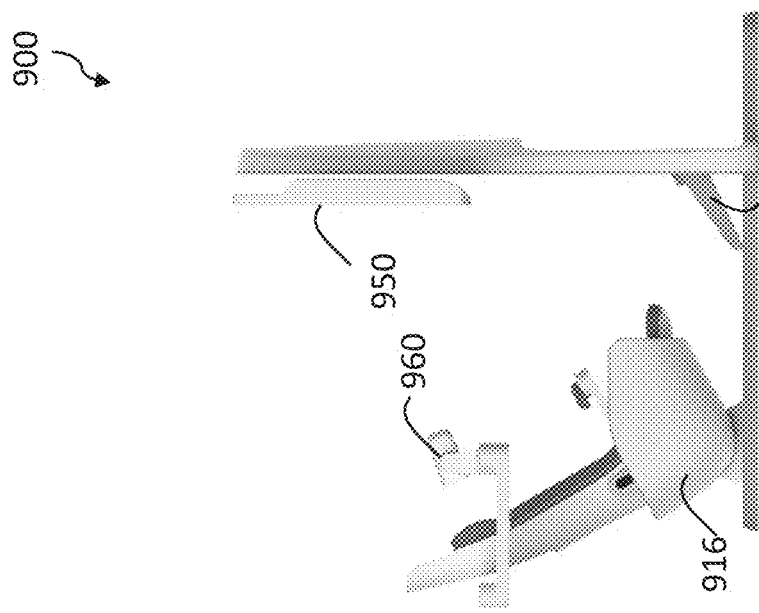
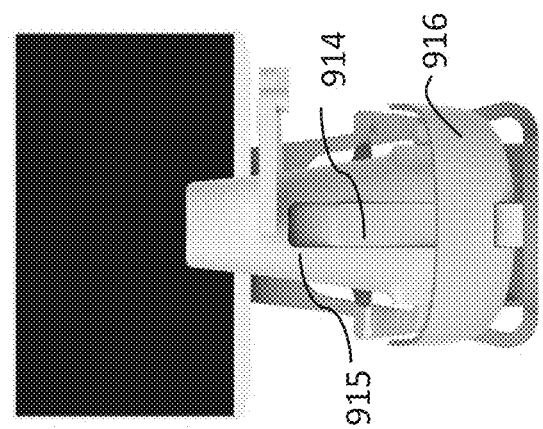

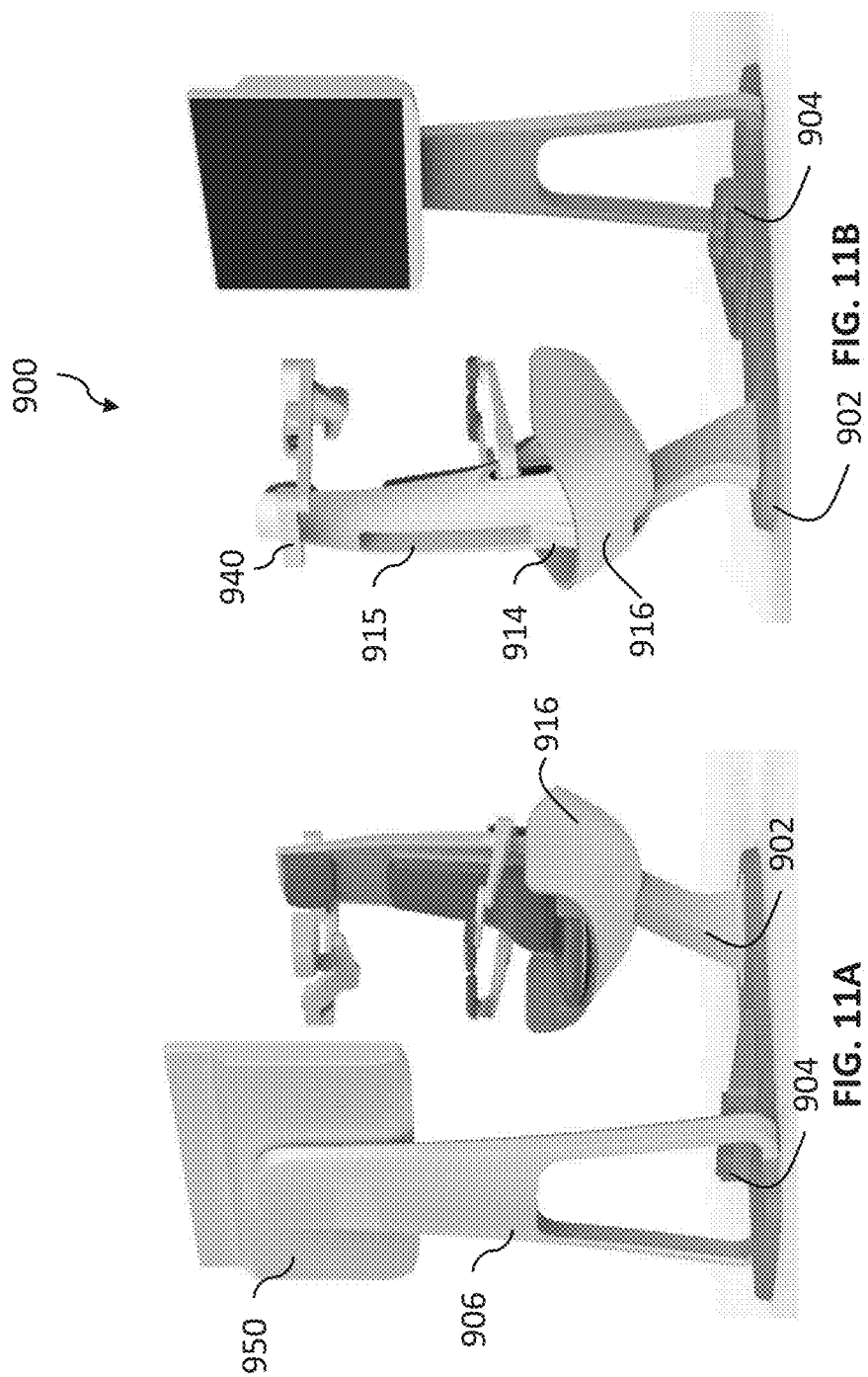

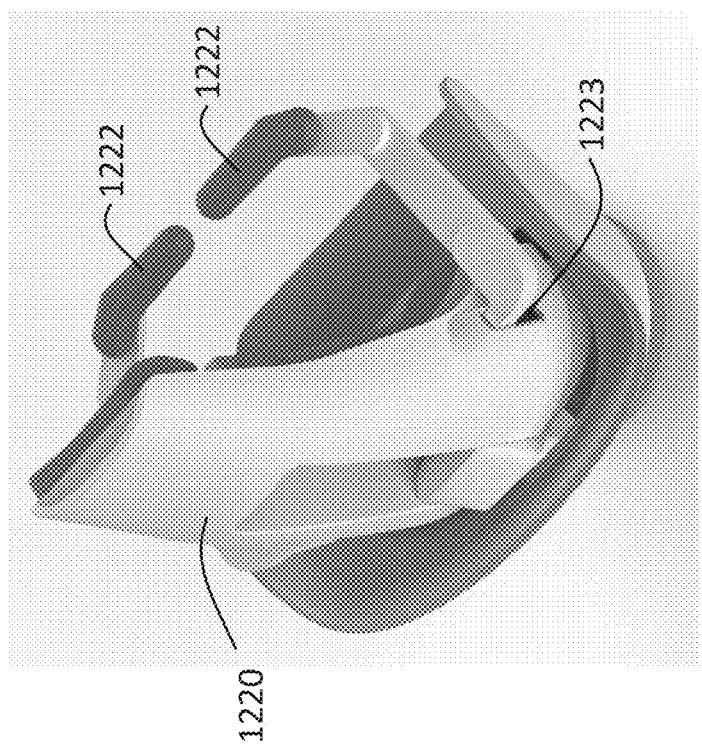

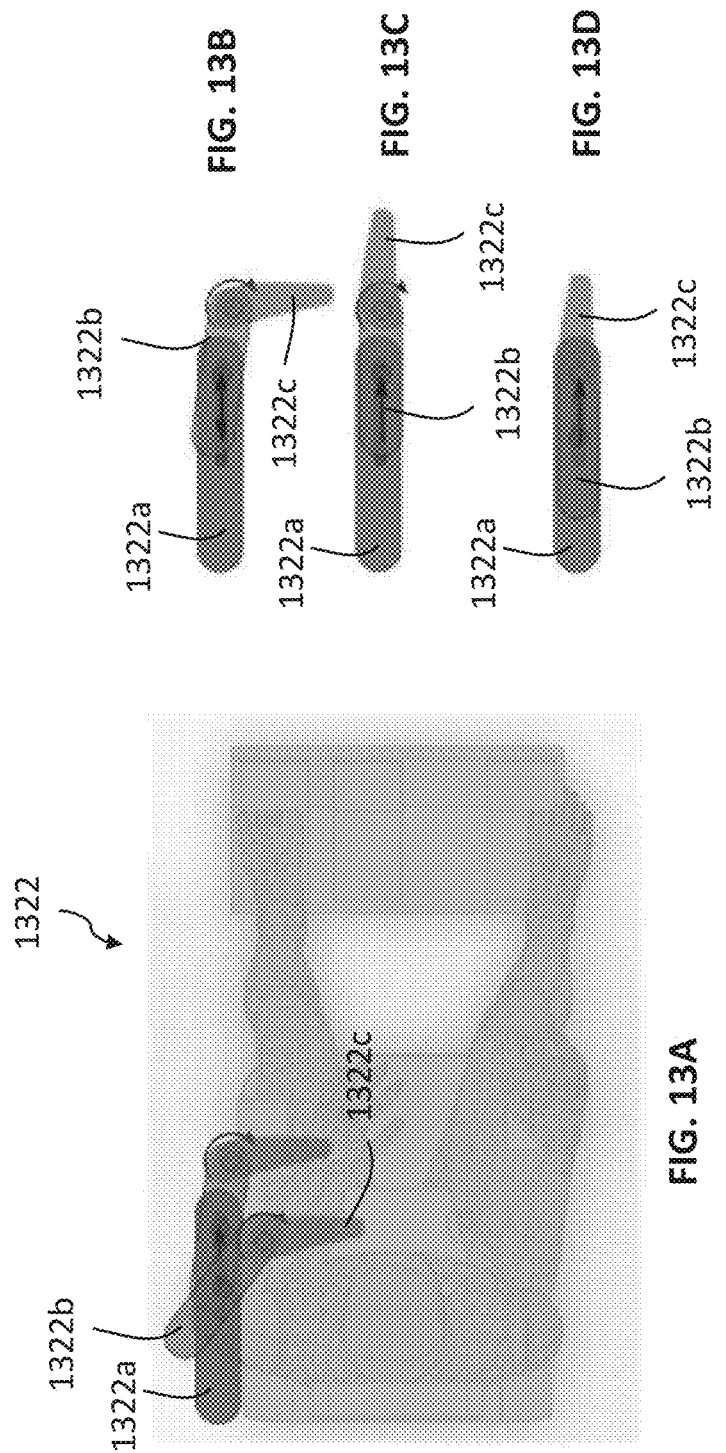

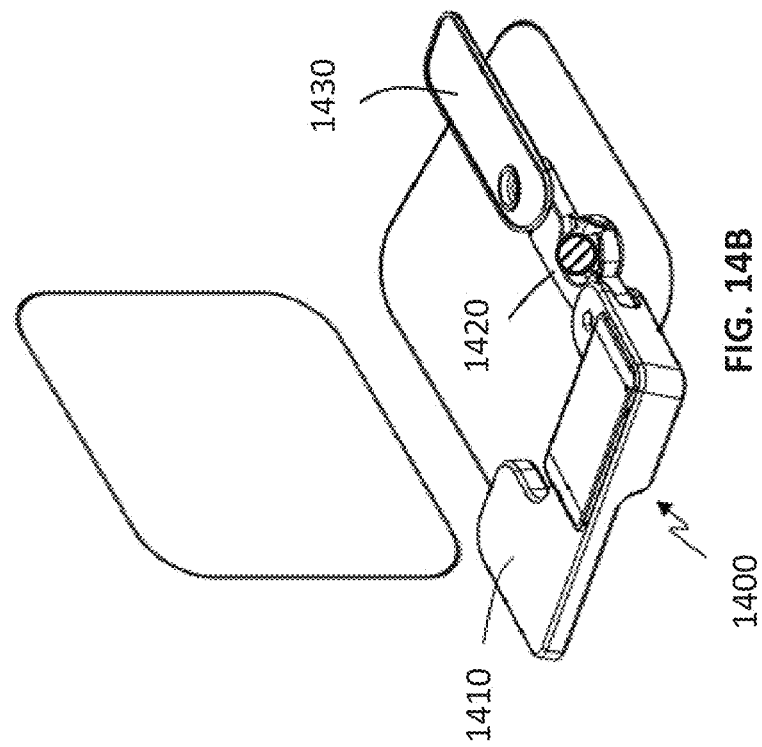
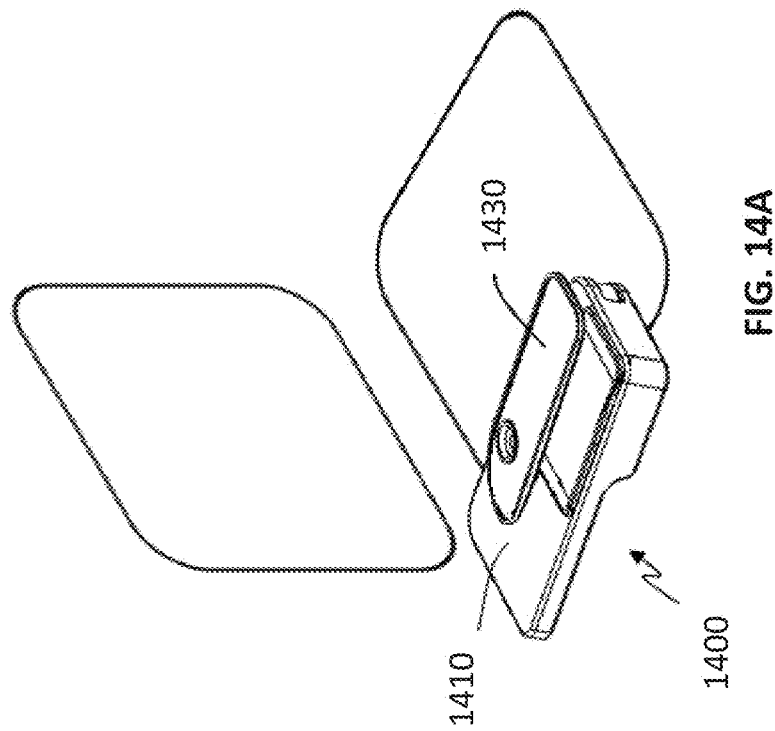

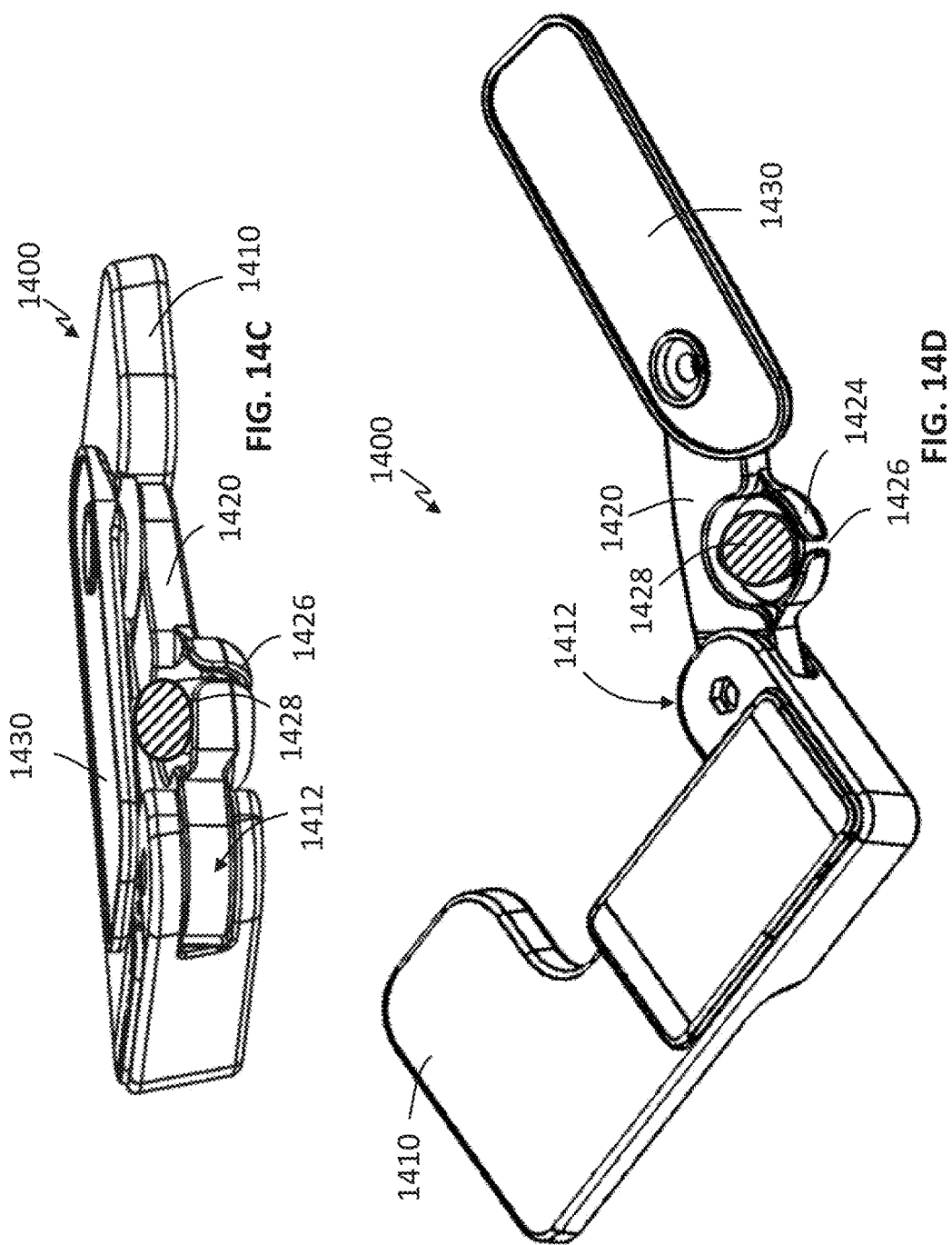

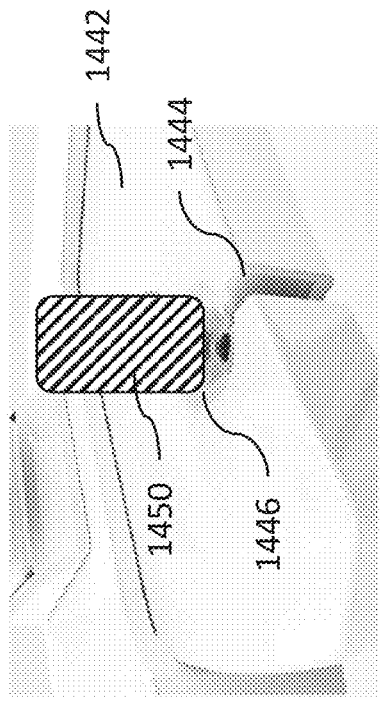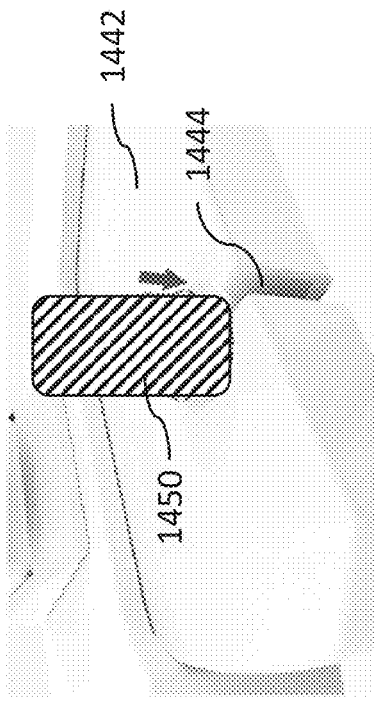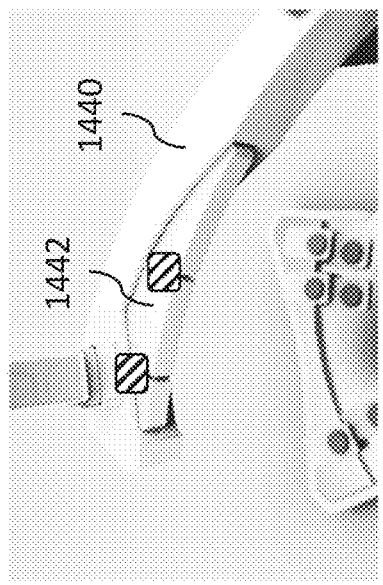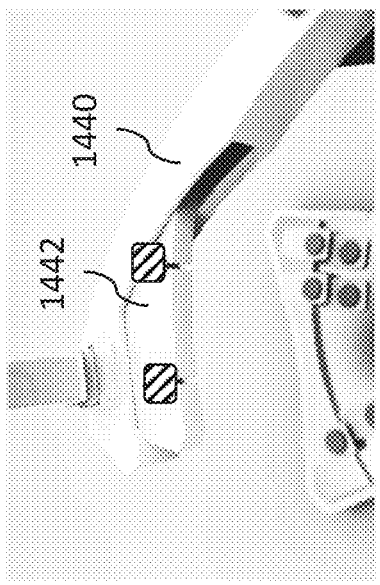

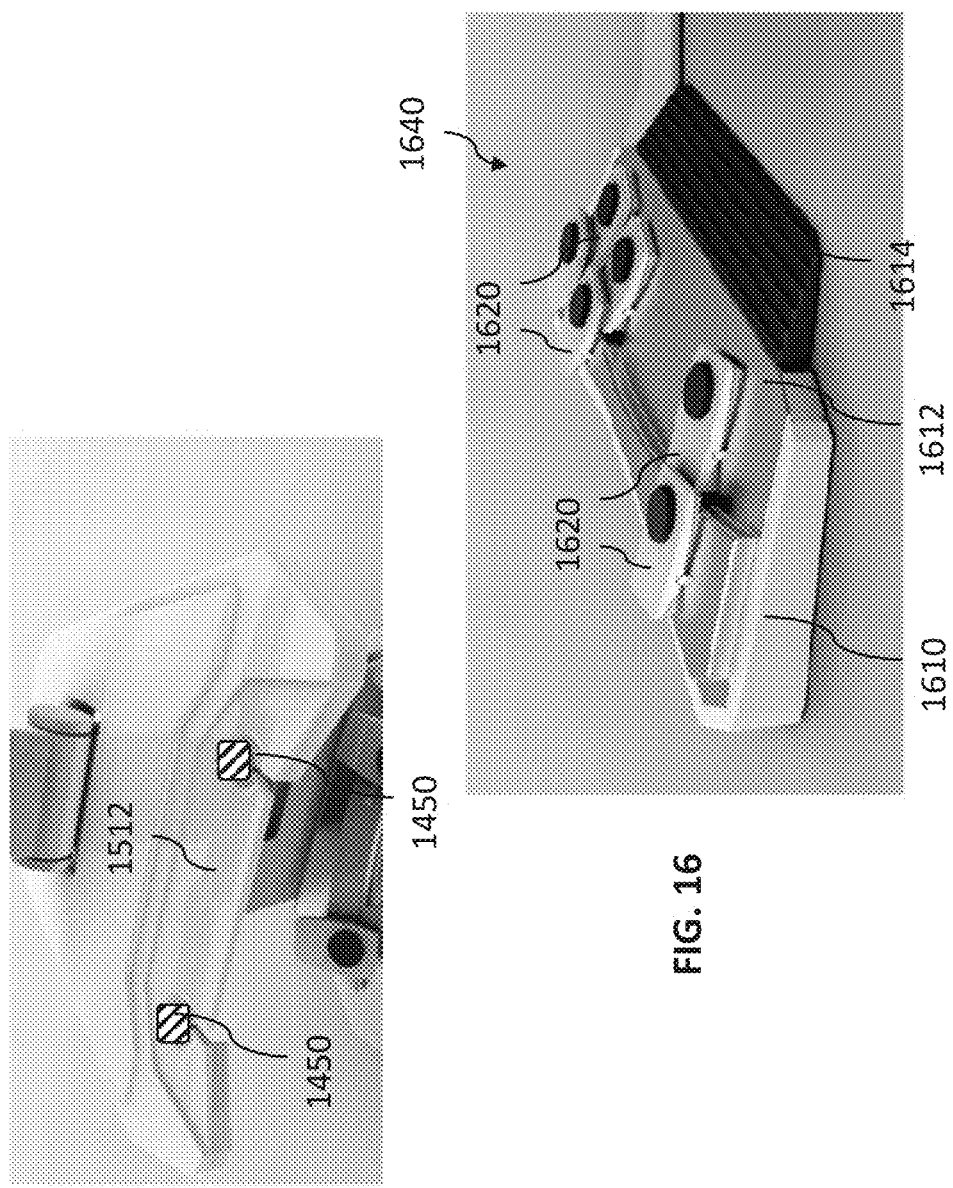

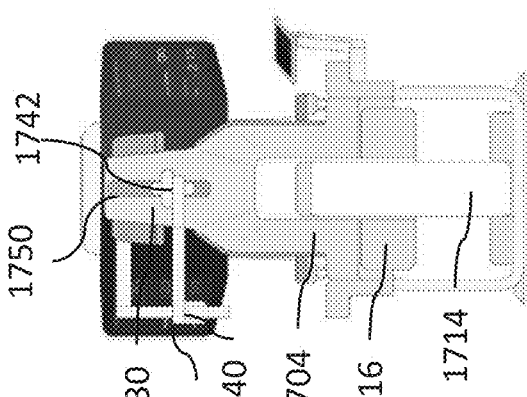
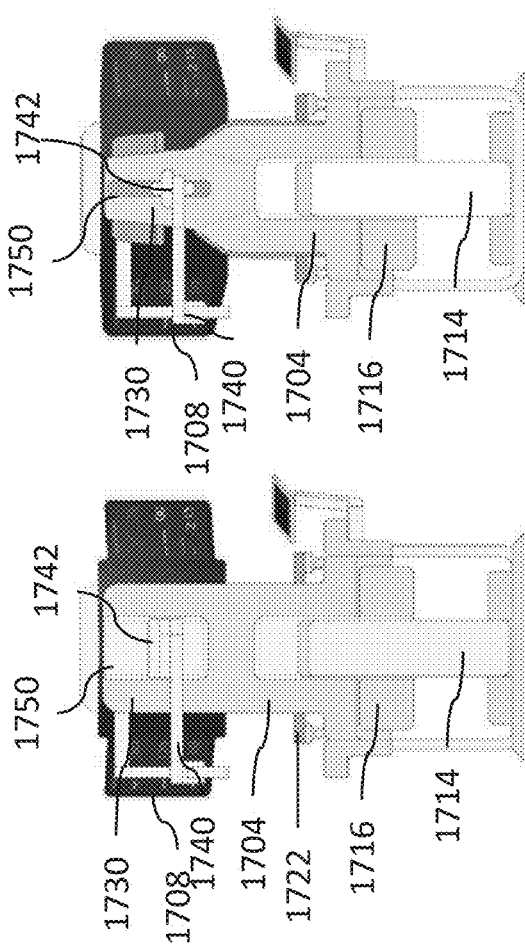
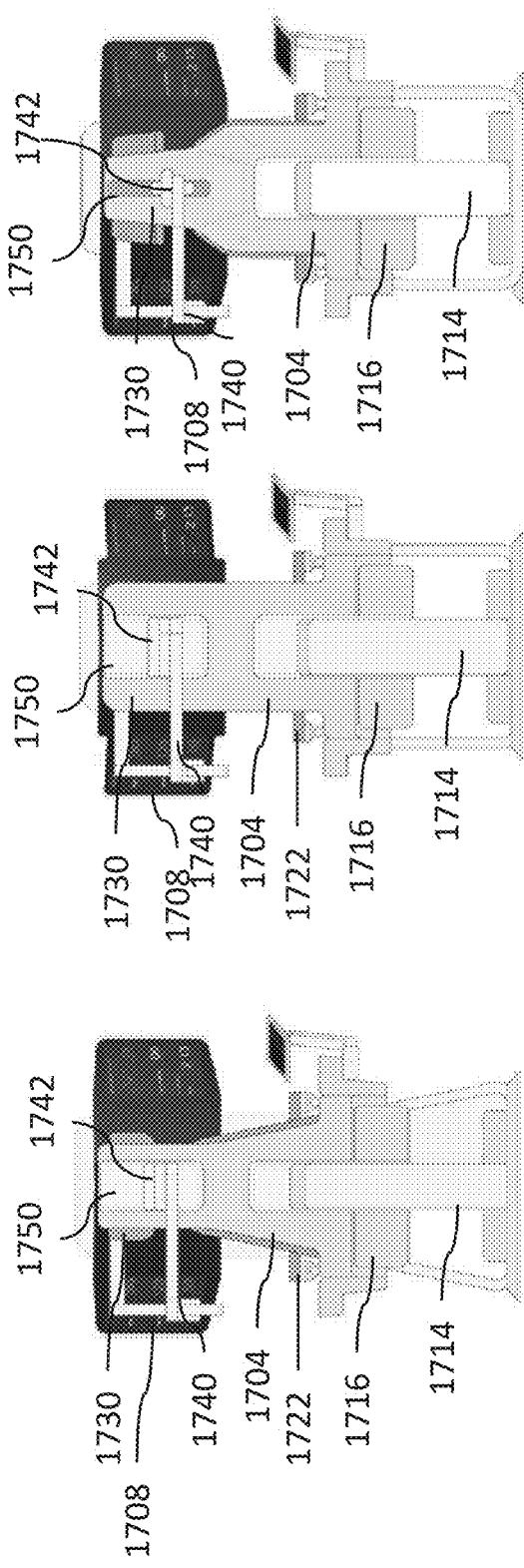
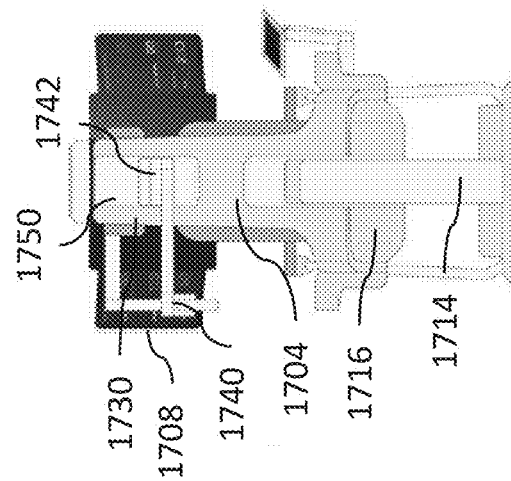
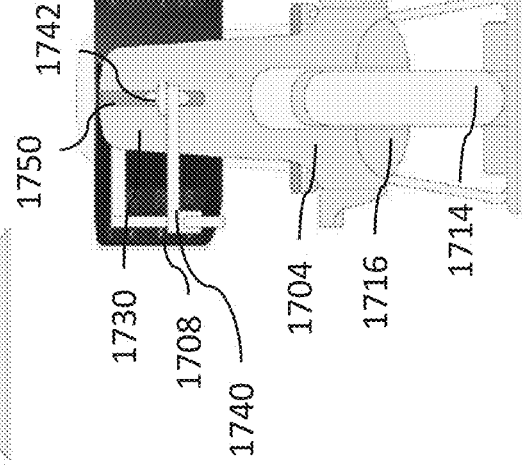

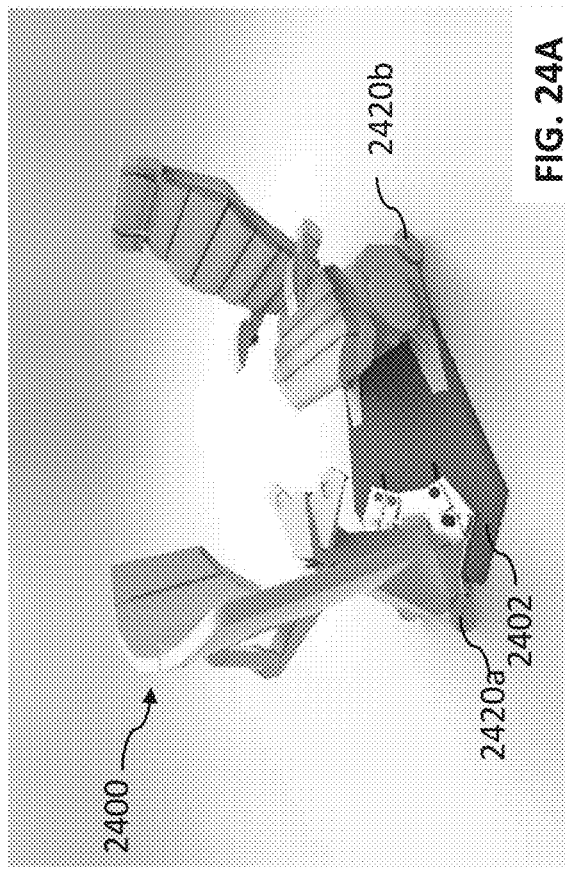
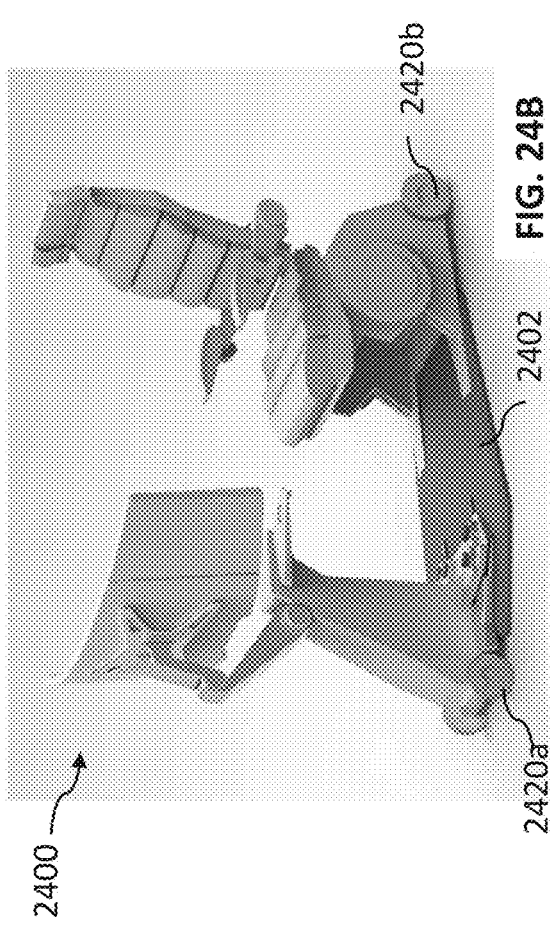

USER CONSOLE SYSTEM FOR ROBOTIC SURGERY

CROSS-REFERENCE TO RELATED APPLICATIONS

This application claims priority to U.S. patent application Ser. No. 62/397,823, filed on Sep. 21, 2016, which is incorporated herein in its entirety by this reference.

TECHNICAL FIELD

This invention relates generally to the field of robotic surgery and more specifically to user console system

BACKGROUND

Computer-assisted and robotic surgery systems allow healthcare practitioners to achieve greater accuracy, automation and/or less-invasive approaches while performing a variety of diagnostic and/or therapeutic procedures. Such technologies are broadly applicable to a variety of medical specialties, ranging from ophthalmology and anesthesiology, to orthopedics and interventional radiology. Some computer-assisted systems provide image-guided navigation to improve the accuracy of invasive procedures, while other systems incorporate sophisticated robotics and visualization technology for performing minimally invasive surgeries that can lead to reduced scarring and shorter recovery times. One example of a minimally invasive surgery is a laparoscopic procedure, which typically involves creating a number of small incisions in the patient (e.g., in the abdomen), and introducing one or more tools and at least one camera through the incisions into the patient. The surgical procedure is then performed by using the introduced tools, with the visualization aid provided by the camera. In robotic or robotic-assisted surgery, at least some of the introduced instruments may be attached to one or more robotic arms operated remotely (e.g., in tele-operation) by a user (e.g., surgeon). Thus, it is desirable to have a user console system through which a user may control the introduced tools and/or camera used in robotic surgery.

SUMMARY

Generally, a user console for controlling a remote surgical robotic instrument may include an adjustable ergonomic seat assembly comprising a seat pan, a display configured to receive real time surgical information, and one or more controls for remotely controlling the robotic instrument. The display may include, for example, an open display (e.g., a monitor mounted on stand) and/or an immersive display. The display or the one or more controls may have multiple positions, and change position automatically according to a seating profile associated with at least one user. For example, the display or the one or more controls may position automatically according to any of a plurality of seating profiles associated with a plurality of users. In some variations, the display and/or the one or more controls may additionally or alternatively change position automatically according to a surgical procedure type, and/or their positions may be manually adjustable.

In some variations, the user console may have multiple configurations, such as a seated configuration, an elevated configuration, and a reclined configuration. Various aspects of the display, the seat assembly (e.g., seat pan, seat back, headrest coupled to the seat back), and/or the one or more controls may be positioned differently for different configurations. For example, the display and/or the one or more controls may be in a higher position when the seat assembly is in the elevated configuration than when the seat assembly is in the seated configuration. As another example, the seat pan may have a higher anteverted position in the elevated configuration than in the seated configuration. The seat back may have multiple angular positions relative to the seat pan, and in some variations a posterior end of the seat pan may be more posterior than a lower end of the seat back when the seat assembly is in the elevated configuration than when the seat assembly is in the seated configuration.

The one or more controls for remotely controlling the robotic instrument may include, for example, a handheld user interface device. In some variations, the user console may include a docking station configured to releasably hold the handheld user interface. As another example, the one or more controls for remotely controlling the robotic instrument may include a foot-operated control, such as a foot pedal assembly. In some variations, the foot pedal assembly may be configured to adjustably tilt posteriorly.

In some variations, the user console may include a base, where the foot pedal assembly and the seat assembly are mounted on the base and may be adjusted relative to the base. For example, the foot pedal assembly and/or the seat assembly may be configured to translate along the base.

The user console may, in some variations, include one or more armrests coupled to the seat assembly. The armrest may have multiple positions and change position automatically according to the seating profile associated with at least one user. For example, the armrest may have a more superior position relative to the seat pan when the seat assembly is in the elevated configuration than when the seat assembly is in the seated configuration.

A control panel may be provided on or near the one or more armrests, or in any suitable location on or near the user console. The control panel may receive user information. User information from the control panel or another suitable interface may, for example, be used to identify the user in the user console and obtain user console settings from a seating profile associated with the user. As another example, the user may enter user characteristics, such as anthropometric data, through the control panel (or other suitable interface, such that a seating profile for the user may be generated automatically based at least in part on the entered anthropometric data.

In some variations, the user console may include a console controller configured to detect the presence or absence of a user in the user console. For example, the console controller may detect the presence or absence of a user based on an eye-tracking algorithm, and/or based on at least one sensor (e.g., pressure sensor) in the user console. The information relating to the presence or absence of a user in the user console may, in some variations, be used a safety interlock, such that the one or more controls is disabled in response to the console controller detecting the absence of a user.

BRIEF DESCRIPTION OF THE DRAWINGS

FIGS. 1A and 1B depict examples of an operating room arrangement with a surgical robotic system, with and without an integrated seat.

FIGS. 2E and 2F are side orthogonal views of the user console in FIGS. 2A to 2C, in a seated and an elevated configuration, respectively. FIG. 2G is a side orthogonal view of the user console in FIGS. 2A-2F in a collapsed or retracted configuration.

FIGS. 3A and 3B are front perspective and rear perspective views of an exemplary user console.

FIGS. 4B, 4C, and 4D are schematics illustrating points of adjustability for a seated configuration, a reclined configuration, and an elevated configuration, respectively, for a seat assembly in an exemplary user console.

FIGS. 5A, 5B and 5C are schematic side orthogonal views of a seated, reclined and elevated workstation configuration, respectively.

FIG. 6 is a schematic side orthogonal representation of an elevated workstation configuration.

FIGS. 9A to 9E are a front perspective view, a rear perspective view, a posterior orthogonal view, a side orthogonal view, and an anterior view, respectively, of an exemplary user console in a seated configuration.

FIGS. 10A to 10E are a front perspective view, a rear perspective view, a posterior orthogonal view, a side orthogonal view, and an anterior view, respectively, of an exemplary user console in a reclined configuration.

FIGS. 11A to 11E are a front perspective view, a rear perspective view, a posterior orthogonal view, a side orthogonal view, and an anterior view, respectively, of an exemplary user console in an elevated configuration.

FIG. 12A is a rear perspective view of a seat assembly with exemplary arm rest assemblies in the unfolded configuration.

FIG. 13A is a top view of another exemplary arm rest assembly including a sliding pin joint. FIGS. 13B, 13C, and 13D are top views of various configurations of the arm rest assembly of FIG. 13A.

FIGS. 14A and 14B are perspective views of a folded configuration and an unfolded configuration, respectively, of an exemplary arm rest in a user console. FIG. 14C is a side perspective of the folded configuration depicted in FIG. 14A. FIG. 14D is a top view of the unfolded configuration depicted in FIG. 14B.

FIGS. 14E and 14F are perspective views of retracted and extended configurations for an exemplary user interface platform with controls for a surgical instrument. FIGS. 14G and 14H are detailed views of engagement of controls with an exemplary user interface platform.

FIG. 15B is a detailed view of the user interface platform and controls in the exemplary user console shown in FIG. 15A.

FIG. 16 is a detailed view of the pedal assembly in the exemplary user console shown in FIG. 15A.

FIGS. 17A through 17E depict posterior views of variations of the user console.

FIGS. 24A and 24B are front perspective views of an exemplary user console with wheels on a display support and a seat assembly.

FIG. 28B is a detailed view of wheels on the base.

FIG. 29B is a detailed view of wheels on the base.

DETAILED DESCRIPTION

Non-limiting examples of various aspects and variations of the invention are described herein and illustrated in the accompanying drawings.

Robotic-Assisted Surgical System Overview

Figure 1A:
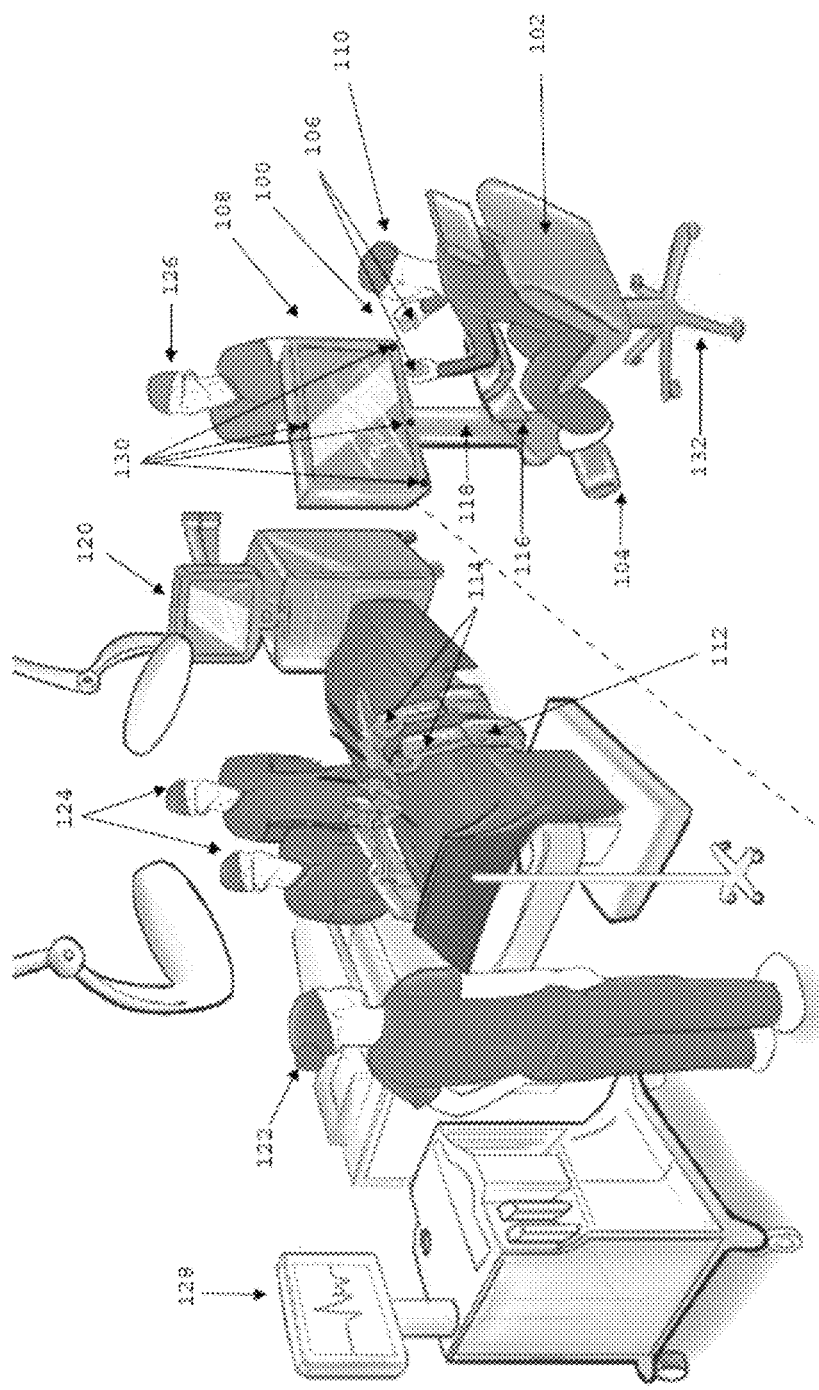

Generally, as shown in FIG. 1A, a user console 100 may be part of a robotic-assisted surgical system for interfacing with a robotic system 112. The robotic system 112 may include one or more robotic arms 114 located at a surgical platform (e.g., table, bed, etc.), where end effectors or surgical tools are attached to the distal ends of the robotic arms 114 for executing a surgical procedure. A user (such as a surgeon or other operator) may use the user console 100 to remotely manipulate the robotic arms 114 and/or end effectors (e.g., tele-operation). The user console 100 may be located in the same procedure room as the robotic system 112, as shown in FIG. 1A. In other embodiments, the user console 100 may be located in an adjacent or nearby room, or tele-operated from a remote location in a different building, city, or country. The communication between the user console 100 and the robotic system 112 may be wired and/or wireless, and may be proprietary and/or performed using any of a variety of data communication protocols.

In one example, the user console 100 comprises an adjustable ergonomic seat 102, a pedal assembly 104, one or more user interface devices 106, and a user display 108 configured to display a view of the surgical site inside a patient. A user located in the seat 102 and viewing the user display 108 may manipulate the pedal assembly 104 and/or user interface devices 106 to remotely control the robotic arms 114 and/or end effectors. At least one armrest 116 may be provided and supported by the display mount 118, as shown in FIG. 1A, and/or coupled to the seat 102, as shown in other variations herein. One or more secondary displays 120, which may, for example, display similar content as the user display 108, may also be provided so that an anesthesia provider 122 and/or other staff members 124, 126 can monitor the surgical procedure, provide assistance or respond to any issues, etc. A monitor 128 which can display vital signs may be switchable to the same view as provided on the secondary display 120 and/or include a picture-in-picture of video feed.

The pedal assembly 104 and/or user interface devices 106 may also be used to control other aspects of the user console 100 or robotic system 112, including adjusting or configuring the seat 102, the pedal assembly 104, the user interface device 106, and/or the user display 108, for example. One or more other input or output devices 130, such as a video sensor, speaker, keyboard and/or microphone, may be provided to facilitate voice recognition and/or manipulation of the user console 100 or robotic system 112, communication with other staff, eye tracking, and/or to provide access control or data security. In some other examples, the user console 100 does not include an integrated user display 108, but provides a video output that can be connected to one or more generic displays, including displays in the procedure room and/or remote displays accessible via the internet or other network.

As further described below with reference to additional examples, the seat assembly may comprise one or more adjustable features, including but not limited to seat rotation, seat height, seat tilt, seat back tilt, headrest height, headrest tilt. The armrest may be configured with adjustable armrest height, anterior/posterior position, and/or medial/lateral rotation, and where separate left/right armrests are provided, each armrest may be independently configurable. The armrest in FIG. 1A is coupled to the display mount 118, but in other examples may be coupled to the seat assembly. The adjustable seat features may be manually adjustable by the user and/or motorized, may be computer-controlled, with the configuration or profile configured to be stored and recalled via a seat controller, or some combination of both. Access to the seat controller may be performed through the user display 108.

During an exemplary procedure or surgery, the patient is prepped and draped in a sterile fashion, and anesthesia is achieved. Initial access to the surgical site may be performed manually with the robotic system 112 in a stowed configuration or withdrawn configuration to facilitate access to the surgical site. Once access is completed, initial positioning and/or preparation of the robot system may be performed. During the surgical procedure, a surgeon or other user in the user console 100 may utilize the pedal assembly 104 and/or user interface devices 106 to manipulate various tools and/or imaging systems to perform the procedure. Manual assistance may also be provided at the procedure table by sterile-gowned personnel 124, who may perform tasks including but not limited to retracting organs, or performing manual repositioning or tool exchange involving one or more robot arms 114. Non-sterile personnel 126 may also be present to assist the surgeon 110 at the user console 100. When the procedure or surgery is completed, the robotic system 112 and/or user console 100 may be configured or set in a state to facilitate one or more post-operative procedures, including but not limited to robotic system 112 cleaning and/or sterilization, and/or healthcare record entry or print-out, whether electronic or hard copy, such as via the user console 100.

In FIG. 1A, the robotic arms 114 are shown with a table-mounted system, but in other embodiments, the robotic arms may be mounted in a cart, ceiling or sidewall. The communication between the robot system 112, the user console 100 and other displays 120, 128 may be via wired and/or wireless connection(s). Any wired connections may be optionally built into the floor and/or walls or ceiling. In still other variations, the user console 100 does not include an integrated display 108, but provides a video output that can be connected to one or more generic displays, including remote displays accessible via the internet or other network. The video output or feed may also be encrypted to ensure privacy and all or portions of the video output may be saved to a server or electronic healthcare record system.

In the example depicted in FIG. 1A, the user console 100 utilizes a chair or seat assembly 102, which has a separate base 132 from the pedal assembly 104 or the display mount 118. In other examples, such as the user console 150 depicted in FIG. 1B, a seat assembly 152 may be integrated on a common base 154 with a pedal assembly 156 and display mount 158, armrest 160 and display 162, or otherwise be in communication with these components. The communication may be wired and/or wireless. Other variations of a user console 100 are described in greater detail below.

In other examples, additional user consoles 100 may be provided, to control additional surgical tools, and/or to take control of one or more tools at the primary user console. This will permit, for example, a surgeon to take over or illustrate a technique during a surgical procedure with medical students and physicians-in-training, or to assist during complex surgeries requiring multiple surgeons acting simultaneously or in a coordinated manner.

User Console

As described herein, a user console for controlling a remote surgical robotic instrument may provide a highly ergonomic, adjustable system from which a user may comfortably control a remote surgical robotic instrument. For example, the user console may be adjustable (e.g., automatically and/or manually) according to a seating profile associated with the user, surgical procedure type, and/or other parameters or settings. Additionally, the user console may facilitate easy, fast entry and/or exit by the user into the user console. For example, upon an indicated desire for entry/exit into the user console, the user console may automatically adjust to a configuration (e.g., to an elevated configuration, as described below) that a user can easily step into or step out of. Furthermore, the user console may be suitable for sterile use (e.g., use in the operating room).

Generally, as shown in FIGS. 3A and 3B, a user console 300 for controlling a remote surgical robotic instrument includes an adjustable ergonomic seat assembly 310, a display 350 configured to receive real time surgical information, and one or more controls 340 for remotely controlling the robotic instrument. As described further below, the seat assembly 310 may be selectively configurable in a plurality of user console configurations (e.g., seated, reclined, elevated). In some variations, other components of the user console (e.g., display, controls, etc.) may similarly have multiple positions or configurations corresponding to the user console configurations, where the other components automatically adjust their positions or configurations in response to a selected seat assembly configuration. Furthermore, one or more of the components of the user console may automatically adjust their relative positions and/or orientations according to a seating profile associated with at least one user, as further described below.

In another embodiment, as shown in FIGS. 2A-2G, a user console 200 for controlling a remote surgical robotic instrument may include a base 202, a seat assembly 204 coupled to a posterior region of the base 202, and a display 208 coupled to an anterior region of the base 202. These and other components and their variations are further described below. In one variation, the base 202 may be omitted such that the user console includes 200 includes a seat assembly 204 separate and modular from the display 208. In another variation, the display 208 as described herein may be optional, as the seat assembly 204 may be combined with a generic display or may be provided separately.

Since robotic instruments and equipment are typically sensitive to magnetic fields that may interfere with functionality, at least some of the user console may be made of plastic, foam, and other non-conductive materials. The user console may additionally include extra sensors to detect disruptions in the magnetic field in the room, so that personnel may take remedial steps to reduce interference.

Base

Figure 29A:
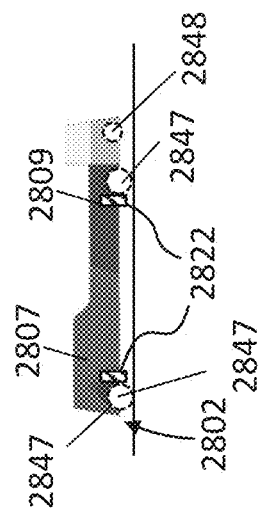
FIGS. 29A and 29B depict an exemplary variation of a base of a user console in a retracted or collapsed configuration, where
Figure 29B:
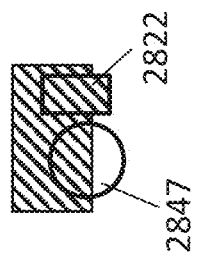
Figure 28A:
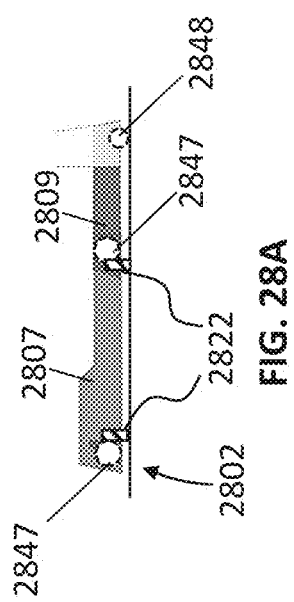
FIGS. 28A and 28B depict an exemplary variation of a base of a user console in an extended configuration, where

The base in the user console may function to provide support for adjustable relative positioning of the seat assembly and/or display, and/or other components. The base may be adjustable in at least one dimension (e.g., length and/or width). For example, as shown in FIGS. 28A and 29B, the base 2802 may be expandable/extendible and retractable/collapsible along an anterior-posterior direction. For example, in an expanded/extended configuration (e.g., while the user console is occupied or otherwise being used by a user) as shown in FIG. 28A, the base 2802 may include an anterior base portion 2809 that extends out of a posterior base portion 2807. In a retractable/collapsible configuration (e.g., for storage and/or transport) as shown in FIG. 29A, the anterior base portion 2809 may retract or collapse into the posterior base portion 2807 (or vice versa), which brings display assembly 2808 closer to the seat assembly 2804 and reduces the overall footprint of the user console. For example, anterior base portion 2809 may slide into an internal cavity or recess of the posterior base portion 2807 via a guiderail or other suitable track system. The extendibility and/or collapsibility of the base 2802 may be manually actuated (e.g., by a user pulling the two base portions apart, or pushing the two base portions together) and/or actuated with a leadscrew mechanism or other suitable actuator assembly. In some variations, the overall length of the base in its collapsed configuration (e.g., FIG. 29A) may be between about 50% and about 100%, or between about 65% and about 85%, of the overall length of the base in its extended configuration (e.g., FIG. 28A).

Figure 28B:
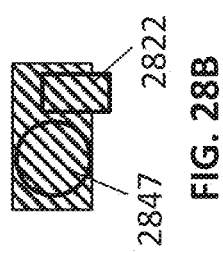

In some variations, the base 2802 may include one or more transport wheels 2847 for contacting a ground surface. The wheels may, for example, help improve overall mobility of the cart. In some variations, at least some of the wheels may be selectively deployable relative to the base 2802. For example, as shown in FIGS. 28A and 28B, when the user console is in use and the base is in an extended configuration, wheels 2847 may be retracted or otherwise disposed within the base 2802 and not in contact with a ground surface. In this configuration, static feet 2822 (e.g., pegs, etc.) coupled to and extending from an underside of the base 2802 may be in contact with the ground surface to support the user console (alternatively, the static feet 2822 may be omitted such that the underside of the base 2802 may contact the ground surface). Additional anterior wheels 2848 coupled to the anterior base portion 2809 may still contact the ground to facilitate base length adjustment in an anterior-posterior direction.

When the user console is to be transported or moved, the wheels 2847 may be deployed to raise the base 2802 above the ground surface. For example, as shown in FIGS. 29A and 29B, the wheels may be deployed (and base may be raised) such that the wheels 2847 extends beyond the static feet 2822 and/or leading wheels 2848, and the entire user console is supported by the wheels 2846 and 2847. With the user console supported by the wheels, the base 2802 may more easily be moved for storage and/or transport, etc. In this configuration shown in FIG. 29B, the wheels 2848 and anterior base portion 2809 are raised off the ground, such that the anterior portion of the base may more easily navigate over obstacles, thereby enabling the user console to more easily overcome obstacles on the ground (e.g., cables, debris, steps, etc.).

To restore the user console for an expanded "use" configuration, the wheels 2847 may be returned to a retracted position within the base. Locks and/or brakes may be engaged to help maintain the user console in the desired base configuration and/or location on the ground. In some variations, the wheels may be deployed and/or retracted via a hydraulic actuator system, or any suitable actuator system (e.g., gear train, handcrank or foot pedal system, etc.).

Additionally, when the base is adjusted to its collapsed configuration, the seat assembly and/or the display may further be adjusted such that the overall user console occupies a smaller volume. For example, the seat assembly and the display may be moved to lower positions. Generally, collapsibility may be useful for situations such as, for example, transportation between different locations (e.g., to and from the operating room, within an operating room, between hospitals, etc.) and for compact storage.

In another exemplary variation shown in FIGS. 2C-2G, the base 202 may include a posterior portion 206 and an anterior portion 210. The base may be relatively flat or level along its length, at least on a bottom surface to interface with the ground. Like the base 2802 described above, the base 202 may be adjustable in at least one dimension (e.g., length and/or width), such as with extendibility and collapsibility between an anterior base portion 209 and a posterior base portion 207. FIG. 2G illustrates a collapsed configuration, with the anterior base portion 209 retracted into the posterior base portion 207. Furthermore, other portions of the user console may collapse or fold to take up less volume, to reduce likelihood of damage during storage or transport, etc. For example, the support arm for the immersive display and/or an armrest (represented by volumes 221 and 222, respectively) may fold into more compact configurations, when the base is collapsed as shown in FIG. 2G or whenever not in use. When being prepared for use during a surgical procedure, the base may expand into an extended configuration, similar to that shown in FIGS. 2C-F. Similar to that described above, the base may include wheels 246 and/or 247 and may include locks or brakes that may be engaged to help keep the user console in a stationary location.

However, in some variations the base may be omitted (e.g., the seat pan, seat back, and/or other seat assembly components described below may be coupled to one another directly).

Seat Assembly

The seat assembly in the user console is preferably ergonomic and adjustable. In one embodiment, as shown in FIGS. 2A to 2G, a seat assembly 204 may comprise a seat support 214 attached to the base 202, with a seat shell 216 which is movably coupled to the seat support 214. A seat pan 218 (or seat bottom) and seat back 220 (or backrest) are coupled to the seat shell 216, but in other examples, the seat pan or seat back may be coupled to each other and/or to the seat support 214, without utilizing a seat shell.

The seat support 214 depicted in FIGS. 2A to 2G comprises a single pillar, but in other examples, the seat support may comprise two or more pillars. The seat support 214 has a longitudinal axis 242, depicted in FIG. 2C, that is angled posteriorly, but in other variations, may be angled vertically straight upward or tilted anteriorly. In some variations, the pillar angle, as measured between the pillar and the base plane anterior to the pillar, is in the range of about 80 degrees to about 160 degrees (e.g., about 150 degrees such that the angle between the pillar and the base plane posterior to the pillar is about 30 degrees), but in other examples may be in the range of about 90 degrees to about 135 degrees, or about 95 degrees to about 120 degrees. In the example depicted in FIGS. 2A to 2F, the seat support 214 has a fixed orientation relative to the base 202, but in other variations, the seat support may be configured to change its angle relative to the base, and/or to translate in the anterior-posterior directions and/or in the lateral directions. In some further variations, the seat support 214 may be configured to telescope or otherwise extend or retract longitudinally or generally vertically. In some examples, a posteriorly angled or tilted seat support may be beneficial to accommodate taller persons by not only providing vertical separation of the seat pan or back from the base, but also providing posterior separation of the seat pan or back from the pedal assembly or display assembly. In some variations, the position of the seat assembly 204 along the seat support 214 may be controlled by an actuator assembly (e.g., leadscrew coupled to one or more actuators, pulley assembly, other suitable gear assembly, hand-crank mechanism, etc.), and/or may be manually moved along the seat support 214 (e.g., by a user lifting or pushing the seat assembly 204). The position of the seat assembly 204 along the seat support 214 may be selectively locked with a brake mechanism, latch (e.g., pin), etc.

In some variations, a seat swivel position (e.g., rotational position around a vertical plane) may be adjusted by rotating the seat support 214 position relative to the base 202 of the user console. For example, a seat swivel position may be locked with a suitable locking mechanism, such as a brake, a latch (e.g., pin) or other suitable device. A lever, button, or other clutch mechanism may disengage the locking mechanism to enable a user to adjust the swivel position of the seat assembly 204 (e.g., manually or by shifting his or her weight while sitting in the seat). The base and/or seat support 214 may include one or more detents that enable secure positioning of the seat assembly 204 in one of a plurality of discrete swivel positions (e.g., left, center, right). Additionally or alternatively, the interaction of the base and/or seat support 214 may include a mechanism for enabling a continuous range of swivel positions, such as a friction-damped joint that requires application of at least a threshold amount of force to swivel the seat assembly.

Figure 9E:
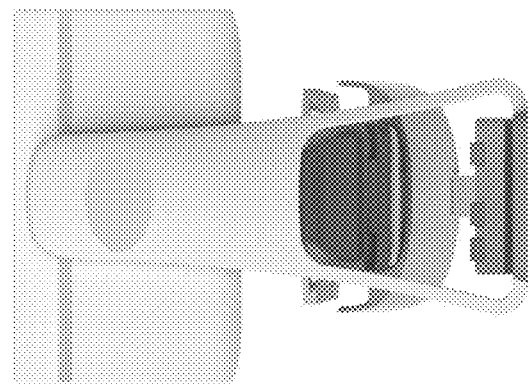
Figure 9D:
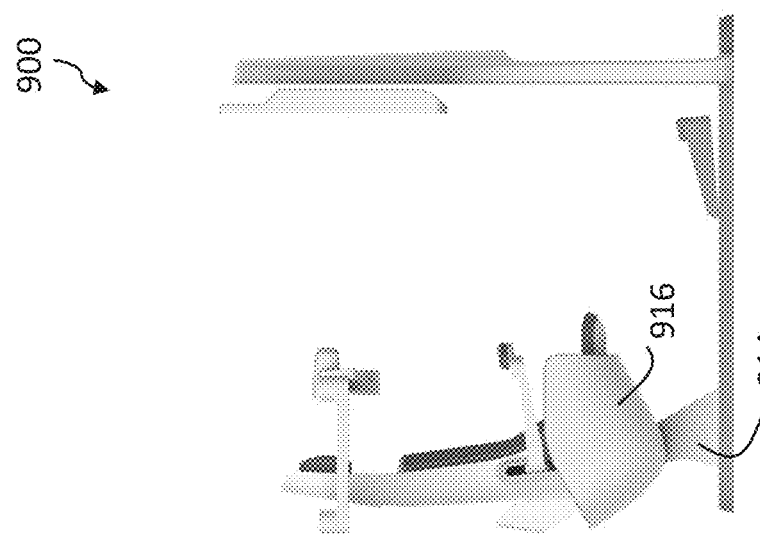
Figure 9C:
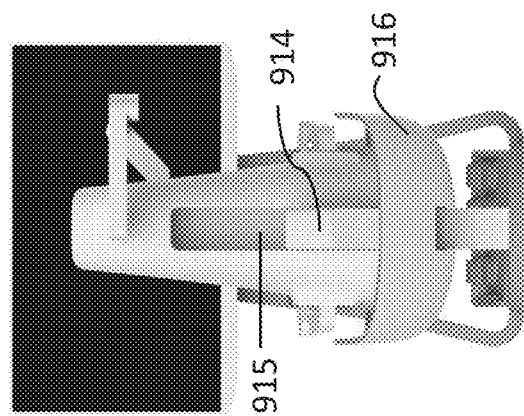
Figure 11C:
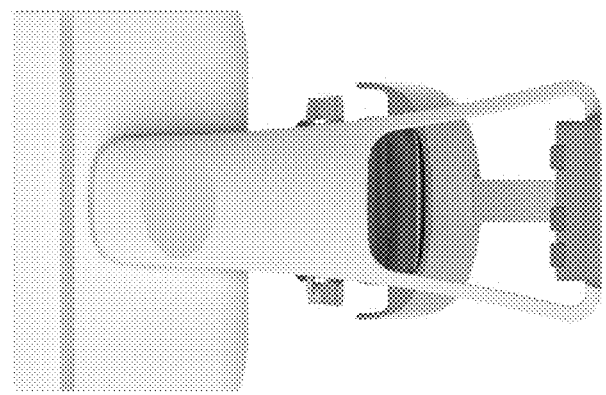
Figure 11D:
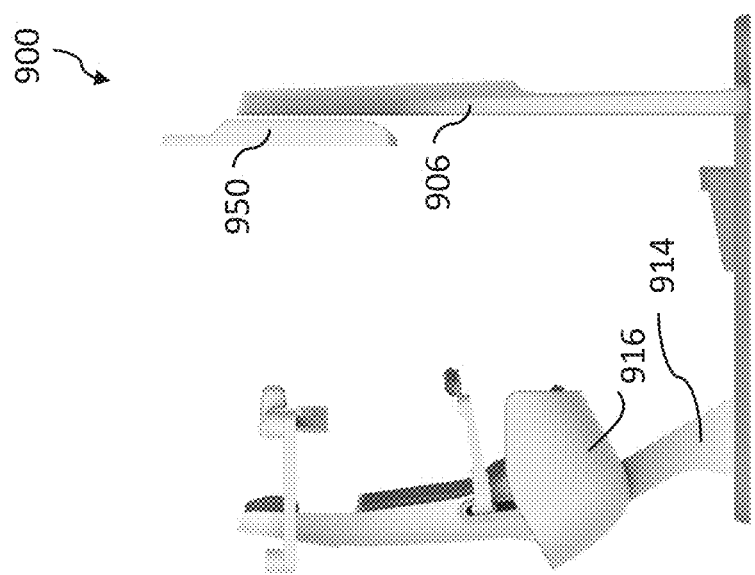
Figure 11E:
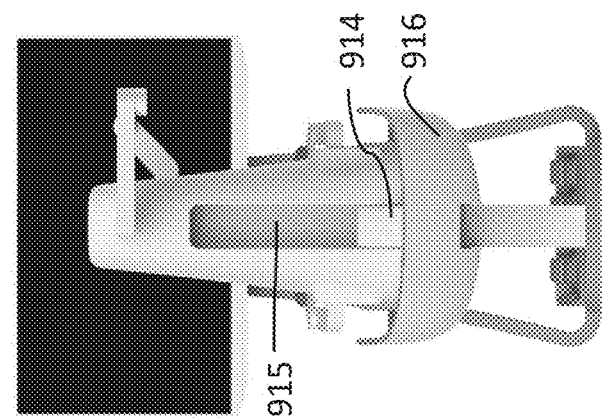

In another exemplary variation, as shown in FIGS. 9-11, a user console 900 is similar to user console 200 of FIGS. 2A to 2F, except as described below. For example, as shown in FIG. 9B, the seat back 920 defines a longitudinal cavity or slot 915 that receives seat support 914, which extends through seat shell 916 from the base 902. The longitudinal cavity may provide clearance for the seat support 914 as the seat assembly adjusts to different heights and angles. For example, as shown in FIGS. 9A-9E, when the seat assembly is in a seated configuration, the seat shell 916 may be at a moderate height such that a moderate (e.g., about half) length of the longitudinal cavity 915 is engaged with the seat support 914. As the seat assembly is generally lowered (e.g., in a reclined configuration), the seat shell 916 may be a lower height and more of the longitudinal cavity 915 may be engaged with the seat support 914 as shown in FIGS. 10A-10E. In contrast, as the seat assembly is generally raised (e.g., in an elevated configuration), the seat shell 916 may be at a higher height and less of the longitudinal cavity 915 may be engaged with the seat support 914 as shown in FIGS. 11A-11E.

Figure 2B:
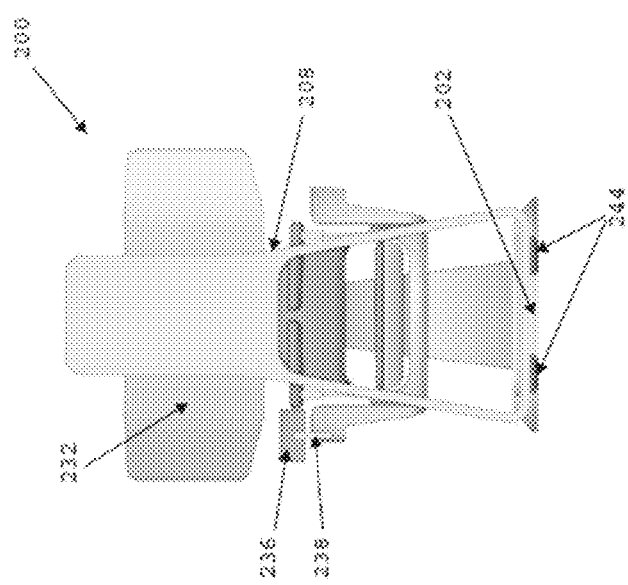
FIGS. 2A, 2B and 2C are anterior, posterior, and side orthogonal views of an exemplary user console with immersive and open displays.
Figure 2A:
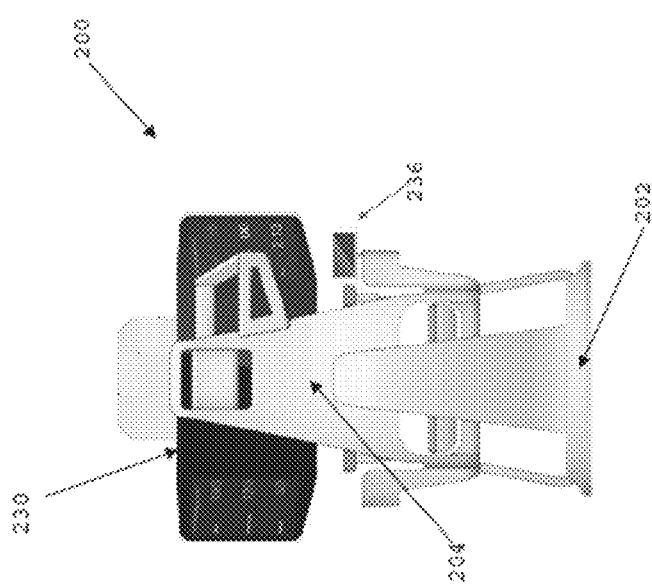
Figure 2D:
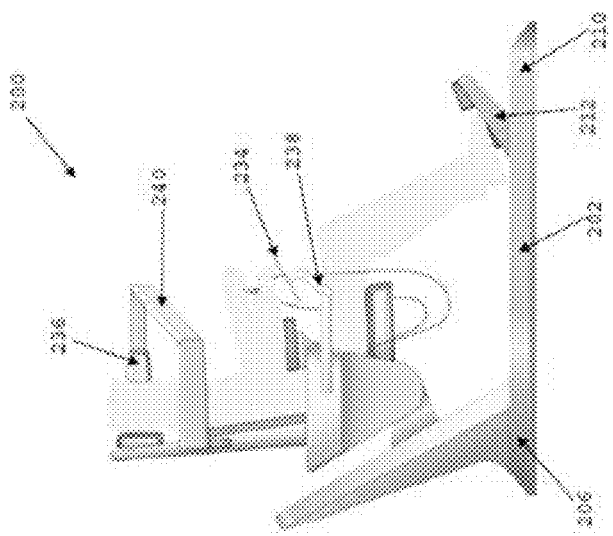
FIG. 2D is a side orthogonal view of another exemplary surgical console with an immersive display.
Figure 2C:
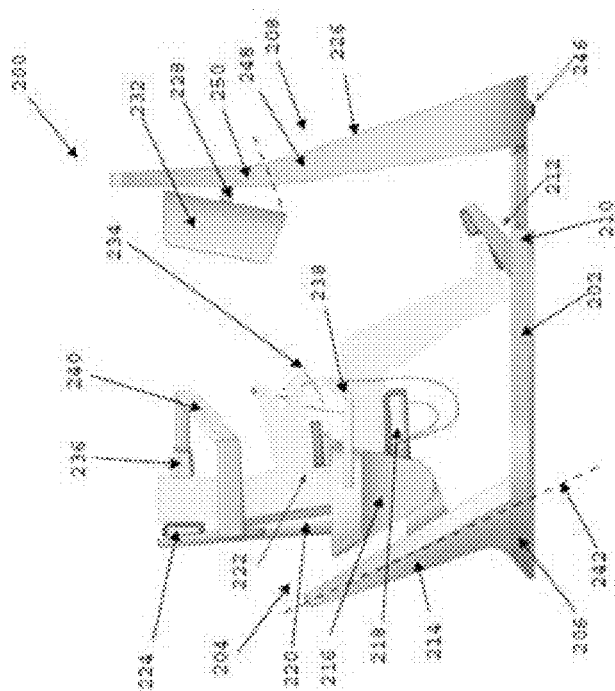

In some variations, the seat assembly may include at least one armrest. For example, as shown in FIG. 2C, the seat assembly 204 may further include an armrest 222 that is coupled to the seat shell 216, seat pan 218 or seat back 220. As previously described, the at least one armrest may also be coupled to the display mount, or other suitable location on the assembly. As another example, as shown in FIG. 12A, the seat assembly may include two or more armrest assemblies 1222, including a left armrest assembly and a right armrest assembly. The armrest assemblies 1222 may be coupled to respective left and right sides of the seat back 1220 in an adjustable manner (e.g., hinge joint to provide vertical pivoting, screw joint, cylindrical joint, etc.). For instance, the armrest assemblies 1222 may be vertically translatable in a prismatic joint to enable armrest height adjustment relative to the seat back 1220 by moving along slots 1223. In other variations, the proximal end of the armrest assembly may be mounted to a seat pan, seat back, and/or other suitable portion of the seat assembly. The armrest may additionally include straps, bars, or other supporting structures passing over the arm of the user, which may help secure the user's arms in place.

The armrest may be collapsible (e.g., on or against the sides of the seat assembly) and extendible (e.g., along the front of the seat assembly) to allow user access to the seat assembly and to secure the user in the seat assembly, respectively. For example, the armrest 222 may collapse against the side of a seat shell 216 as shown in FIG. 2G, and extend anteriorly across the seat assembly as shown in FIGS. 2C-2F. Furthermore, one or more armrests may swing laterally outward, with or without collapsing, to allow user access to the seat assembly. The armrest may be curved (e.g., with a concavity facing inward toward the seat) or otherwise shaped to facilitate lateral outward motion, which may allow a user to force the armrest to swing laterally outward by pushing with a forearm, stomach, etc. (e.g., to maintain sterility of the user's hands).

The armrest may include a plurality of links connected by joints. The joints of the armrest may comprise any of a variety of joints, including pin joints, fork joints, and planar or sliding pin-in-slot joints, ball-in-socket joints, and the like. One or more joints may be controlled by one or more motors, brakes, and/or clutches, so that the desired armrest configuration may be saved and/or automatically set. Force sensors may be provided to sense and reduce impingement by a motor driven joint on the user. Each joint may also include position sensors or encoders to determine the position of one more joints of the armrest. The joint information may be used to determine, or confirm of the armrest, and/or to set or change the configuration or state of the user console or robotic system, e.g. in pause state, user entry state, user exit state, etc.

Figure 12B:
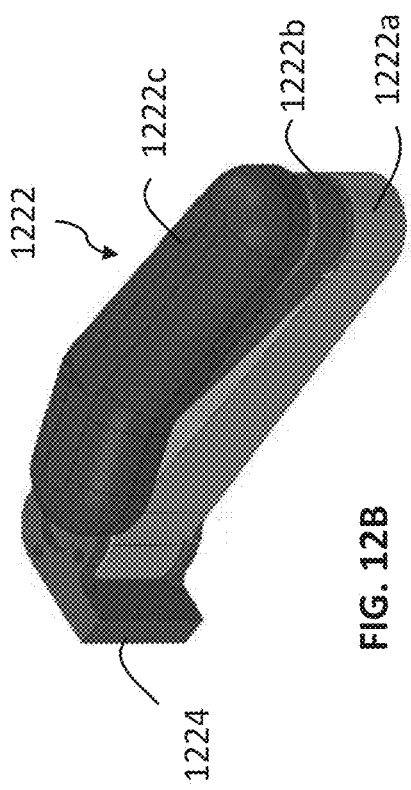
FIGS. 12B and 12C are perspective views of an exemplary arm rest assembly in a folded configuration and an unfolded configuration, respectively.
Figure 12C:
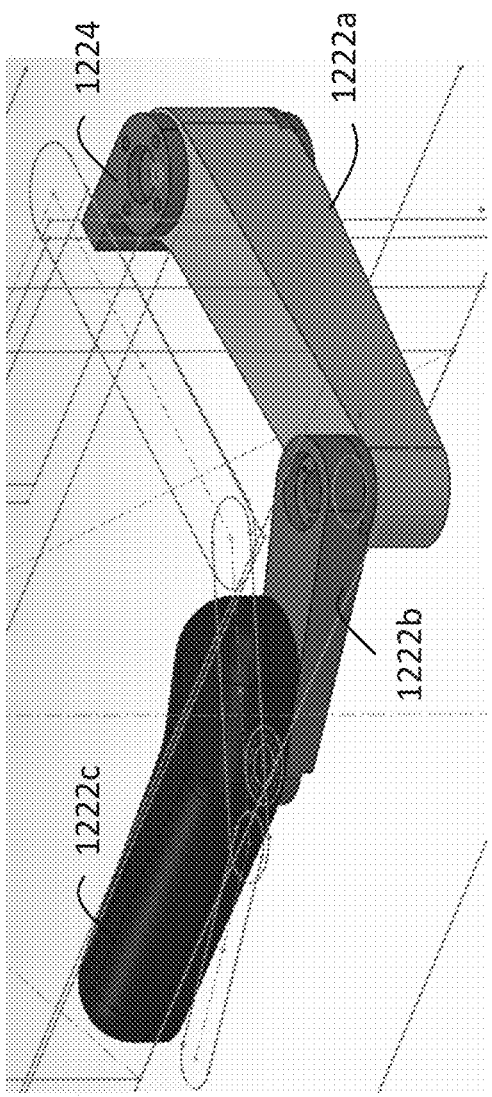

For instance, as shown in FIGS. 12B and 12C, each armrest assembly 1222 may include a set of multiple articulated links (e.g., 1222a, 1222b, 1222c, etc.) that are serially and pivotally connected and configured to enable a folded configuration and an unfolded configuration or vary an effective extended length. Each armrest assembly 1222 may be mounted or coupled to a left or right side of the seat assembly or other suitable location. For example, the armrest assembly 1222 may be coupled to a side of the seat assembly via proximal support 1224 which is rotatably coupled to a link such as 1222a, or fixedly mounted to a side of the seat assembly via a mounting plate with fasteners. In the folded configuration (FIG. 12B), the armrest links 1222a, 1222b, 1222c are collapsed and stacked on top of each other in a compact pose on their respective sides of the seat assembly. The relative lengths of the links may be designed to facilitate efficient folding. For example, the second link 1222b may be shorter than first link 1222a so as to permit the second link 1222b to rotate completely over the first link 1222a without encountering mechanical interference with the proximal support 1224. When both left and right armrest assemblies are in the folded configuration, the seat assembly is open and more easily accessible by a user to sit down in the seat assembly. From the folded configuration, the armrest links may at least partially pivotally unfold as shown in FIG. 12C, such as into the unfolded configuration. In the fully unfolded configuration, such as that shown in FIG. 12A, the distal ends of the armrest assemblies 1222 may point toward one another, so as to encircle a user that is seating in the seat assembly. Different amounts of arm rest extension may be appropriate as unfolded configurations for different user console configurations, different users (e.g., depending on girth or weight), etc. Although FIGS. 12B and 12C depict an armrest assembly 1222 with three arm links, in other variations, the armrest assembly may include three, four, or any suitable number of articulated links for enabling various desired armrest configurations.

Figure 12D:
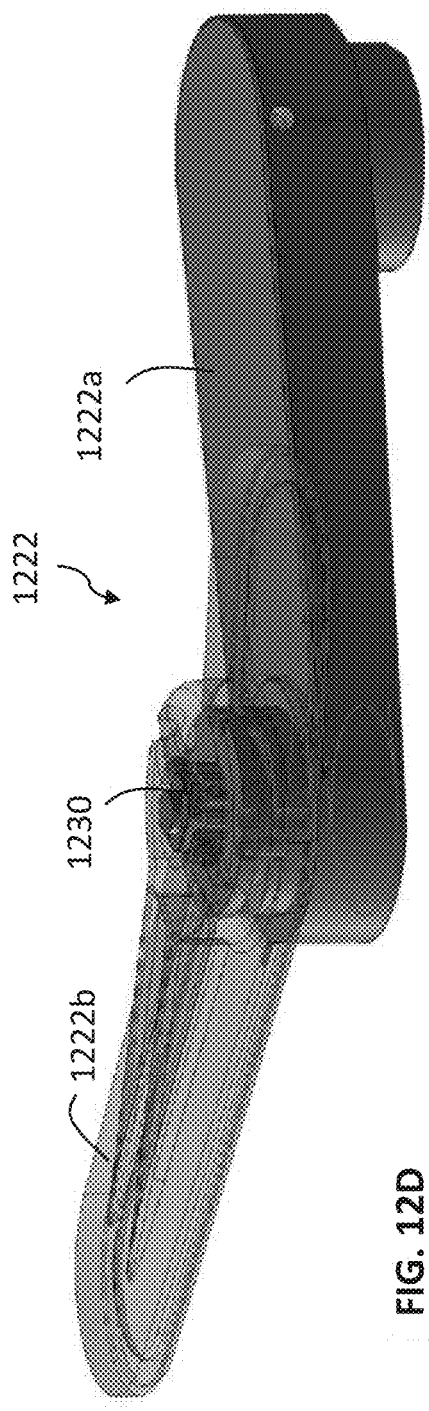
FIG. 12D is a detailed partial view of an exemplary arm rest assembly.
Figure 12E:
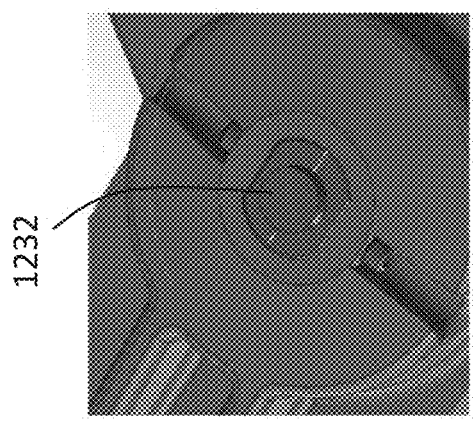
FIG. 12E is a detailed view of a joint in an exemplary arm rest assembly.

Movement between the folded and unfolded configurations may be controlled manually and/or with one or more actuators (e.g., stepper motors or servomotors) and may be controlled automatically. For example, as shown in FIGS. 12D and 12E, a pivot joint between two arm links 1222a and 1222b may include an actuator 1230 with shaft 1232. The two arm links 1222a and 1222b may be coupled with a pin joint or other rotatable joint. For instance, the distal end of first link 1222a may include a circular hub configured to rotatably engage with a circular recess in the proximal end of second link 1222b (e.g., with a bearing, a tongue-and-groove fit or other key, etc.). Additionally, the circular hub on the distal end of first link 1222a may house the body of actuator 1230 and the proximal end of link 1222b may be coupled to the shaft 1232 (e.g., press-fit, pins, epoxy, etc.) directly or indirectly such as with gears, chains, cables, or other drive coupling mechanisms. When the actuator 1230 receives suitable commands for folding or unfolding, the actuator 1230 may cause link 1222b to pivot relative to link 1222a by a prescribed angle and/or rate. The armrest assembly 1222 may include an actuator for some or all of its articulated joints (e.g., link 1222c may be similarly actuated to pivot relative to link 1222b). Actuators may periodically or intermittently command the armrest assembly to move a prescribed amount (e.g., slightly with micromovements) to reduce fatigue in the user's arms over an extended period of time during a surgical procedure.

The armrest assemblies may be locked or secured in the unfolded configuration (or a partially unfolded configuration) to help secure a seated user in the seat assembly (e.g., the armrest assemblies may resist at least up to certain amount of force, such as a user pushing the armrest assemblies outward before collapsing). For example, the actuator 1230 at an articulated joint between two arm links 1222a and 1222b may be commanded in a "lock" position, such as backdriving when sensing a user force in a particular direction, and/or brakes (not pictured) may be engaged to hold the armrest assemblies in the unfolded configuration. As another example, the distal ends of left and right armrest assemblies may touch and/or lock mechanically to one another, and conversely be related (e.g., with a button, a latch mechanism) so as to secure the armrest assemblies in the unfolded configuration or release the armrest assemblies from the unfolded configuration. The joints may be moved and maintained or locked into a desired position, for example, using a mechanism such as friction fit joints, detents, or a joint with a releasable friction fit or mechanical interlock. However, the "lock" position or locking mechanism, if present, may be overcome by a user force exceeding a certain threshold value such that a user may urgently break out of the seat assembly in the case of emergency or if otherwise needed. Additionally or alternatively, the user console may include an emergency mode (engageable by button, clutch, voice command, etc.) that automatically disables all "lock" positions or locking mechanisms.

In other variations, the seat assembly may include only one armrest assembly that is mounted on one side (e.g., left or right) of the seat assembly and is extendable to a length that spans at least most of the width of the seat assembly, or the seat assembly may include one or more armrests that are configured to extend or otherwise move in an overhead approach (e.g., over the back of the seat back). Other variations of collapsible and extendible arms are also contemplated. For instance, at least one arm link may additionally or alternatively translate relative to another link to facilitate collapsibility and extendibility, such as with telescoping links and/or sliding pin joints. As shown in FIGS. 13A-13D, for example, an armrest assembly 1322 may include a first link 1322a, a second link 1322b, and a third link 1333c, which pivot relative to one another similar to armrest assembly 1222 described above. However, additionally, second link 1322b or another link may translate relative to the first link 1322a (e.g., via sliding pin joint) to provide an additional degree of freedom for more configuration flexibility in the armrest assembly. For instance, FIG. 13B depicts the second link 1322b in a longitudinally extended, slightly midline angled position and with the third link 1322c in a medial transverse orientation. FIG. 13C depicts the second link 1322b in a longitudinally aligned, extended position relative to the first link 1322a, and the third link 1322c also in a longitudinally aligned, extended position in a forward orientation. FIG. 13D depicts the second link 1322b in a longitudinally aligned, at least partially retracted position relative to the first link 1322a, such that a portion of the third link 1322c is overlying the first link 1322a. Like the armrest assembly 1222, one or more of the joints between arm links in the armrest assembly 1322 may be actuated with a respective actuator and be configured for automatic control. Other variations of armrest assemblies may incorporate different numbers of links, as well as other combinations of sliding pin joints and/or non-sliding pin joints.

In an exemplary variation shown in FIGS. 14A and 14B, an arm support linkage 1400 may be coupled to or adjacent a seat assembly. The arm support linkage 1400 may be movable between a folded configuration (FIG. 14A) and at least one unfolded configuration (e.g., FIG. 14B). For example, the folded configuration may be suitable for permitting a user to enter and exit the user console, or for purposes of storage and/or transport, etc.

One or more various unfolded configurations may correspond to a desired position of the arm support for a user, depending on a user characteristic (e.g., user size such as height, weight, or girth) and/or a surgical task characteristic (e.g., type of surgical procedure that the user is performing with the robotic surgical system). Generally, the unfolded arm support may be configured with adjustable arm support height, anterior/posterior position, and/or medial/lateral rotation, and where separate left/right arm supports are provided, each arm support may be independently configurable. The adjustable arm support features may be manually adjustable by the user and/or motorized, or may be automatically configurable and computer-controlled. Adjusted arm support configurations and settings may be stored in memory as part of a profile associated with a particular user and/or type of user, with the configuration(s) or profile configured to be stored and recalled via a seat controller. Access to the seat controller may be performed, for example, through a user display or touchscreen.

One or more of the unfolded configurations may furthermore help provide an enclosure in front of the user when the user is positioned in the seat assembly, thereby securing the user in the seat assembly. Although FIGS. 14A and 14B depict only one arm support linkage 1400 adjacent to the seat assembly, it should be understood that in some variations, at least two arm support linkages may be adjacent to the seat assembly. For example, the user system may include first and second arm support linkages coupled to or otherwise adjacent to opposite sides of the seat assembly. The first and second arm support linkages may be mirrored versions of each other (e.g., a left-side arm support linkage and a mirrored right-side arm support linkage which unfold generally toward the centerline of the seat assembly).

The arm support linkage 1400 in a user console may include a linkage assembly including a proximal segment 1410, an intermediate segment 1420, and a distal segment 1430. The proximal segment 1410 may be attached to the seat assembly (e.g., on the side of the seat, with a wraparound fixture to a backset of the seat, or with a wraparound fixture to an underside of the seat, etc.), either directly or through an intervening base structure such as one or more additional proximal segments that attaches to the seat in a similar manner. In other examples, the arm support linkage 1400 may be coupled to the ground (e.g., coupled to a base resting on the ground), or to another portion of the user console. In some variations, the linkage assembly may include fewer or more segments. The segments may be connected by pivotable joints. For example, as shown in FIGS. 14C and 14D, the proximal segment 1410 and the intermediate segment 1420 may be coupled at joint 1412 such that the proximal and intermediate segments may move relative to one another at joint 1412. Similarly, the intermediate segment 1420 and the distal segment 1430 may be coupled at joint 1422 such that the intermediate and distal segments move relative to one another at joint 1422. Accordingly, articulation of the joints 1412 and 1422 may enable the arm support linkage to move between folded and unfolded configurations as desired.

In some variations, the arm support linkage may include a SCARA (Selective Compliance Assembly Robot Arm) linkage that is articulated along parallel axes, such as parallel axes passing through joints 1412 and 1422 (e.g., such that the arm support linkage is generally compliant in an X-Y direction via rotation around the parallel axes but substantially rigid in a Z-direction). For example, the intermediate segment 1220 may rotate relative to the proximal segment 1410 via joint 1412 in an X-Y direction, and the distal segment 1430 may rotate relative to the intermediate segment 1420 via joint 1222 in an X-Y direction. However, joints 1412 and 1422 are shown as pin joints collectively providing 2 degrees of freedom, such that joints 1412 and 1422 substantially prevent movement of the intermediate segment 1420 and the distal segment 1430 in a Z-direction. In other variations, the arm support linkage may include any suitable kind of linkage (e.g., providing three or more degrees of freedom, including telescoping linkage segments, etc.).

In some variations, all of the segments of the arm support linkage may generally rotate within the same plane. In other variations, at least one segment of the arm support linkage may generally rotate in a separate respective plane (e.g., that is offset from other segments with spacers, etc.). For example, as shown in FIG. 14C, the proximal segment 1410 and the intermediate segment 1420 may generally be rotatable in the same plane, while the distal segment 1430 may generally be rotatable in a different plane than the proximal segment 1410 and the intermediate segment 1420. In other words, the intermediate segment 1420 may rotatable within a first plane via the pin joint 1412, and the distal segment 1430 is rotatable within a second plane via the pin joint 1422, where the second plane is parallel and offset from the first plane. In other variations, the arm support linkage may include any suitable linkage (e.g., a linkage that is articulable in at least two orthogonal planes).

Figure 4A:
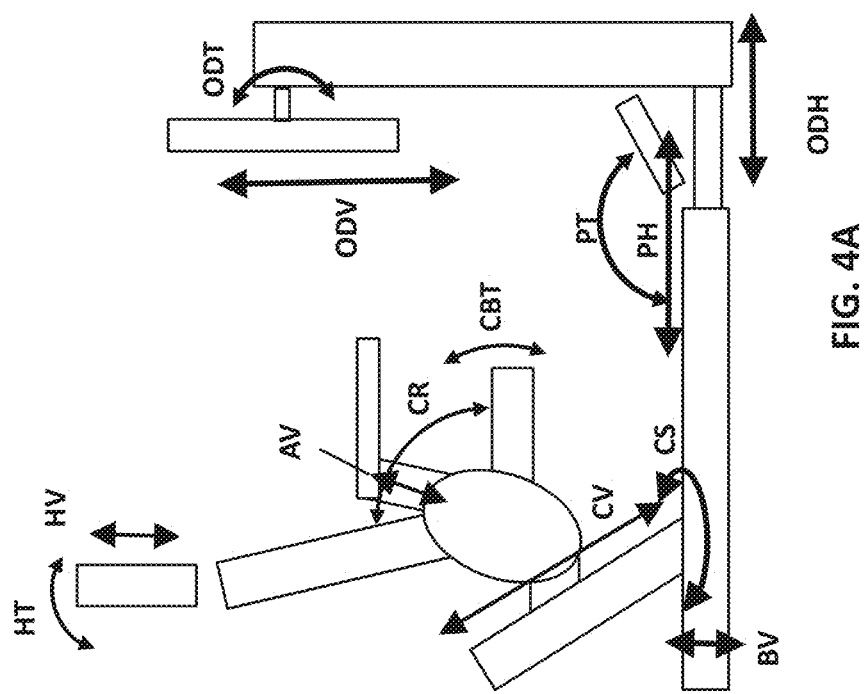
FIG. 4A is a schematic illustration of adjustable settings or parameters of an exemplary user console.

The seat assembly may further include a headrest. For example, as shown in FIGS. 2A-2F, the seat assembly 204 may include a headrest 224 attached to a superior portion of the seat back 220. Alternatively, the headrest may be coupled to the seat back with a hinge joint, one or more longitudinal members, extendible bellows or accordion arrangement, extendible telescoping arrangement, etc. In some variations, a headrest portion of the seat assembly 310 may be coupled to a seat back via a hinge joint or other suitable joint to facilitate adjustment in the angle of the headrest portion relative to the seat back. The headrest pad may be movably coupled (e.g., along at least one track or rail) to the headrest portion to adjust height of a resting location for the user's head. Accordingly, as illustrated in the schematic of FIG. 4A, height adjustment and angle adjustment for the headrest may be decoupled from one another, allowing for more combinations of headrest height and angles. As with other aspects of the user console, the height of the headrest may be adjusted manually or automatically, based on user configurations, profiles, and/or preferences.

In some variations, the headrest (or a portion of the seat assembly near the headrest) may include audio equipment. For example, the headrest may include a microphone and/or speaker embedded in or coupled to the headrest, such as for enabling communication with personnel (e.g., assistants outside the room or otherwise located at a remote location) to direct commands, receive instructions, provide noise-cancelling functionality, etc. The audio equipment may additionally or alternatively be coupled with a wired or wireless communication (e.g., Bluetooth protocol) to auxiliary devices, such as a telephone or the display assembly, such as for participating in telephone conversations, listening to music, etc. In another example, there may be provided a headset with a microphone and/or speaker that is wearable by the user and coupled to the headrest via a wired or wireless communication.

Figure 8B:
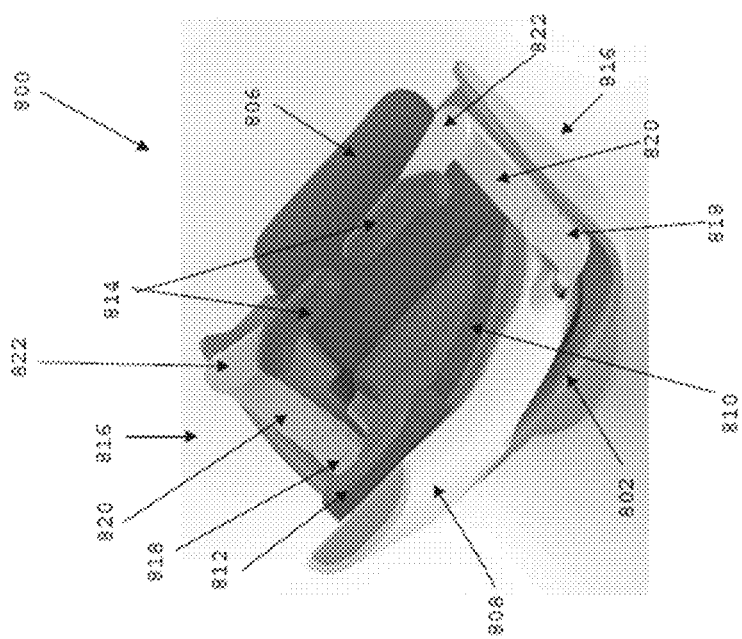
FIGS. 8A and 8B are anterior orthogonal and superior perspective views of an exemplary seat with arm rests in an unfolded configuration.
Figure 8A:
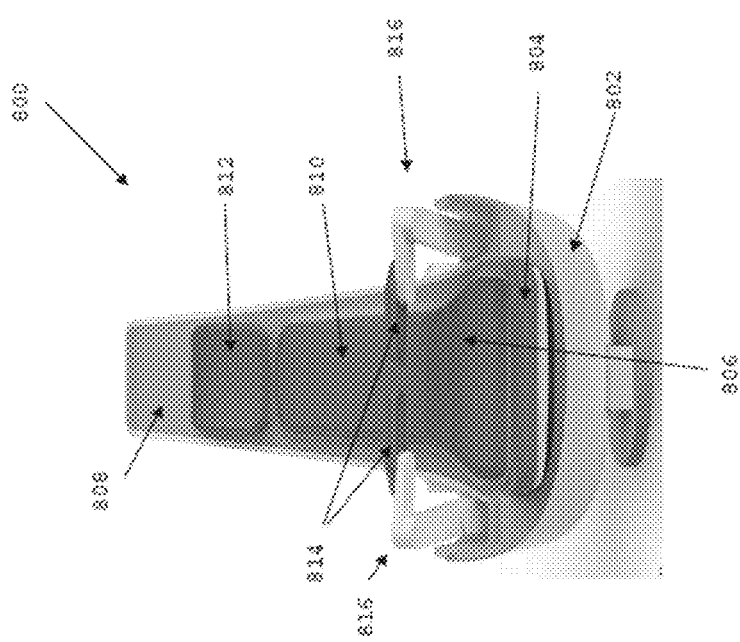

The surfaces of the seat pan, seat back, headrest and armrests, if any, may comprise a hard surface, and/or a soft surface, including a foam or gel cushion, cover or structure. The surface may be porous or closed, and the cushion or structure may be configured to be removably attachable to the rest of the seat pan, seat back, headrest and/or armrests. The attachment may be performed using hook and loop fasteners, buttons, snaps, zippers, laces, tongue-and-groove interlocks, and the like. Depending on the type of attachment, the user may select from a variety of cushion types, shapes and styles that can be used with the seat assembly, and may also be able to manually adjust the positioning of the cushion, e.g. with hook and loop fasteners. In other examples, one or more of these cushions may be circular, oval, or a polygonal shape. FIGS. 8A and 8B depict one example of a seat assembly 800 with a bottom seat shell 802. Coupled to the seat shell 802 is a seat pan 804 with a bottom cushion 806, a seat back 808 with a back cushion 810 and a headrest cushion 812. The bottom cushion 806 and the headrest cushion 812 may comprise a rectangular shape, and back cushion 810 may have a tapered shape from bottom to top. In this variation, each of the cushions 806, 810, 812 comprises rounded corners and rounded edges, but in other examples they may have squared corners and/or edges. In some other examples, the back cushion and headrest cushion may be integrated, as can the bottom cushion and the back cushion, for example. Armrest cushions 814 may also be provided. These armrest cushions 814 can be located at the distal regions of a multi-link armrest 816, with a proximal support 818 movably coupled to an intermediate support 820 and a distal support 822. The armrest cushions 814 may have an arcuate or angled configuration, but in other examples, may comprise a straight or other shape, such as an oval or paddle shape.

FIGS. 17A-17E depict exemplary variations of seat assemblies. In these variations, the seat assemblies are similar in that each has a seat support 1714 that articulates along a posterior recess of a seat shell 1716, and the seat pan and seat back 1704 are coupled to the seat shell 1716, as well as a pair of armrests 1722. Additionally, the seat assemblies include a headrest 1730. However, the shapes and relative sizes of the various seat assembly components may vary. For example, as shown in FIG. 17A, the seat back 1704 may have a wider inferior portion that generally linearly tapers to a narrower superior portion, and the headrest portion 1730 may include a cushion that extends laterally wider beyond either side of a superior portion of the seat back 1704. As shown in FIG. 17B, the seat back 1704 may be approximately the same width along its length such that an inferior portion of the seat back 1704 is about the same width as a superior portion of the seat back 1704. As shown in FIG. 17C, the seat back 1704 may include a generally wider square or rectangular inferior portion, a linearly tapering intermediate portion, and a narrower superior portion by headrest 1730. As shown in FIG. 17D, the seat support 1714 and seat back 1704 may have generally curvilinear profiles instead of linear, angular profiles. As shown in FIG. 17E, the seat back 1704 may be similar to the seat back of FIG. 17B except that FIG. 17E depicts a slightly narrower seat back 1704, with cushions for headrest 1730 and seat back 1704 both extending laterally wider beyond either side of the seat back 1704. In other variations, different sizes and/or shapes of the components of the seat assembly may be combined in any suitable manner.

Various components of the seat assembly may be adjustable to provide ergonomic and other mechanical customizations for a particular user or user type. In addition to longitudinal or vertical movement of the seat assembly with respect to the seat support, other seat adjustment movements, including but not limited to seat shell rotation around its own vertical axis or around the seat support, seat shell forward/backward tilting relative to the seat support, seat pan forward/backward tilting, seat pan anterior/posterior translation, seat back forward/backward tilting, seat back vertical translation, seat back forward/backward tilting, seat back anterior/posterior translation, headrest vertical translation, headrest forward/backward tilting, headrest anterior/posterior translation, armrest proximal lateral rotation, armrest distal lateral rotation, armrest vertical translation, and/or other seat assembly adjustments may be provided. These and other movements are described in greater detail below.

Referring to the exemplary embodiments of FIGS. 2A-2F, the adjustments to the seat assembly 204 may be performed manually by the user, and/or may be performed automatically by a controller via one or more actuators or drive motors. The controls may be provided by one or more physical buttons, sliders or switches on the seat assembly 204, pedal assembly 212, the display assembly 208, and/or an auxiliary display or panel 234. The controls may also be manipulated via the user interface devices.

The actuators or drive motors, if any, for the adjustment mechanisms in the seat assembly may be located in the seat shell, pillar(s), base, seat pan, seat back, or other location in the seat assembly or the user console. Adjustment mechanisms may be directly driven by a motor, or may be mechanically connected by one or more gears, belts, chains, or linkages. The actuators may be any of variety of suitable motors, including DC motors with or without brushes, and/or synchronous or induction AC motors, solenoid actuators, and the actuators may be backdriveable or non-backdriveable, for example. In some examples, one motor may be configured for use with multiple adjustment mechanisms, using a clutch or transmission system. For example, a single motor provided in the seat support 214 may be used for longitudinal adjustment of the seat assembly 204, but may also be used for adjustments of the pedal assembly 212 and/or the display assembly 208, via belts, chains or other mechanical linkages. In other examples, however, the pedal assembly 212 and/or display assembly 208 may comprise additional motors for performing the adjustments.

The seat assembly may include sensors (e.g., position sensors, joint encoders) to monitor and/or confirm the mechanical adjustments being performed. These sensors may also be used in a calibration procedure and/or safety check. For example, one or more of the adjustments may be brought though its range of adjustment or a test range of motion to confirm or test proper function. In systems in which one or more motors are coupled to a cable, chain, gear, or other drive mechanism to transfer force to a location away from the motor shaft, one or more sensors may be located in a variety of locations through the drive mechanism, such as to identify any elasticity, laxity, slippage, creep, etc. in the drive mechanism. Upon detecting such characteristics in the drive mechanism, the system may provide compensatory forces to achieve the desired mechanical adjustment, and may provide an error or warning message if the expected mechanical adjustment is not detected. In some variations, the seat assembly may include one or more sensors (e.g., pressure sensors, position sensors detecting chair swivel) that indicates the presence or absence of a user in the seat assembly. Other mechanisms in the seat assembly, such as vibration motors, may be provided to provide haptic feedback to the user indicating status of various components of the user console, robotic instrument, etc. For example, the seat assembly may vibrate in the seat pan, seat back, headrest, armrest, etc. to indicate warnings such as when a user interface device (described below) is exceeding its trackable workspace.

One or more of the adjustment mechanisms for the seat assembly 204 may include a locking mechanism to maintain the configuration of the adjustment mechanism once it is set by the user. In some examples, a non-backdriveable motor may be provided, and a locking mechanism may or may not be provided. The locking mechanism may be a friction brake or a releaseable mechanical interlock, such as a locking pin mechanism. A counter-weight or counter-balance mechanism for may also be provided to reduce the load on the motor or user during seat adjustment.

Controls

The user console may include one or more controls or user interface devices for remotely controlling a robotic instrument and/or controlling other aspects of the system. The controls may, for example, may be manipulated by a user to operate a robotic arm, operate an end effector attached to an end of a robotic arm, operate the user console for adjustments, operate or navigate a graphical user interface, etc.

In one variation, as depicted in FIG. 1A, the user console 100 includes at least one hand-operated control or user interface device, such as one or more user interface devices (e.g., a pair including a left controller and a right controller), which are tracked in 3-dimensional space over time. Other hand-operated controls may include, for example, joysticks, graspers, pincers, etc. The user interface devices 106 may be wired or wireless, may include one or more accelerometers in one or more axes, and may be tracked via any of a variety of mechanisms, including but not limited electromagnetic tracking or optical tracking, using active and/or passive emitters. Transmitters for the hand-operated control may be located, for example, on the user console base, on the armrest or headrest or other portion of the seat assembly, and/or any other suitable portion of the user console. The controllers 106 may include haptic feedback mechanisms, as well as mechanical or touch actuators to facilitate further manipulation of the robotic system 112, or various controls and adjustment settings of the user console 100 itself. For example, in some variations, the controllers 106 may be used to test or confirm spatial registration of surgical tools (robotic tools, manual tools, etc.) by providing short vibrational impulses, etc. as tactile feedback to the user. Additionally, the controllers 106 may be used to provide a form of user identification (e.g., gesture-based or biometric identification through fingerprints).

In some variations, the one or more user interface devices may be permanently or releasably mounted to a docking station (e.g., on an armrest in front of the seated user, a secondary platform), to another suitable user interface device mount or receptacle (e.g., hooks, cups) and/or independently handheld by the user. For example, the armrest in the user console may include a mount portion for docking at least one user interface device. For example, a user interface device may be placed in the mount portion when the user (e.g., surgeon) desires to take a break from teleoperating the robotic surgical system with the user interface device (e.g., to rest or to switch between different operating techniques), and/or for storage or transportation purposes. For example, as shown in FIGS. 14C and 14D, an arm support linkage 1400 may include a mount portion 1624 coupled to the intermediate segment 1620. The mount portion 1624 may include a cradle, tray, recess, hook, or other receptacle for receiving a user interface device 1428. The mount portion 1624 may be integrally formed (e.g., through injection molding) with the intermediate segment 1620, or may be formed separately and coupled to the intermediate segment 1620 via fasteners, threads, snap-fit, other suitable interference fit, or in any suitable manner. In other variations, the mount portion may be integrally formed with or coupled to any other suitable portion of the arm support linkage or user console. In some variations, the mount portion (or another portion proximate the mount portion) may include one or more sensors for detecting whether a user interface device is docked in the mount portion. For example, proximity sensors, electromagnetic sensors interacting with the user interface device, or any suitable sensor may be used to determine whether a user interface device is docked. In variations in which the user console includes mounting locations for more than one user interface device (e.g., more than one docking location on a single arm support linkage, or more than one arm support linkage each with a respective docking location), the one or more sensors may be used to detect which of the multiple user interface devices are docked and/or whether all of the multiple user interface devices are docked. The one or more sensors may additionally or alternatively determine whether a user interface device is properly docked (e.g., in a secure manner, or with a left-side user interface device docked on a left-side arm support linkage and a right-side user interface device docked on a right-side arm support linkage).

The mount portion may be hidden (e.g., relatively inaccessible to the user) when the arm support linkage is in the folded configuration and exposed (e.g., relatively accessible to the user) when the arm support linkage is in the unfolded configuration. Since the user may be required to unfold the arm support linkage in order to expose the user interface device and enable the user to retrieve the docked user interface device, such a selectively hidden mount portion may, for example, encourage or remind the user to use the arm support linkage in its unfolded configuration when using the user interface device for control a robotic surgical system, thereby improving ergonomics, reducing user fatigue, etc.

As another example, as shown in FIGS. 14E and 14F, a docking station 1442 may be coupled to an armrest 1440. The docking station 1442 may be tucked into a recess in the armrest 1440 or otherwise collapse when the user interface devices are not in use (FIG. 14E), and then slide out of the recess in the armrest 1440 or otherwise extend when the user interface devices are used during a procedure (FIG. 14F). Additionally or alternatively, the user interface devices may be removable from the docking station. For example, as shown in FIG. 14G, a user interface device 1450 may be lifted from a resting place (e.g., in a recess 1446 in the docking station 1442) to be independently handheld by the user. Any wires connected to the user interface device 1450 may pass through channel 1444 in order to completely remove the user interface device 1450 from the docking station 1442. When the user interface device is not in use (e.g., after the surgical procedure is complete or during a break in the procedure), the user interface device 1450 may be returned to its resting place. The docking station 1442 or other device holder may include sensors (e.g., pressure sensor, conductive sensor) to detect when the user has set down one or more controls, where the user console may use the readout of these sensors to change the operating state of the robotic system or user console. The docking station or other device holder may also include electrodes, an induction coil, or other power charging device for charging the user interface devices when placed on the holder, if needed. In other variations, the docking station or other mount may additionally or alternatively be used to hold other devices, such as user's cellphone or portable music player.

Figure 15A:
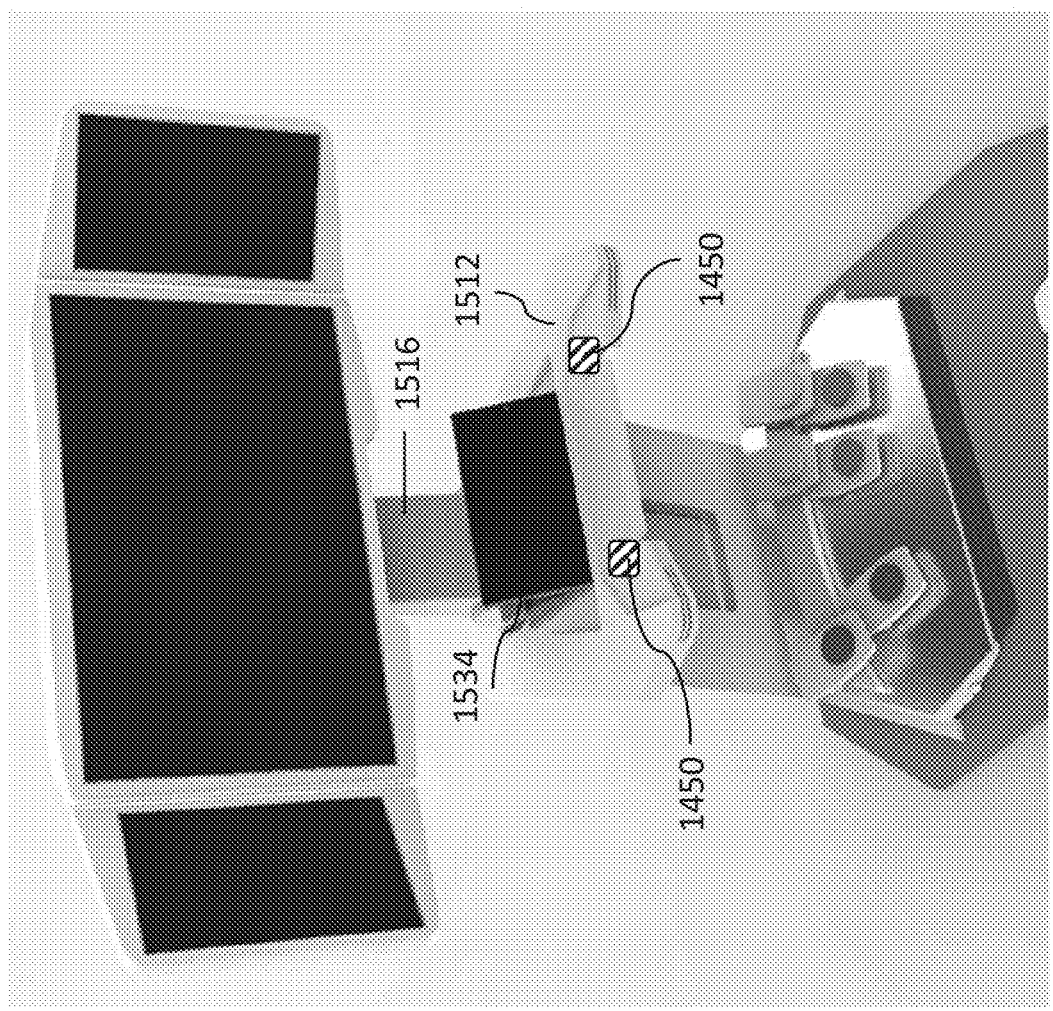
FIG. 15A is a perspective view of an exemplary user console.

As another example, as shown in FIGS. 15A and 15B, a docking station 1512 may be coupled to a display support 1516 (such as those described further below). The docking station 1512 may, for example, include a tray extending toward the seating assembly. Like the docking station 1442, the docking station 1512 may include resting places for the user interface devices 1450. The docking station 1512 may be adjustable, such as by being able to extend toward the seat assembly, rotate around the display support 1516, tilt left and right laterally, tilt anteriorly-posteriorly, etc. Additionally, the docking station 1512 may fold up, such as for storage purposes or to increase workspace of a user manipulating the user interface devices in space.

In other variations, the controls may include one or more foot-operated controls for controlling the robotic surgical instrument and/or controlling the user console. For example, a foot-operated control may be used to control an end effector (e.g., pinching, grasping, cutting, etc.) on the end of a robotic arm. As another example, a foot-operated control may be used to control part of the user console, such as for adjusting the position and/or orientation of the seat assembly (e.g., transitioning between a seated configuration, a reclined configuration, an elevated configuration, and/or other seat configurations), armrests, headrests, display assembly, immersive display assembly, etc.

One variation of foot-operated controls includes a pedal assembly. The pedal assembly may be generally located in front of the seat assembly such that the foot-operated controls are accessible by the feet of the user when the user is seated in the seat assembly. The pedal assembly may have a variety of configurations, with any suitable foot-operated controls.

As shown in FIG. 16, a pedal assembly may include a pedal tray 1610 and one or more pedals 1620 coupled to the pedal tray 1610. The number, style, and/or organization of pedals 1620 may be based on functional type (e.g., for controlling an end effector, for controlling or adjusting the user console, etc.). In other examples, the pedal assembly may additionally or alternatively include other foot-operated controls such as foot switches, touchpads, force plates, joysticks and/or other control mechanisms. Some of the foot-operated controls may include force feedback as a form of haptic feedback. Some of the foot-operated controls may be disabled for certain kinds of surgical procedures, depending on the need for certain kinds of controls. The pedal tray 1610 may be configured to be adjustable manually and/or automatically by motor in the anterior/posterior direction and/or vertically, and/or also to have an adjustable angle. For example, a pedal tray 1610 may include a pedal plate 1612 that is configured to move angularly relative to the bottom of the pedal tray.

In other examples, the pedal assembly may comprise two or more separate adjustable pedal trays, one for each foot, or for each foot control mechanism. Alternatively, each foot control mechanism may be adjustable relative to its pedal tray. In addition to adjustment of the pedal location in the anterior/posterior direction and the pedal tilt angle, other adjustments that may be configured include pedal resistance (s) globally through an entire movement range or subrange of movement, and the radial orientation of the pedal tray or foot control mechanism. The adjustment of the radial orientation may reduce foot or leg fatigue in the user by accommodating any natural internal or external rotation of the user's leg, as well as any supination or pronation bias in the foot. Furthermore, as shown in FIG. 2G, the pedal assembly 252 may fold down (or recede into a recess in the base, etc.), so as to facilitate storage or transportation of the user console in a compact configuration.

The pedal assembly may be mounted to or otherwise coupled to other components of the user console, or may be separate and independent or otherwise modular from other components of the user console. For example, as shown in FIGS. 2A-2F, the pedal assembly 212 may be mounted to an anterior portion of base 202.

In other variations, the user console may additionally or alternatively include other controls for remotely controlling a robotic system or instrument and/or a user interface, such as one or more keyboards, mice, trackballs, voice control, headtracking, gesture tracking, eye tracking (e.g., with sensors located on or near a display monitor such as an open display and/or immersive display as described below, which are configured to track motions of the head, hands, eyes, etc.) and the like. Other mechanisms, such as actuated springs, vibration motors, etc. may additionally or alternatively be provided to provide haptic feedback to the user.

Displays

The user console may further include one or more displays for providing and/or receiving information from a user. For example, at least one display may be configured to receive real time or near real time surgical information. For example, the display may receive and show video feed from a camera instrument inserted in a body cavity of the patient, where the camera instrument may provide a field of view of the surgical site, such as during a surgical procedure utilizing end effectors controlled via the user console. Additionally, the display may enable (e.g., via eye tracking, headtracking, gesture tracking, etc.) control of the robotic a robotic instrument and/or controlling other aspects of the system, such as for operating a robotic arm, operating an end effector attached to an end of a robotic arm, operating the user console for adjustments, operating or navigating a graphical user interface, etc. Furthermore, the display may be connectable to other auxiliary devices, such as a user's cellphone or portable music player, such that the user may interact with the auxiliary device through the display.

In some variations, the one or more displays in the user console may be configured to display surgical and/or other medical information (e.g., patient vitals, medical records, real-time information such as endoscopic images, etc.), enable communication via other medical personnel in the room or remote third parties, etc.

Open Display

In some variations, the display includes an open display (e.g., monitor display or screen). For example, as shown in FIGS. 2A-2F, a display assembly 208 includes a display pillar or support 226, a display mount 228, and one or more open display panels 230 which may be attached directly to the display mount 228 or via a display shell or frame 232. The display panels 230 may have any of a variety of resolutions (e.g. WXGA, SXGA, SXGA+, WXGA+, WUXGA, QWXGA, QXGA, QHD, QSXGA, QXGA+, 4K UHD, DCI 4K, HXGA, WHXGA, HSXGA, WHSXGA) and refresh rates (e.g., 24 Hz, 30 Hz, 50 Hz, 60 Hz, 120 Hz, 240 Hz), and may have a horizontal or vertical orientation. In the particular arrangement depicted in FIG. 2A, the display assembly 208 comprises a central horizontal display panel, and a vertical display panel to each side of the central display panel, which are mounted on display shell 232. In some variations, one or more of the panels 230 may be configured for 3D viewing. 3D viewing may be configured for viewing using active shutter glasses or passive polarizing lens (e.g., to provide passive 3D views without the need for specialized glasses). In other variations, one or more panels may comprise an autostereoscopic lenticular technology that does not require use of eyewear. An open monitor display may be dual-faced in that a front side may face a user in the seat assembly, while a back side may face the rest of the room to enable other surgical personnel to observe a video feed simultaneously with the user feed on the front side of the display. In some examples comprising a pedal tray, such as that shown in FIGS. 9-11, the display support may be a double pillar design with sufficient space between the pillars to accommodate the pedal tray being adjusted in translation, which may provide a larger movement range for the pedal tray in the anterior direction, and/or allow the user's legs to extend between the pillars (e.g., for a tall user, or when the seat assembly is in the reclined configuration as described in further details below).

Figure 18C:
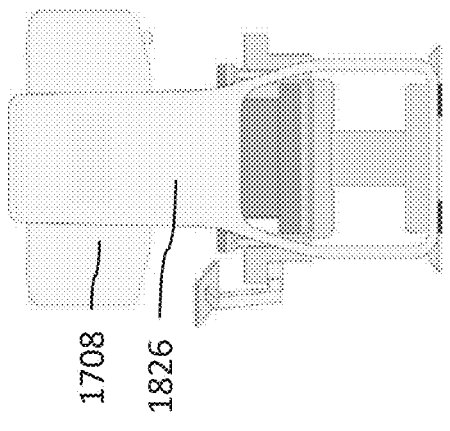
FIGS. 18A through 18E depict anterior views of variations of the user console.
Figure 18B:
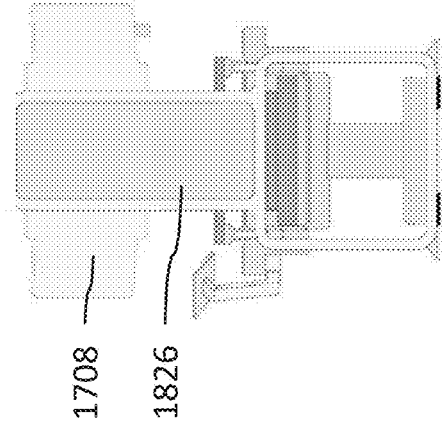
Figure 18A:
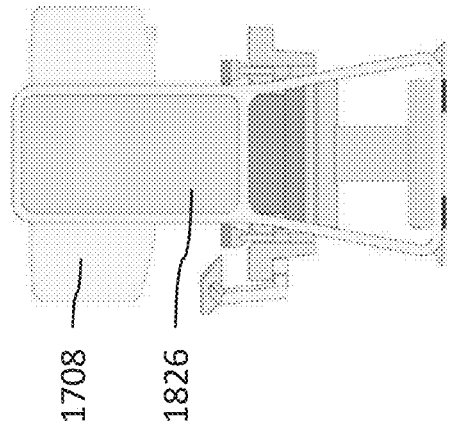
Figure 18E:
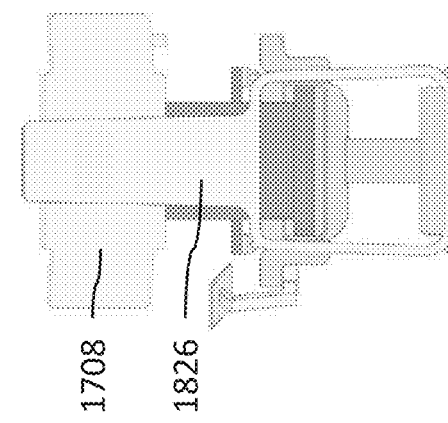
Figure 18D:
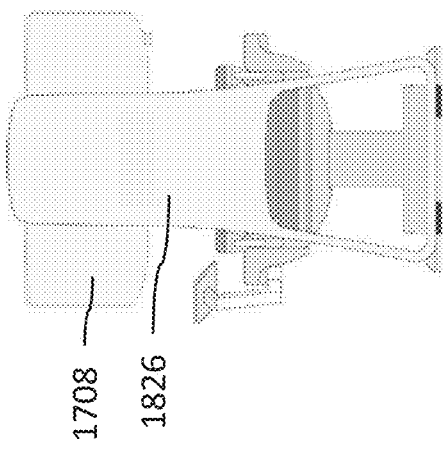

FIGS. 17A-17E depict variations of a display 1708, and FIGS. 18A-18E depict variations of a display support 1826. These variations are similar in that the display 1708 may be a three-panel display (or more panels) including a main central panel and two side panels, where the display is supported by a display support 1826 with double pillars or members. The main panel may have a horizontal orientation and the two side panels may have a vertical orientation, but in other examples, each panel may be configured as a horizontal or vertical display, and/or each panel may be rotated as needed. The display 1708 may additionally or alternatively be configured to rotate or pivot with all three panels together (e.g., for reducing glare). However, the display 1708 may alternatively include any suitable number of panels (one, two, four, etc.). The shape of the display support 1826, for example with respect to the display support pillars, may vary. For example, as shown in FIG. 18A, the display support 1826 may include a generally trapezoidal opening formed by a wider base, linearly tapering pillars, and a narrower superior portion. As shown in FIG. 18B, the display support 1826 may include a generally square or rectangular opening formed at least in part by a base and two vertical support pillars. As shown in FIG. 18C, the display support 1826 may include another generally polygonal opening formed at least in part by support pillars having a vertical portion and a linear tapering portion. As shown in FIG. 18D, the display support 1826 may be similar to that shown in FIG. 18A in that they both define generally trapezoidal openings between the display pillar supports, except that FIG. 18D depicts an opening between support pillars that has a curvilinear, rounded convex upper perimeter. FIG. 18E depicts a display support 1826 similar to that shown in FIG. 18B, except that in FIG. 18E the superior portion to which display 1708 mounts is narrower than that in FIG. 18B.

In yet other variations, the display may be independent of the user console. For example, the display may be wall-mounted or placed on a tabletop, surgical cart, etc.

The display assembly 208 may be configured for one or more adjustments. For example, the display support 228 may be configured to be adjustable in the anterior/posterior direction, so that the user can set the desired viewing distance from the seat assembly 204. To facilitate this movement, the display assembly 208 may have one or more wheels, low-friction sliders, or rollers 246 on its lower surface. The display assembly 208 may also be configured to vertical position adjustment along the longitudinal axis of the display support 228, at the interface between the display support 226 and the display mount 228 or the display shell 232. The display panels 230 or display shell 232 may also be configured to pivot laterally and/or tilt upward or downward. Like the seat assembly 204, the display assembly 208 may be adjusted manually and/or by motorized control via dedicated control devices or via the open display 230, secondary display 234 and/or immersive display 236 (described below). In some variations, the longitudinal movement path may not be a linear track. For example, as shown in FIG. 2C, the lower portion 248 of the display support 226 may be tilted toward the user, while the upper portion 250 is more vertical. This configuration tilts the display toward the user at lower display heights, while providing a neutral vertical display angle at upper display heights. This non-linear movement track may be provided in lieu of, or in addition to, any independent tilting mechanism provided between display mount 228 and the display support 226. Adjustments of the display assembly may be independent of and/or correlated to adjustments of the seat assembly (e.g., the display assembly may automatically tilt to accommodate or track a tilting of the seat assembly).

Immersive Display

In some variations, the user console may additionally or alternatively include an immersive display, such as a periscope or other head mounted display placed in contact with the user's face or head. As shown in FIGS. 3A and 3B for example, an immersive display 360 may be coupled to the seat assembly 310 via an immersive display support arm 362 that positions the immersive display 360 in front of the face of a user located in the seat assembly 310, such that the user may directly view content in the immersive display 360 in an immersive manner (e.g., comfortably and ergonomically immerses the user into the display environment with reduced distractions from the user's peripheral field of view). The immersive display may display various information associated with the surgical procedure (e.g., endoscopic camera view of the surgical site, static images, GUIs, etc.) and/or robotic surgical system (e.g., status, system settings), and/or other suitable information in the form of 2D and 3D video, images, text, graphical interfaces, warnings, controls, indicator lights, etc. Unlike other immersive and virtual reality head-mounted devices, which rely entirely on motion of the head-mounted display to change the view of within the display and thus restrict the ability of head movements to control other instruments, the immersive display may enable the user to interact with displayed content using head gestures and other head/eye movements for control of the immersive display and operation of other instruments such as those in the robotic surgical system.

The immersive display may be a virtual reality display or an augmented reality display (e.g., to show the operating room to the surgeon without requiring removal or disengagement from the immersive display, to show the surgeon with tracked icons where the surgical instruments have been at the surgical site), or capable of either configuration. The immersive display may be included in addition to a monitor, or either the monitor or the immersive display may be omitted from the user console. In variations in which both the open display/monitor and the immersive display are included in the user console, the immersive display may include an opening or transparent window that selectively permits "see-through" viewing of the open display (e.g., with a shutter that toggles between enabling view of the immersive display and view of the open display). Alternatively, the system may output any image or video signal to a generic display.

Figure 19A:
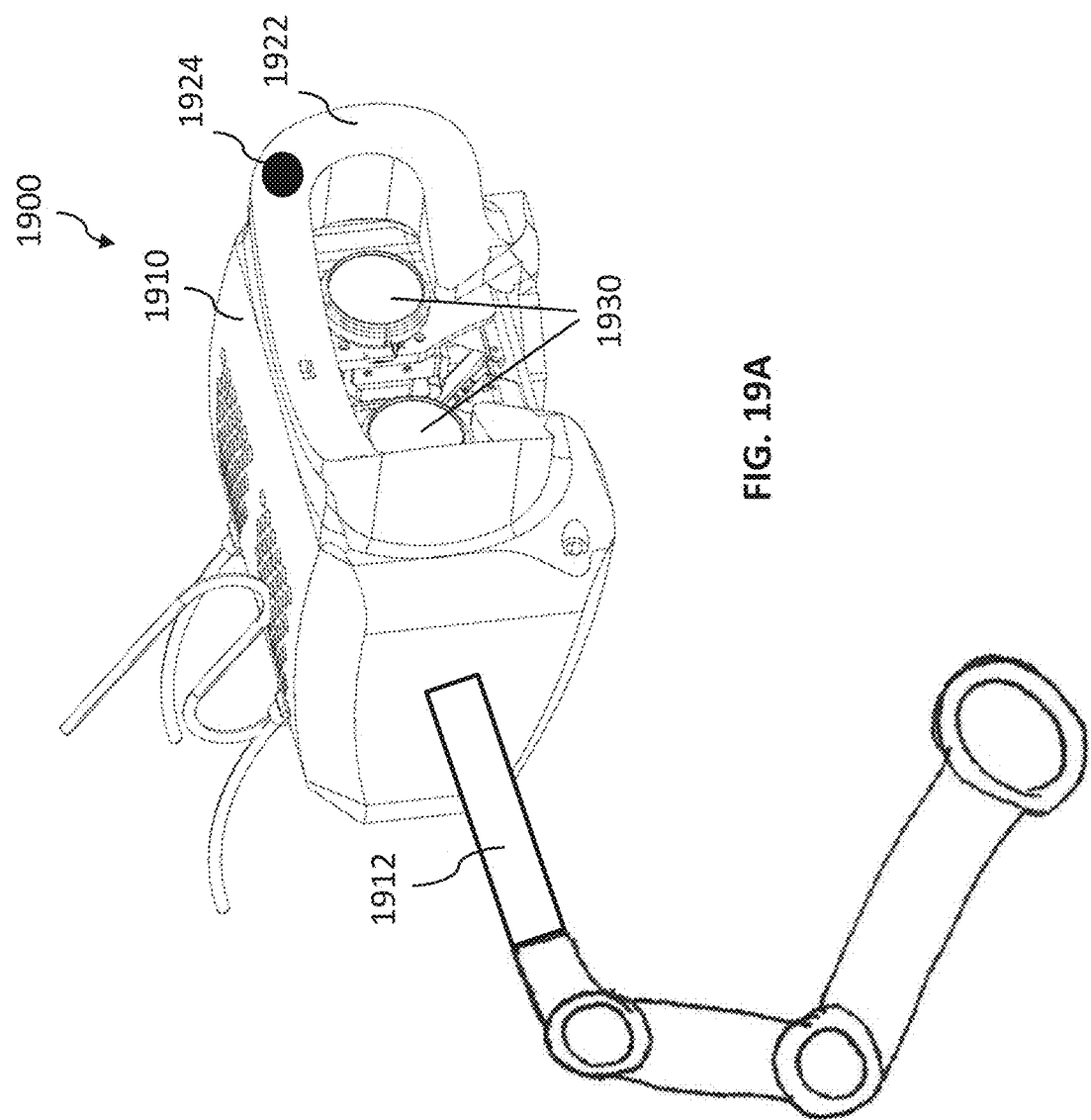
FIG. 19A shows an exemplary immersive display in one exemplary user console.

Generally, in some variations, as shown in FIG. 19A, an immersive display 1900 may include a housing 1910 mounted to a support arm 1912 and configured to engage with a face of a user, at least one eyepiece (e.g., at least two eyepiece assemblies 1930 disposed in the housing and configured to provide a three-dimensional display), and at least one sensor (e.g., represented by sensor 1924 on a face frame 1922 configured to engage or be proximate to the face of the user). The sensor may, in some variations, enable operation of the robotic surgical system upon detection of a certain parameter (e.g., presence or absence of a user engaged with the immersive display 1900, sufficient alignment of the user relative to the eyepiece assemblies 1930, identification of the user as an authorized user of the robotic surgical system, etc.), etc. The support arm 1912 may be configured to bring the housing in position proximate to the user's face or head, and may be actuatable, such as for positioning, orienting, or otherwise moving the housing 1910 for ergonomic purposes. Additionally or alternatively, straps or similar attachment devices may be coupled to the immersive display to secure and/or align the housing 1910 to the user's face and/or head.

The one or more eyepieces can, for example, include a binocular view that may facilitate stereoscopic or 3D displays, etc., though in other examples an eyepiece may include a monocular view. The immersive display may include lenses to provide built-in vision correction for users who are near-sighted, far-sighted, astigmatic, etc. Sensors in the immersive display may provide eye-tracking for instrument controls, user identification, etc.

In some variations, the immersive display support arm may be mounted on a side of the seat back of the seat assembly and configured to approach the user from the side of the user console to facilitate user access to the immersive display. For example, as shown in FIGS. 2C and 2D, a proximal end of the immersive display support arm 240 may be coupled to a right side of the seat back, though alternatively the proximal end of the display support arm 240 may be coupled to a left side of the seat back (e.g., at about the height of the head rest 224, though not necessarily). The proximal end of the immersive display support arm 240 may be configured to adjust vertically and/or rotationally, etc. Furthermore, as shown in FIG. 2G, the immersive display arm 240 may be configured to fold or collapse against the side of the seat assembly (or other mounting location of the arm 240), so as to enable user access to the seat and/or facilitate storage or transport of the user console in a compact configuration.

In other variations, a proximal end of the immersive display support arm may be fixedly coupled to a midline (or near midline) of the seat back and configured to approach the user from the side of the user console to facilitate user access to the immersive display. For example, as shown in FIGS. 9-11, a proximal end of the immersive display support arm may be mounted (e.g., via fasteners, welded joint, mechanical locks, etc.) to a posterior surface of the seat back. As another example, a proximal end of the immersive display support arm may be adjustably coupled to a posterior surface of the seat back, such as with a prismatic or other joint that enables the immersive display support arm to adjust vertically, laterally and/or rotationally relative to the seat back. For example, FIGS. 17A, 17B, and 17E depict a vertical sliding interface or prismatic joint between a recess 1750 of the seat back and a slider 1742 or other element on the proximal end of immersive display support arm 1740. This sliding interface helps enable the immersive display support arm to adjust vertically. FIGS. 17C and 17D depict a similar vertical sliding interface, except that the recess 1750 is narrower in FIGS. 17C and 17D than in FIGS. 17A, 17B, and 17E.

Figure 19C:
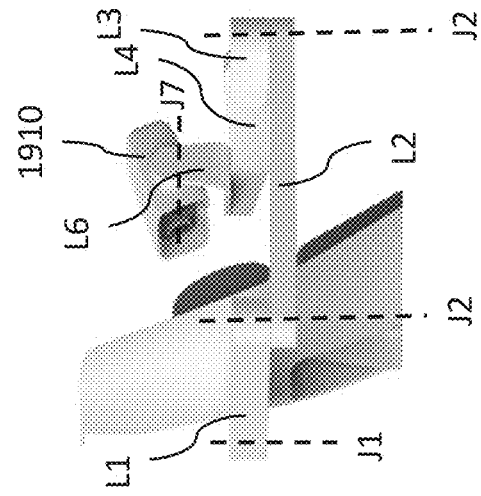
FIGS. 19B and 19C illustrate an articulated support arm for the immersive display shown in FIG. 19A.
Figure 19B:
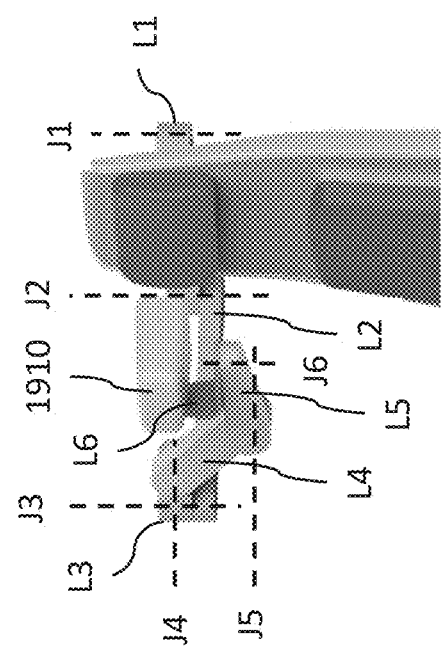
Figure 19D:
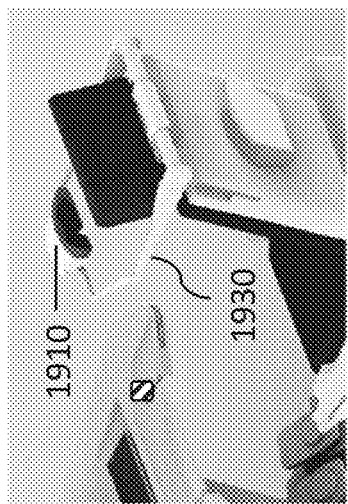
FIGS. 19D through 19F illustrate another exemplary support arm for an immersive display.
Figure 19E:
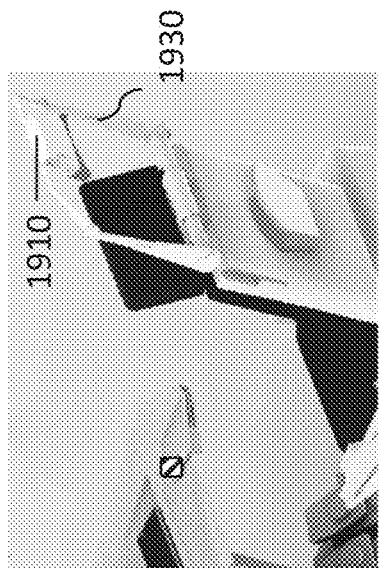
Figure 19F:
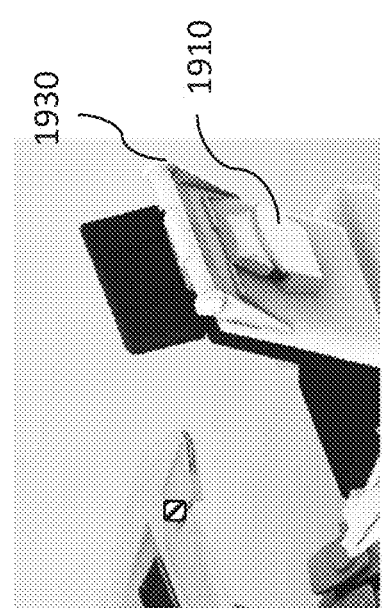

In yet other variations, as shown in FIGS. 19B-19C, the immersive display may be coupled to the seat back with an overhead assembly including one or more support arms in a support frame 1930. The support frame 1930 may be configured to approach the user from over the user's head as shown in FIG. 19D. As shown in FIG. 19E, the support frame 1930 may swing overhead to behind the headrest or other portion of the seat back, and may fold down against the seat back (e.g., FIG. 19F) or collapse or recede into a cavity in the seat back, such as for storage purposes.

The immersive display support arm may be articulated such that it is capable of moving with multiple degrees of freedom. For example, in one variation shown in FIG. 19B, an articulated immersive display support arm may include at least six degrees of freedom. In this paragraph, "horizontal" is meant in reference to being generally orthogonal to the seat back, while "vertical" is meant in reference to being generally parallel to the seat back. The support arm may include a proximal mount (e.g., similar to slider 1742 shown in FIG. 17A) coupled by a first rotational joint J1, such as a pin or fork joint, to a first link L1, where the first rotational joint J1 is rotatable around a vertical joint axis to provide movement in a horizontal plane. The first link L1 is coupled by a second rotational joint J2 to a second link L2, and second link L2 is coupled by a third rotational joint J3 to a third link J3. The first, second and third rotational joints J1, J2, and J3 are oriented along respective vertical rotation axes, and can permit adjustment of the immersive display without significant restriction at a desired location generally in a horizontal plane around the headrest region.

Further configurational flexibility may be provided by the third link L3 being coupled by a fourth rotational joint J4 to a fourth link L4, where the fourth rotational joint J4 is rotatable around a horizontal axis to provide movement in a vertical plane. The fourth link L4 may be further coupled by a fifth rotational joint J5 to a fifth link L5, where the fifth rotational joint J5 is rotatable around a horizontal axis to provide movement in a vertical plane. Furthermore, fifth link L5 may be coupled by a sixth rotational joint J6 to a sixth link or bracket member L6, where the sixth rotational joint J6 is rotatable around a vertical axis to provide movement in a horizontal plane. The fourth, fifth, and sixth rotational joints J4, J5, and J7 may generally permit vertical height adjustment of the immersive display such that in combination with the first, second, and third rotational joints J1, J2, and J3, all six rotational joints may help enable adjustments in various combinations of angular position changes in three-dimensional space (e.g., translation in X-Y-Z, rotation in yaw, roll, and pitch directions). The immersive display arm 1920 may, as the result of multiple articulated joints having a suitable number of degrees of freedom may, for example, enable arm rotation, arm extension/retraction, arm forward/backward tilting, etc.

As shown in FIG. 19C, an immersive display housing 1910 may be mounted to bracket member L6 by a seventh rotational joint J7, where the seventh rotational joint J7 is rotatable around a horizontal axis so as to allow a seventh degree of freedom for pivotable adjustment in a vertical plane (e.g., angling up or down).

Some or all of the joints, such as the fourth and fifth joints J4 and J5, may include friction brakes, active brakes, clutch, and/or other actuatable locking mechanisms to help lock the immersive display support arm into a particular configuration. Locking the immersive display support arm in place may, for example, help counter gravitational effects that might cause the immersive display housing 1910 and/or the immersive display support arm 1920 to collapse downward (e.g., onto the user, if the seat assembly is in a reclined configuration). Additionally or alternatively, some or all of the joints may be counterbalanced in order to prevent downward collapse when unsupported externally by a user, etc.

Manipulations of the pose (i.e., position and orientation of the arm) may be manually controlled and/or controlled with an actuator, and may be automatically controlled as with other aspects of the user console described herein. Some movements of the arm may be automatic (e.g., collapse or extension) in response to a trigger, such as determination of a user present in the seat assembly based on a user login or sensing a threshold weight in the seat assembly. Manual adjustments of the arm may involve disengaging a clutch (e.g., with a touch sensor, button, handle, etc.) that is configured to resist movement of the arm.

Figure 25B:
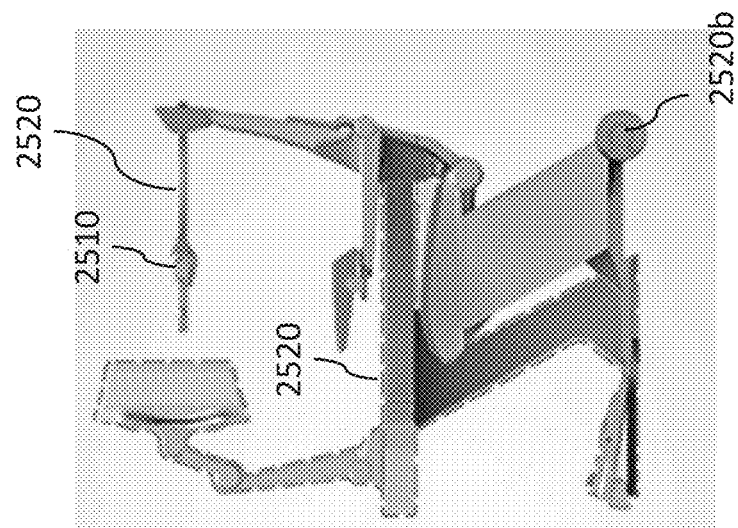
FIGS. 25A and 25B are side orthogonal views of an exemplary user console with wheels on a seat assembly.
Figure 25A:
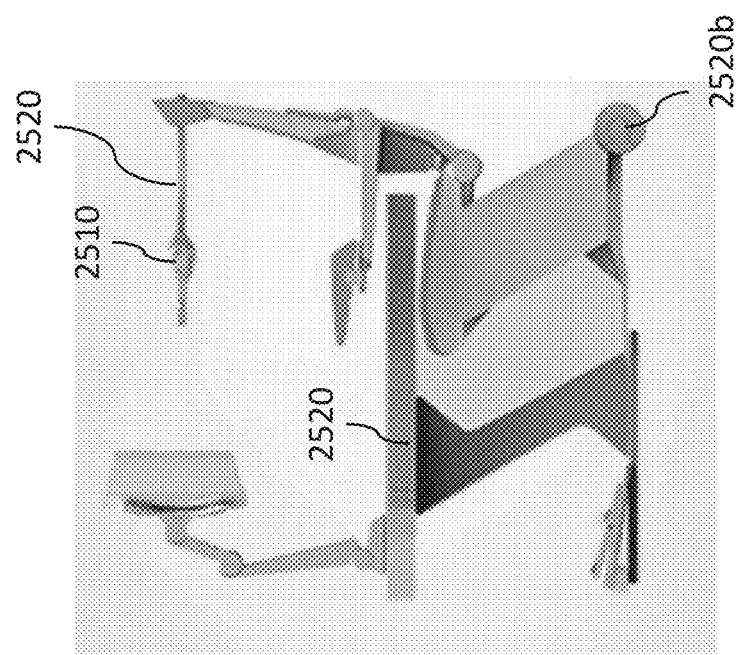
Figure 26A:
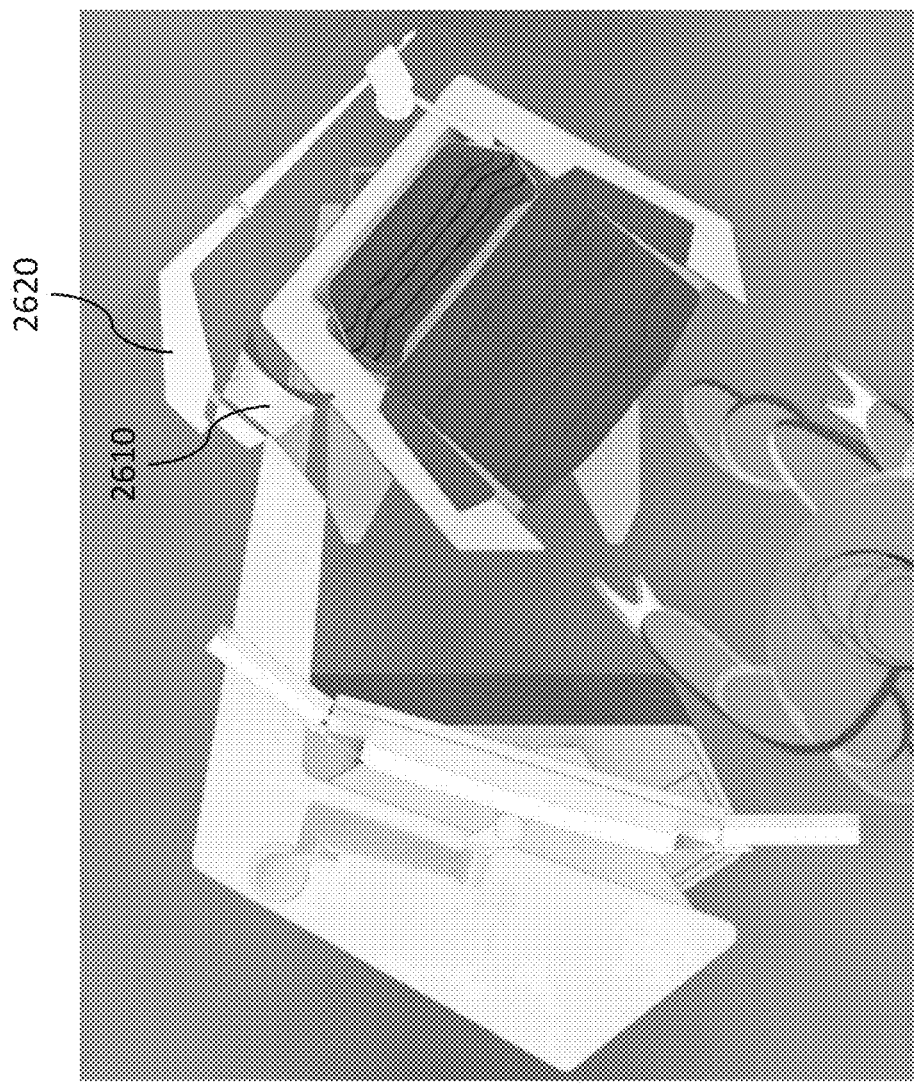
FIG. 26A is a top view of an exemplary user console with a side entry and pivoting seat assembly.
Figure 26B:
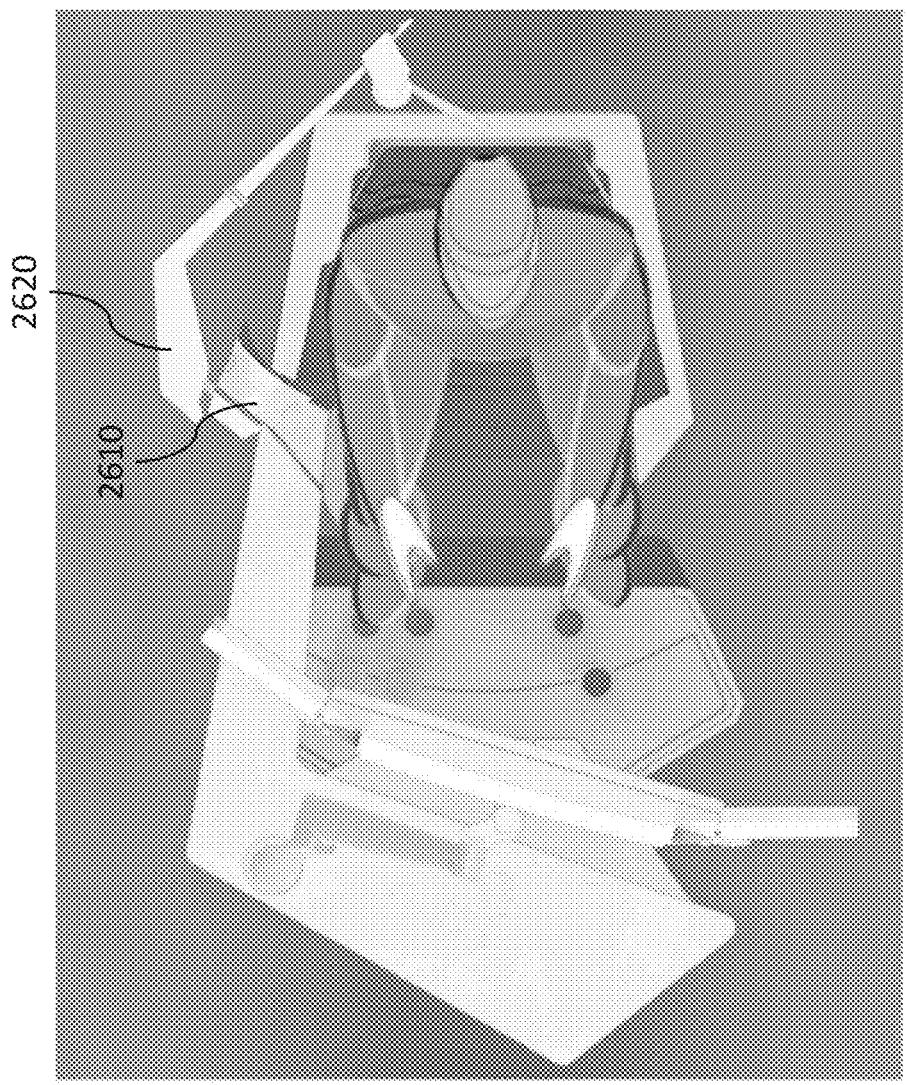
FIG. 26B is a top view of the exemplary user console shown in FIG. 26A, with a user engaged in the user console of FIG. 26A.
Figure 26C:
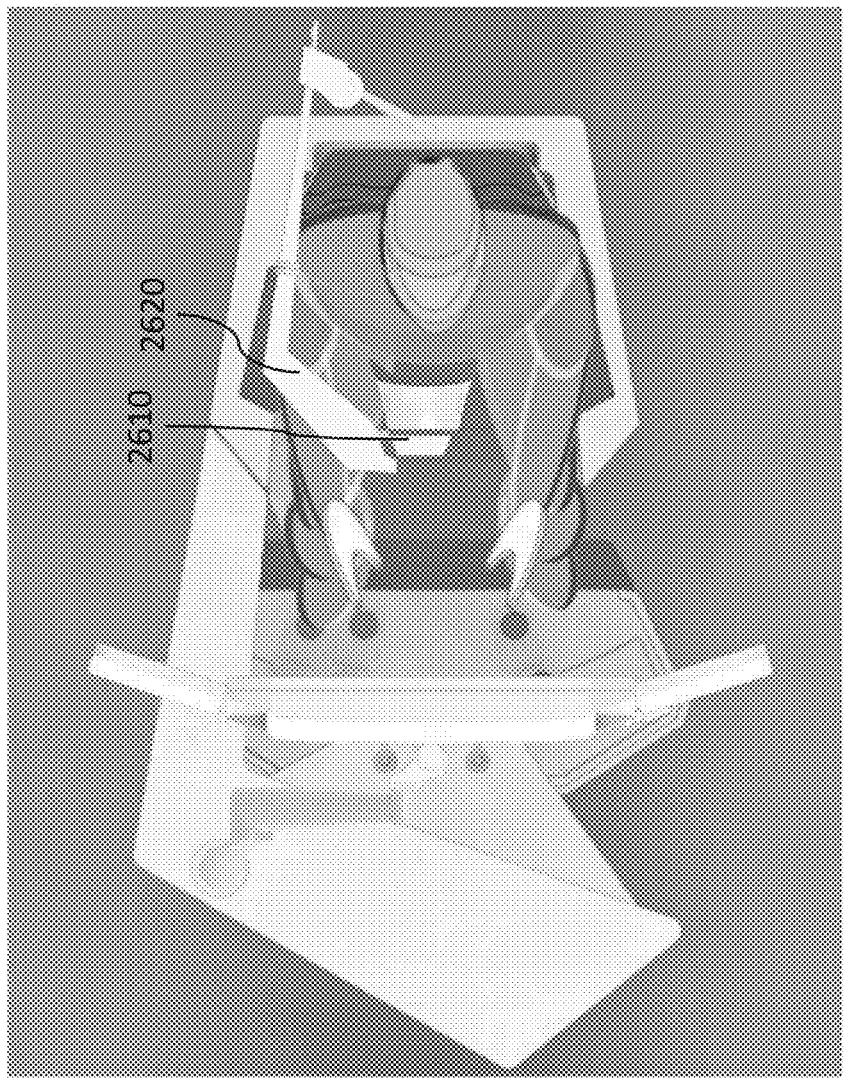
FIG. 26C is a top view of the exemplary user console shown in FIG. 26A, with an immersive display oriented and engaged with a user.

In other variations, the immersive display support arm may be one substantially static member. For example, as shown in FIGS. 25A and 25B, the display support arm 2520 may act as a cantilever arm to suspend the immersive display 2510 generally in front of the seat assembly. In yet other variations, the display support arm may include a member that swings laterally toward and away from a user in the seat assembly. For example, as shown in FIGS. 26A and 26B, before a user sits in the seat assembly and while the user is in the seat assembly but not utilizing the immersive display 2610, the display support arm 2620 may swing laterally outward in an "out" position to keep the immersive display 2610 away from the face and head of the user. When the user is ready to view through the immersive display 2610, as shown in FIG. 26C, the display support arm 2620 may then swing laterally inward in an "in" position to keep the immersive display 2610 proximate to the face and head of the user.

In some variations, the eyepiece and/or immersive display support arm may include one or more sensors to aid in collision avoidance. For example, at least one proximity sensor (e.g., ultrasound, laser, etc.) may be located in at least a portion of the eyepiece and/or immersive display support arm in order to detect potential collisions with the seat assembly (e.g., seat back, armrest, headrest), display monitor, the user's face or other body part, etc. Upon the detection of a potential collision, the user console may emit a warning, such as an audio tone, visual signal, tactile feedback through the seat assembly or user interface devices, etc., and/or the user console may automatically actuate the immersive display support to remain in a "hold" position or move in an opposite direction so as to avoid collision between the immersive display support arm and another object. The proximity sensor or sensors may additionally or alternatively be used to provide a comfortable engagement with the user's face through a dampened or slowed "soft landing" effect as the eyepiece and the user's face approach each other for engagement.

Auxiliary Display

The user console may further include a secondary or auxiliary open display. For example, a secondary open display 234 may be attached to the side of the seat shell 216 of the seat assembly 204 with a support arm 238, as shown in FIGS. 2A to 2F, but in other examples, one or more secondary open display may be coupled to the seat pan, the seat back, the headrest, the armrest, the seat support, the base, and/or the display support, mounted on the midline or side of these components. In another example, as shown in FIG. 15A, a secondary open display 1534 may be located on a user interface platform 1512. The secondary open display may be a touch screen device. In some variations, the display assembly may include adjustable mechanisms similar to those described above, which may provide, for example, secondary display panel vertical translation, secondary display panel lateral rotation, secondary display panel forward/backward tilting, etc.

The secondary open display 234 and the immersive display 236 may be configured to replicate one or more displays or controls on a main display panel 230, and/or may include other controls or images not provided on a main display panel 230, or each other. For example, the secondary open display may be configured to prompt a user for user identifier information (e.g., user ID, password, passcode, etc. Additionally or alternatively, the user console may include a microphone, camera, fingerprint sensor, etc. to facilitate receipt of other user identifiers, through processes such as voice recognition, face recognition, and other biometric recognition such as iris code or fingerprint.

Illustrative Variations

Figure 20A:
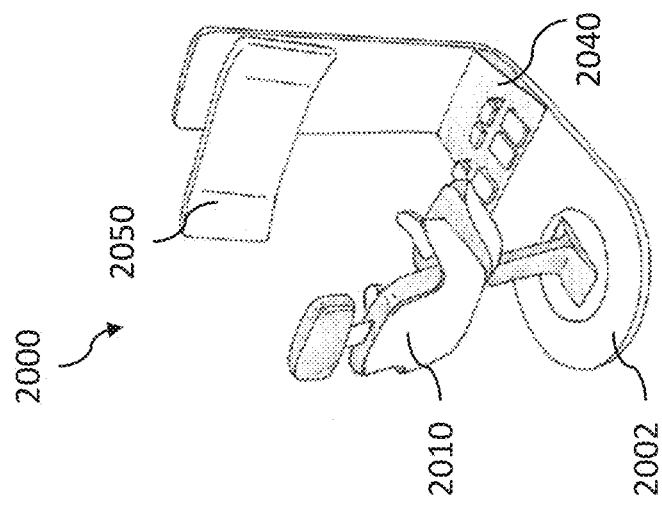
FIGS. 20A and 20B are front perspective and rear perspective views of an exemplary user console with a base having a front wall.
Figure 20B:
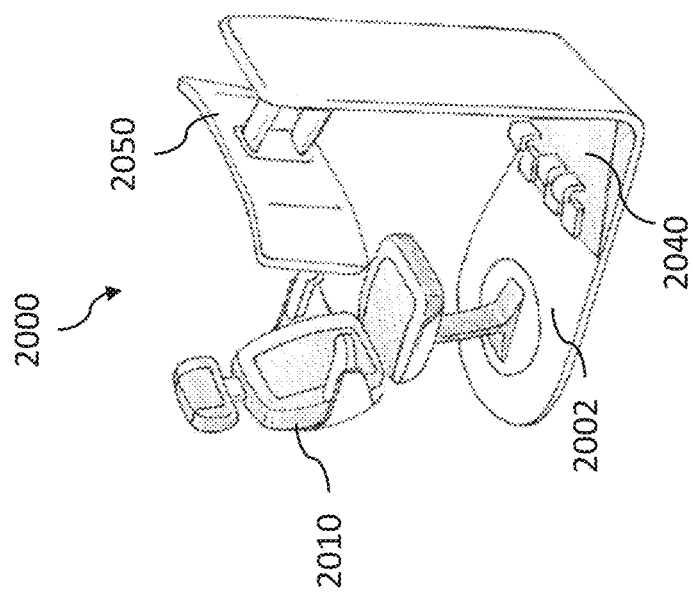

A user console may include any combination or subcombination of the above-described structures. In one embodiment, as shown in FIGS. 20A and 20B, a user console 2000 may include a base 2002 having a lower section and a front wall, a seat assembly 2010, a pedal assembly 2040 coupled to the lower section of the base, and a display 2050 coupled to the front wall of the base (instead of a separate display support mount, etc.), but no user interface devices or immersive display.

Figure 21B:
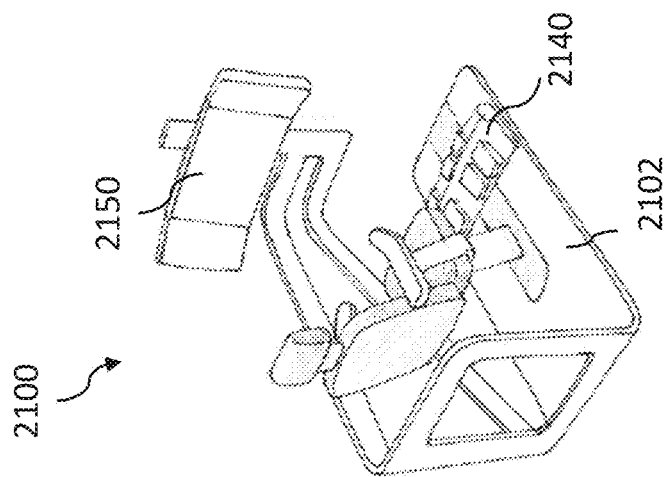
FIGS. 21A and 21B are front perspective and rear perspective views of an exemplary user console with a base having a side wraparound wall.
Figure 21A:
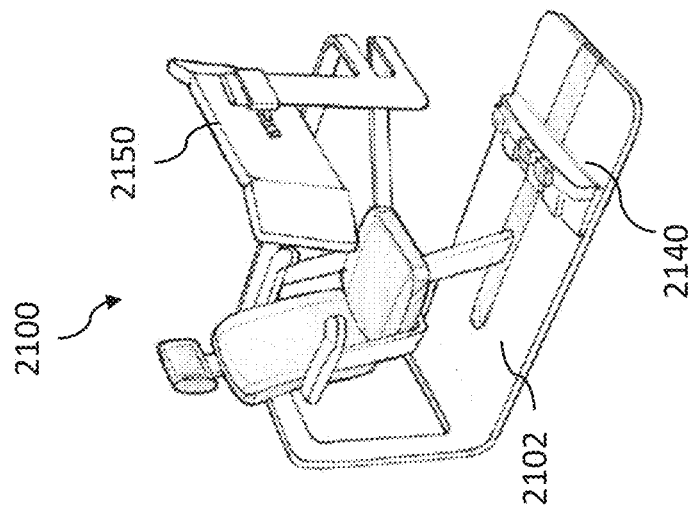

In another embodiment, as shown in FIGS. 21A and 21B, a user console 2100 may be similar to user console 2000 described above with respect to FIGS. 20A and 20B, except that the user console 2100 may include a base 2102 that has a lower section on which pedal assembly 2140 is located, a rear wall, and a side wraparound wall. The user console 2100 may, for example, facilitate a side entry based on the location of the wraparound wall. A display 2150 may be supported by the side wraparound wall portion of the base 2102.

Figure 22A:
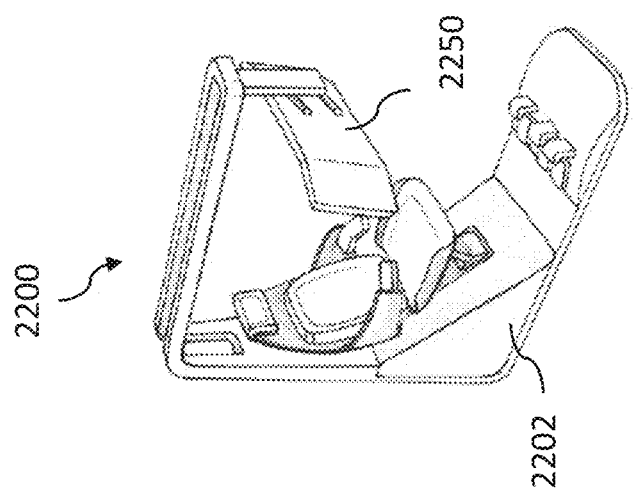
FIGS. 22A and 22B are front perspective and rear perspective views of an exemplary user console with a base having a rear wall and an overhand.
Figure 22B:
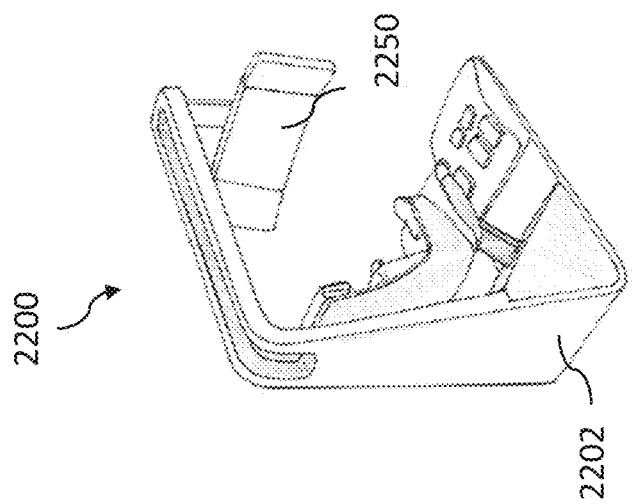

In another embodiment, as shown in FIGS. 22A and 22B, a user console 2200 is similar to user console 2100 described above with respect to FIGS. 21A and 21B, except that the user console 2200 may include a base 2202 that has an overhang extending over the seat assembly, where a display 2250 is configured to suspend from the overhang.

Figure 23B:
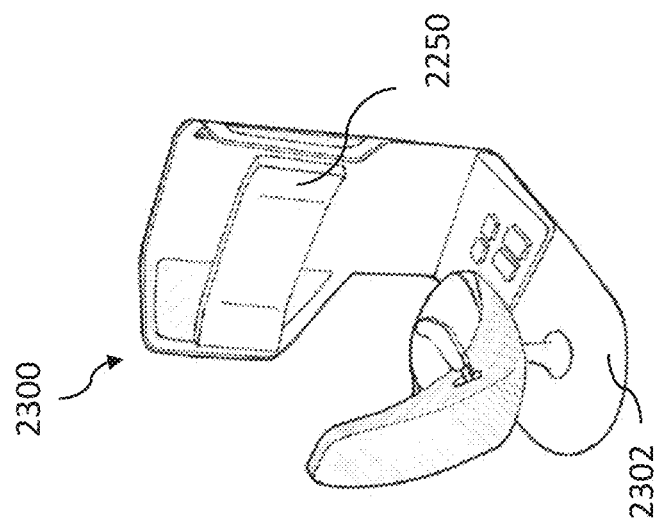
FIGS. 23A and 23B are front perspective and rear perspective views of an exemplary user console with a base having a front wall with side wings.
Figure 23A:
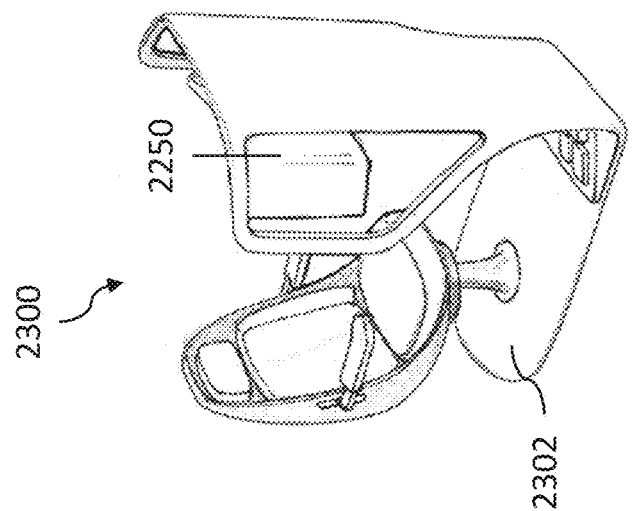

In the variation shown in FIGS. 23A and 23B, a user console 2300 is similar to the user console 2100 except that the front wall of the base 2302 also extends laterally to provide angled or curved wings around the display 2250. This may, for example, help reduce glare on the display 2250.

Figure 27A:
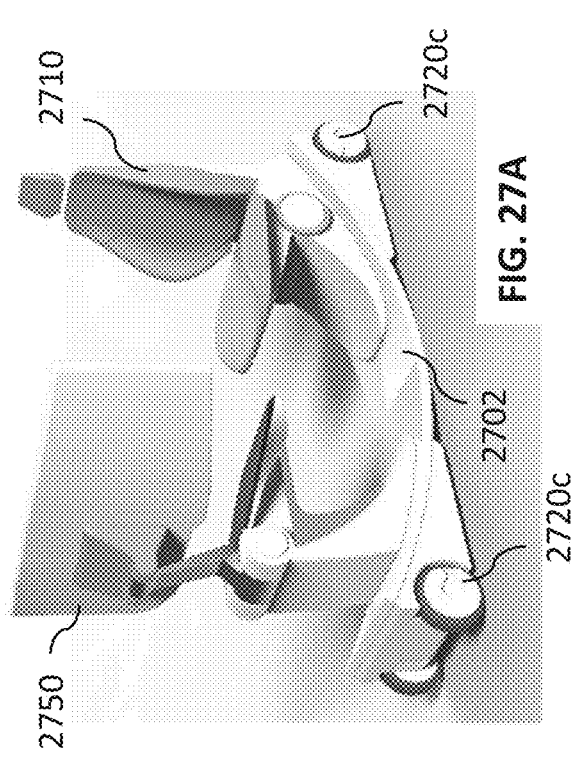
FIG. 27A is a front perspective view of an exemplary user console having a curved base with wheels.

As shown in FIGS. 24A and 24B, in some variations, one or more of the components may include wheels 2420. Different modular components may include wheels to facilitate relative movement among the different components. For example, a display support may include wheels 2420 to enable translation and/or rotation relative to the seat assembly and/or base. As another example the seat assembly may include wheels 2420b to enable translation and/or rotation relative to the display and/or base. Similarly, as shown in FIGS. 25A and 25B, the seat assembly may include one or more wheels 2520b to enable the seat assembly to adjust its position and orientation relative to a user interface platform 2520 (e.g., having a keyboard or other controls). As yet another example, as shown in FIGS. 27A-27B, the base 2702 may include wheels, so as to increase mobility (e.g., for moving the user console between different operating rooms, or repositioning the user console within a room). Additionally or alternatively, the pedal assembly, base, and/or other components of the user console may include one or more wheels. The wheels may include brakes (e.g., friction brakes) or other locking mechanisms to prevent movement or other subsequent unintentional repositioning of components.

User Console Configurations

To facilitate the adjustment and set-up of the user console for ergonomic and other adjustments, a configuration controller may be provided that can detect and save the specific configuration of one more components of the user console, including the seat assembly, display assembly, pedal assembly, and also control the motors of the adjustment mechanisms to restore the user console to a save specific configuration. Each configuration may be linked to one or more users, user characteristics, patient or patient characteristics (height, weight), operating teams, robot system configurations, seating preferences and/or one surgery types. The configuration controller may be separate from the robot controller of the robot system, with its own processor, memory, and input/output interface to the motors, interlocks, actuators and/or sensors, or may be part of the same system.

In use, the user console may be adjusted to a desired configuration, including ergonomic adjustments to the seat assembly, pedal assembly, and display assembly, but also customizations to the user interface and user interface devices, if available. The complete or a subset of the configuration may then be saved, and optionally linked to one identifiers or categories. The identifiers may be a user identifier, a non-user identifier category or characteristic, (e.g. surgery type, seating arrangement, etc.) and/or a biometric identifier (e.g., iris code, fingerprint, etc.). In subsequent usage, or more identifiers are entered, provided or selected simultaneously or serially, to narrow down to the saved configuration(s) for final selection or confirmation. The configuration controller then signals or controls the various motors to make any mechanical adjustments to the user console, and also reconfigures or sets the configuration of the user interface. This can occur while the user is seated in the user console or prior to seating, in order to reduce set-up time for a single user, or between multiple users who use the same user console in respective customized configurations during a single procedure, etc. Furthermore, in some variations, the user console may dynamically improve ergonomics by tracking motions of the user (e.g., body position, eye position, eye gaze, etc.) and, in response to the user's motions, automatically recommending or transitioning to an optimum configuration for the user's ergonomic, viewing, hardware, and/or other needs, such as for reducing fatigue or injury. For example, if configuration controller detects that the user in the seating assembly begins to strain upwards (as if trying to obtain a higher perspective of the operating table), the controller may automatically adjust the seating assembly to elevate the user.

In addition to any customized configuration, the configuration controller may include some pre-configured settings, or may include an algorithm that sets a configuration based upon the height and/or weight of the user as entered into the configuration controller, or measured by one or more sensors built into the user console (e.g. weight sensors in the seat pan, base and/or pedal assembly, optical height or length detection). In one example, the configuration controller may instruct the user to sit in the seat assembly with his or her feet placed on the pedals. Weight sensors in the seat pan and base may then adjust the seat height, seat angle, and/or pedal displacement in order to achieve a 50/50 weight distribution (e.g., between left and right sides of the user), or other weight distribution. In another example, the seat pan may comprise a weight sensor located in the center of the seat pan, and one or more weight sensors located about the anterior edge of the seat pan. The seat height and/or seat angle is then adjusted to achieve a desired weight distribution between the center force and the anterior edge force, which may reduce force concentration that may reduce lower leg circulation. In still another example, an optical or image sensor located on the display assembly may be used to detect the eye level of the user and adjust the display panel height. The desired height may be set so that the top of the display panel it at eye level, or 0 to 5 cm below the detected eye level, or where eye level is at a height located in the upper half of the display panel.

FIG. 4A illustrates an exemplary set of parameters that may, in some variations, be adjustable to configure the user console. The open display may be adjustable in several degrees of freedom ("DOF"). For example, open display height may be adjusted via vertical translation ("ODV") along a display support, anterior-posterior location of the open display may be adjusted via horizontal translation ("ODH") relative to a base of the user console, and open display tilt ("ODT") may be adjusted (e.g., relative to the display support).

Additionally or alternatively, the pedal tray may be adjustable in up to three or more DOF. For example, foot pedal tray tilt ("PT") may be adjusted (e.g., relative to the base of the user console), anterior-posterior location of the foot pedal tray may be adjusted via horizontal translation ("PH") relative to the base of the user console, and/or height of the foot pedal tray may be adjusted via vertical translation (not shown) such as with an adjustable riser coupled to the base of the user console.

The seat assembly may furthermore be adjustable in a variety of DOFs. For example, chair rotational position may be adjusted via chair swivel ("CS") around a vertical axis (e.g., by adjusting rotational swivel position of a seat support pillar as described herein), chair height ("CV") may be adjusted via translation along the seat support pillar, chair recline (generally shown as chair recline ("CR")) relative to a seat pan may be adjusted (e.g., as described in further detail herein), and seat pan tilt ("CBT") may be adjusted (e.g., as described in further detail herein). Additionally, headrest height ("HV") and/or headrest tilt ("HT") may be adjusted (e.g., as further described herein). Furthermore, the armrest height ("AV") and other arm rest configurations (e.g., lateral or planar motion, as described further herein) may be adjusted.

Furthermore, height of the base ("BV") relative to the ground may be adjusted, for example, as the result of deployment of wheels (as further described below) to transport and other suitable purposes. Adjustment of many of these and other parameters are described in further detail elsewhere herein.

FIGS. 4B-4D illustrate in more detail how the seat assembly may be configurable in one of a plurality of seating assembly configurations. A configuration may be based on a set of adjustable parameters (e.g., at least some or all of parameters A-F as shown in FIGS. 4B-4D). For example, adjustable parameter A is the angle of the user's lower leg relative to the user's thigh when the user is in the seat assembly, as the result of the relative orientation of the seat pan and the pedal assembly. Adjustable parameter B is the angle of the backrest relative to horizontal. Adjustable parameter C is the angle of the pedal assembly relative to horizontal (e.g., seat assembly base or ground). Adjustable parameter D is the angle of the armrest relative to horizontal. Adjustable angle E is the angle of the headrest relative to the backrest. Adjustable parameter F is the location of a lower end of the backrest relative to the seat pan or seat pan. In some variations, the seat assembly may be configurable in at least any one, and preferably two or three, of a seated configuration (e.g., FIG. 4B), a reclined configuration (e.g., FIG. 4C), and an elevated configuration (e.g., FIG. 4D).

In the exemplary seated configuration depicted in FIG. 2E, the seat pan 218 is in a generally horizontal orientation and the vertical height of seat assembly 204 is set so that the user's heels are in contact with the base 202 and with the lower legs in a forward position and the heels in contact with the base with the feet in a neutral, slightly plantarflex position. The pedal assembly 212 is positioned with respect to the base 202 so that the user's forefeet, but not the heels, are over the pedal assembly 212, with a forward angle 252 in the range of about 25 to 45 degrees. In other variations, the pedal assembly 212 may comprise a heel region or heel rest, and may be positioned under the forefoot and heel. The seat back 220 is in a vertical or slightly rearward angle, and the display assembly 208 is set such that the top edge of the display frame 232 is generally at eye level, and the display mount 228 is angled so that the display panels of the display frame 232 are orthogonal to the visual axis of the user, which is slightly below the horizontal of the eye level.

An exemplary elevated configuration is depicted in FIG. 2F. An elevated configuration may be helpful, for example, when the user desires to have a direct view into the procedure room or procedure table. Additionally, the elevated configuration may, for example, be suitable for sterile use, easy and fast entry and/or exit by the user from the user console (e.g., such that the user may "step in" or "step out" of the seating assembly in the elevated configuration). In this configuration, the seat pan 218 is anteverted, with its front edge angled downward, and also translated or retracted posteriorly, so as to reduce the area of the seat pan available to support the user's thighs (i.e., reduce the depth of the seat pan anterior to the seat back, as measured in the anterior-posterior direction) and such that less than or none of the user's thighs are supported by the seat pan 218, compared to the seated configuration in FIG. 2E, and allows the user's legs to be in a more vertical orientation. Additionally or alternatively, the area of seat support may be reduced in other manners, such as by translating the seat back anteriorly, at least partially folding and/or rolling up a posterior portion of the seat pan (e.g., in variations in which the seat pan is sectioned or flexible. It should be noted that such adjustments to the area of seat support may additionally or alternatively be used to accommodate and be customized to different user sizes. To further accommodate this relatively more vertical orientation, the pedal assembly 218 may be moved more posteriorly on the base 202 compared to the seated configuration, and the forward angle of the pedal assembly 218 may be flat or at least smaller than the forward angle in the seated configuration. The seat back 220 may be in the same or relatively more tilted forward orientation compared to the seated configuration. The display frame 232 may be raised to a higher position relative to the seated configuration. Also, with the particular posterior angled seat support 214 of this user console 200, when the seat shell 216 is elevated, there is also a posterior displacement of the user's position, and the display assembly 208 may also be moved posteriorly in the elevated configuration to maintain or at least partially compensate for changes in the user's eye-to-display panel distance. To facilitate movement of the display assembly 208, wheels 246 or low-friction sliding structures may be provided to facilitate the movements. In other variations, however, the display assembly 208 may be mounted in the base 202 and may not have exposed or visible wheels or sliders.

FIGS. 5A to 5C illustrate additional details regarding exemplary seated and elevated configurations, as well as an exemplary reclined configuration, as schematically illustrated with a user console 500 comprising a display panel 502, pedal assembly 504, seat pan 506, armrest 508, seatback 510, headrest 512 and immersive display 514.

In a seated configuration such as that shown in FIG. 5A, the seat pan 506 may be at a height wherein the user's heels are in contact with or generally about the base while the seat pan and the user's thighs are generally aligned, and horizontal or angled in the range of about −5 degrees to +5 degrees, about −5 degrees to about +10 degrees, or about −10 degrees to about +15 degrees to the horizontal plane. The pedal assembly 504 is positioned at an anterior-posterior position wherein the user's forefoot is in contact with the pedals, and angled about perpendicularly to the user's lower leg. The amount of the seat pan 506 protruding anteriorly from the plane of the seat back 510 may be in the range of about 75% to 100%, 80 to 100%, or 90% to 100% of the maximum anterior displacement of seat pan 506. Depending upon the user, the seat pan 506 may be customized to an extended position in the seated configuration to support at about 25% to 100% of the thigh distal to the user's gluteal fold, and in other examples, may be in the range of about 50% to about 95%, or about 70% to about 100%. The seat back 220 may be configured with an anterior angle in the range of about 80 degrees to about 110 degrees, about 90 degrees to about 105 degrees, about 90 degrees to about 100 degrees, or about 100 degrees to about 110 degrees. The pedal angle in the seated configuration may be in the range of about 15 to 45 degrees, about 20 to 40 degrees, or about 25 to about 35 degrees from the anterior horizontal plane 516, for example.

In an elevated configuration such as that shown in FIG. 5B, the seat pan 506 is elevated relative to the position in the seated configuration, and may also be anteverted or angled anteriorly to an angle of at least −5 degrees, −7 degrees, −10 degrees or −15 degrees, for example. The seat pan 506 may also be retracted relative to the seat back 510 such that about 10% to 75%, about 25% to about 60%, about 40% to 55%, or at least 10 cm, 20 cm or 30 cm of the seat pan 506 is posterior to the plane of the seat back 510. The seat back 510 may be configured with an anterior angle in the range of about 80 degrees to about 110 degrees, about 90 degrees to about 105 degrees, about 90 degrees to about 100 degrees, or about 100 degrees to about 110 degrees. The pedal angle 516 in the seated configuration may be in the range of about 0 to 30 degrees, about 0 to 15 degrees, or about 0 to about 7 degrees from the anterior horizontal plane. The height of the seat pan 506 may be set such that the heel of the user is in contact with the base, but in other variations may be configured such that the user's heels are above and not in contact with the base.

The horizontal distance of the display panel or display assembly in the seated or elevated configuration to be in the range of about 50 cm to 150 cm, 50 cm to about 125 cm, or about 50 to about 100 cm. In FIGS. 5A and 5B, where the seat support (not shown) is angled backwards such as in the exemplary user console 200 in FIGS. 2A to 2C, as the seat height is increased, as shown in FIG. 5B, the seat pan 506, and seat back 510 also are displaced posteriorly, and anteriorly when the seat assembly 518 is lowered. In this example, the display assembly 208 may be moved posteriorly or anteriorly by an equal distance of the horizontal displacement of the seat assembly 518, but in other examples, the display panel 502 may not be moved, or may be moved by a different amount than the horizontal displacement of the seat assembly 516. The height of the display panel(s) or display shell in the seated or elevated configuration may be set such that the top edge of the display panel(s) or display shell is at a relative height that is in the range of about +10 to −20 cm, +10 cm to −10 cm, about +5 cm to about −5 cm, about 0 cm to about −5 cm of the user's optical axis, depending on the size of the display. In other variations, the display height may be adjusted such that the user's optical axis is set to be aligned at about 125% to 50%, about 125% to about 75%, about 110% to about 90%, about 100% to about 90% relative to the bottom edge of the display (0%) and the top edge of the display (100%). The tilt angle of the display panel(s) or display shell may be adjusted in a linear or non-linear fashion to the tilt angle of the seat back 510. In some examples, the display tilt angle may be in the relative range of about 0 degrees to about 15 degrees lower than the angle of the seat back 220. In other examples, the display tilt angle from 90 degree axis may be offset by a proportion of the seat back tile angle deviation from a 105 degree axis, for example, from about 50% to about 100% of the angle change in the seat back 510.

In a reclined configuration such as that shown in FIG. 5C, the seat pan 506 is in a retroverted orientation along with the display panel 502. The degree of retroversion may be at least +5 degrees, +7 degrees, +10 degrees, +15 degrees, +20 degrees, +30 degrees, or +45 degrees for example, while the monitor may be tilted downward by +5 degrees, +7 degrees, +10 degrees, +15 degrees or +20 degrees, for example. The seat back 510 may be configured with an anterior angle in the range of about 100 degrees to about 130 degrees, about 110 degrees to about 125 degrees, about 110 degrees to about 120 degrees, or about 120 degrees to about 130 degrees. The pedal angle 516 in the reclined configuration may be in the range of about 10 to 40 degrees, about 10 to 25 degrees, or about 10 to about 20 degrees, from the anterior horizontal plane. In other examples, the pedal angle 516 may be unchanged from the seated configuration. In some variations, due to spatial limitations or adjustment limitations of the user console 500, one or more changes in the seat configuration may also involve a translational motion. For example, the reclined configuration, to perform the retroversion of the seat pan 506, the seat controller may be configured to perform a combination of translational and pivot motions of the display 502, pedal assembly 504, seat pan 506, and seat back 510. In FIG. 5C, the seat assembly 518 may be moved lower, and then the front lip 520 of the seat pan 506 is pivotably raised to achieve the final retroversion of the seat pan 506. The pedal assembly 504 may be moved anteriorly and raised upward. Because of the posterior displacement of the user as from the seat pan 506 retroversion and the backward angulation of the seat back 510, the display 502 may be moved posteriorly and angled downward.

In some variations, the adjustments between the seated configuration and a reclined configuration may maintain the relative position and orientation of the display 502, pedal assembly 503, seat pan 506 and seat back 510, and utilize a combination of translation and angle changes within the mechanical adjustability ranges of the user console 500 to achieve a net rotation of the relative configuration of these components in space or with respect to gravity. The virtual axis of rotation of the relative configuration may be fixed throughout the reclining range, or may shift in different subranges of reclining. For example, one part of the reclining range may include a virtual axis of rotation generally located at the intersection of the seat pan 506 and seat back 510, while another part of the reclining range may have a virtual axis of rotation located at or about the pedal assembly, and/or at the base of the display assembly. In some variations, as the degree of reclining increases, the virtual or effective axis of rotation of the seat components may continuously shift from a posterior location to an anterior location, as a result of the limitations to the adjustability of the individual components. To control the degree of reclining, the user console 200 may have a single recline control, which coordinates the translational and angular movements of the display 502, pedal assembly 503, seat pan 506 and seat back 510 to achieve the desired recline level while maintaining the desired relative configuration.

Figure 27C:
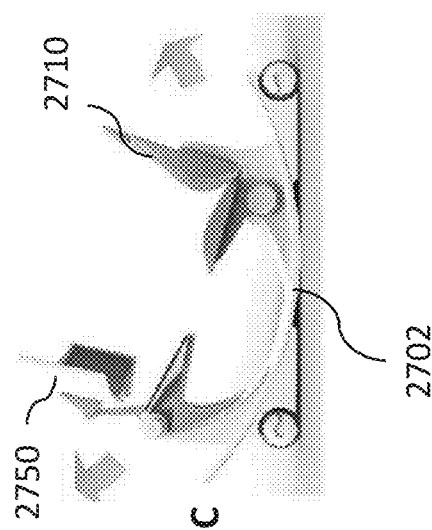
FIG. 27C is a schematic illustration of relative movements of a display and a seat assembly with respect to the curved base shown in FIG. 27A.
Figure 27B:
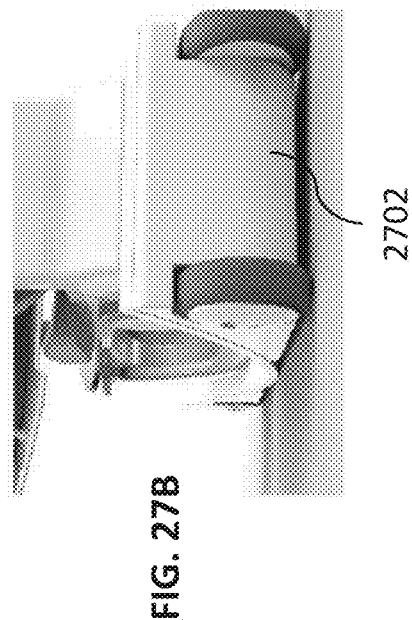
FIG. 27B is a detailed view of wheels on the curved base shown in FIG. 27A.

In another example of a user console, depicted in FIGS. 27A-27C, the user console comprises a curved base 2702 on which the display assembly 2750 and seat assembly 2710 are mounted, such as on rails. The display assembly 2750 and/or seat assembly 2710 may translate along the curved base 2702 to allow changes in the recline angle while simultaneously maintaining or altering the relative spacing and orientation of the display assembly 2750 and seat assembly 2710, as well as any foot-operated control such as a pedal assembly (not shown) that is coupled to the curved base 2750.

Figure 7A:
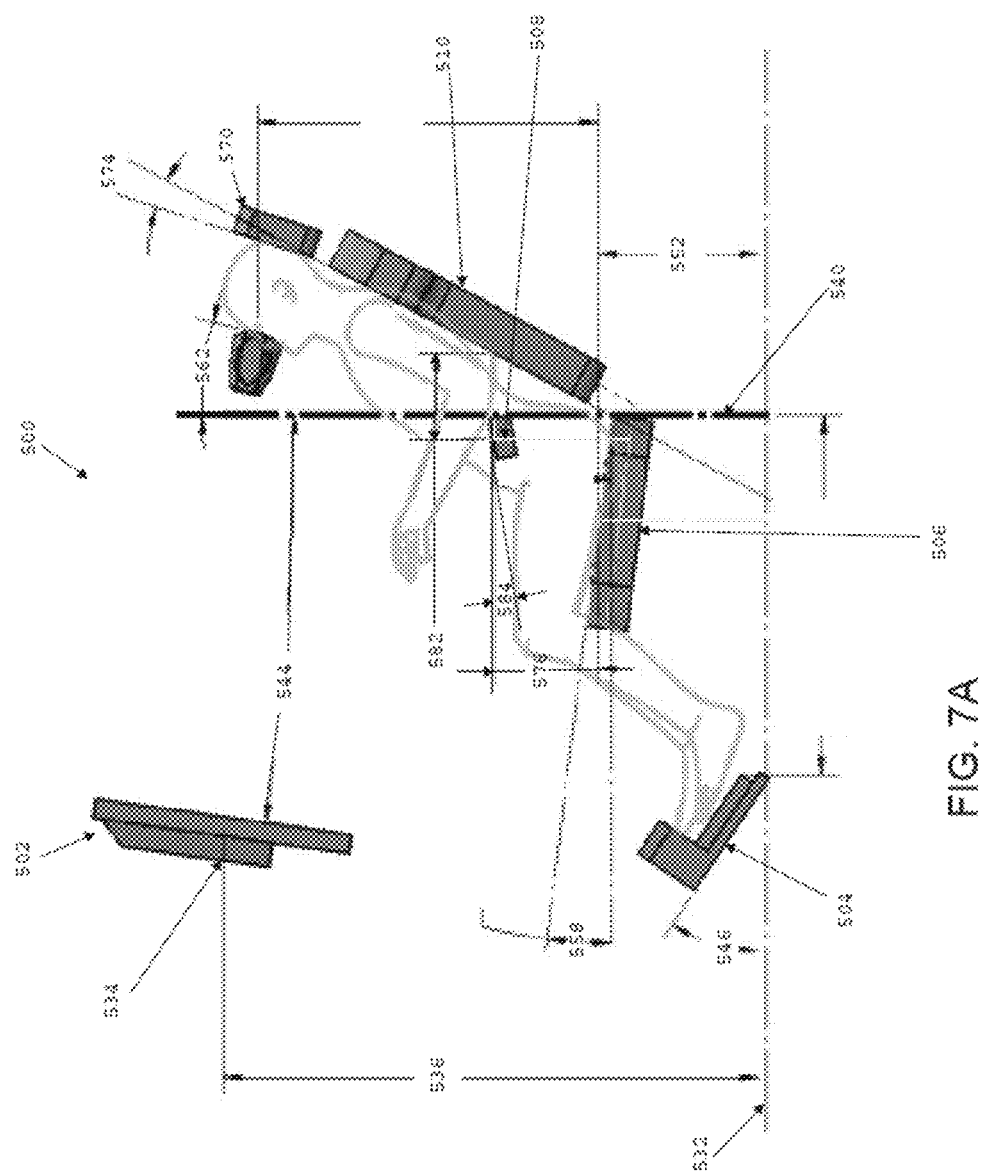
FIGS. 7A and 7B are schematic side and superior orthogonal representations of a reclined workstation configuration, respectively.

FIGS. 6 and 7A depict exemplary adjustable settings or parameters for a configuration of the user console. As shown in FIG. 6, the maximum adjustable height 530 from the base 532 to the midpoint or nominal mounting position 534 of the display panel(s) or display shell may be in the range of 150 cm to 160 cm, 155 cm to 180 cm, or 145 cm to 200 cm. In FIG. 7A, the minimum adjustable height 536 from the base 532 to the nominal mounting position 534 may be in the range of about 90 cm to 110 cm, about 95 cm to 105 cm, about 80 cm to 110 cm, or about 70 cm to about 100 cm.

The horizontal separation distance 538 between the mounting position 534 of the display and the vertical axis 540 intersecting the bottom of the seat back may have a minimum distance in the range of about 50 cm to 60 cm, about 45 cm to 65 cm, about 40 cm to 60 cm, and a maximum distance in the range of about 100 cm to about 110 cm, about 90 cm to about 120 cm, about 100 cm to about 150 cm, for example. The maximum upward tilt angle 542 of the display from the vertical axis, as depicted in FIG. 6, may be in the range of about 10 degrees to 20 degrees, about 10 degrees to about 30 degrees, or about 15 degrees to about 45 degrees. The minimum downward tilt angle 544 of the display 502, as illustrated in FIG. 7A, may be in the range of about 10 degrees to 20 degrees, about 10 degrees to about 30 degrees, or about 15 degrees to about 45 degrees. The total adjustable range of tilt for the display may be in the range of about 20 degrees to 40 degrees, about 20 degrees to about 60 degrees, or about 30 degrees about 90 degrees.

The maximum rearward tilt 546 of the pedal assembly 504 from the base 532 may be in the range of about 20 degrees to 40 degrees, about 25 degrees to 45 degrees, or about 30 degrees to 50 degrees. The minimum rearward tilt may be a zero degree or horizontal orientation parallel to the base 532, as shown in FIG. 7A, but in other variations, the minimum rearward tilt may be a non-zero angle that is less than about 7 degrees, less than about 5 degrees, or less than about 3 degrees. In other variations, the base may comprise a cavity or recess which may permit the pedal assembly to tilt anteriorly, below the surface of the base, within a range that may go down to about −5 degrees, about −10 degrees, or about −15 degrees below the base.

To accommodate different seating configurations, the pedal assembly 504 may be configured to be movably positioned along an anterior-posterior movement axis. Relative to the vertical axis 540 intersecting the anterior of the seat back 510, the minimum horizontal separation distance 548 to the rear edge of the pedal assembly 504 may be in the range of about 45 cm to 50 cm, about 40 cm to 55 cm, or about 35 cm to about 55 cm. The maximum horizontal separation distance 550 between the vertical axis 540 and the pedal assembly 504 may be in the range of about 90 cm to 95 cm, about 85 cm to 110 cm, or about 80 cm to 120 cm.

The seat pan 506 may be configured with a minimum seat height 552, as measured from the base 532 to the top center surface of the seat pan 506, which is in the range of about 25 cm to 35 cm, about 30 cm to about 50 cm, or about 20 cm to 60 cm. The maximum seat height 554 may be in the range of about 60 cm to 80 cm, about 65 cm to 100 cm, or about 50 cm to about 120 cm. The maximum anteversion angle 556 from the horizontal plane, as illustrated in FIG. 6, may be in the range of about 10 degrees to 20 degrees, about 15 degrees to 35 degrees, or about 15 degrees to 30 degrees. The typical retroversion angle in the reclined configuration may be about 5 degrees to 10 degrees, as illustrated in FIG. 7A, but the maximum retroversion angle 558 may be in the range of about 10 degrees to 20 degrees, about 15 degrees to 35 degrees, or about 15 degrees to 30 degrees. The total range of seat pan 506 angle adjustability may be in the range of about 20 degrees, to 40 degrees, about 30 degrees to about 50 degrees, about 25 degrees to about 45 degrees.

The seat back 510 may be typically in a retroverted position from the vertical axis 540 of about −10 degrees, as shown in FIG. 6, but may have a maximum anterior angle 560 that is at 0 degrees from the vertical axis 540, or may be configured with a maximum anterior angle of at least +5 degrees, +7 degrees or even +10 degrees. As illustrated in FIG. 7A, the maximum retroversion angle 562 from the vertical axis 540 may be in the range of about 20 degrees to 40 degrees, about 30 degrees to 60 degrees, or about 25 to degrees to 50 degrees.

In the seated and reclined configurations, the seat pan 506 and the seat back 510 may be in a relative relationship wherein the rear portion of the seat pan 506 and the bottom portion of the seat back 510 are in contact or otherwise in their closest proximity to each other, as depicted in FIG. 7A. In the elevated configuration, as depicted in FIG. 6, the rear portion of the seat pan 506 is displaced posteriorly relative to the bottom portion of the seat pan 510 (or alternatively, the bottom portion of the seat back 510 is displaced anteriorly relative to the rear portion or top surface of the seat pan 506). The maximum posterior displacement 564 of the seat pan 510 may be in the range of about 10 cm to 20 cm, about 15 cm to 30 cm, about 20 cm to 30 cm, or about 15 cm to about 40 cm or more.

Figure 7B:
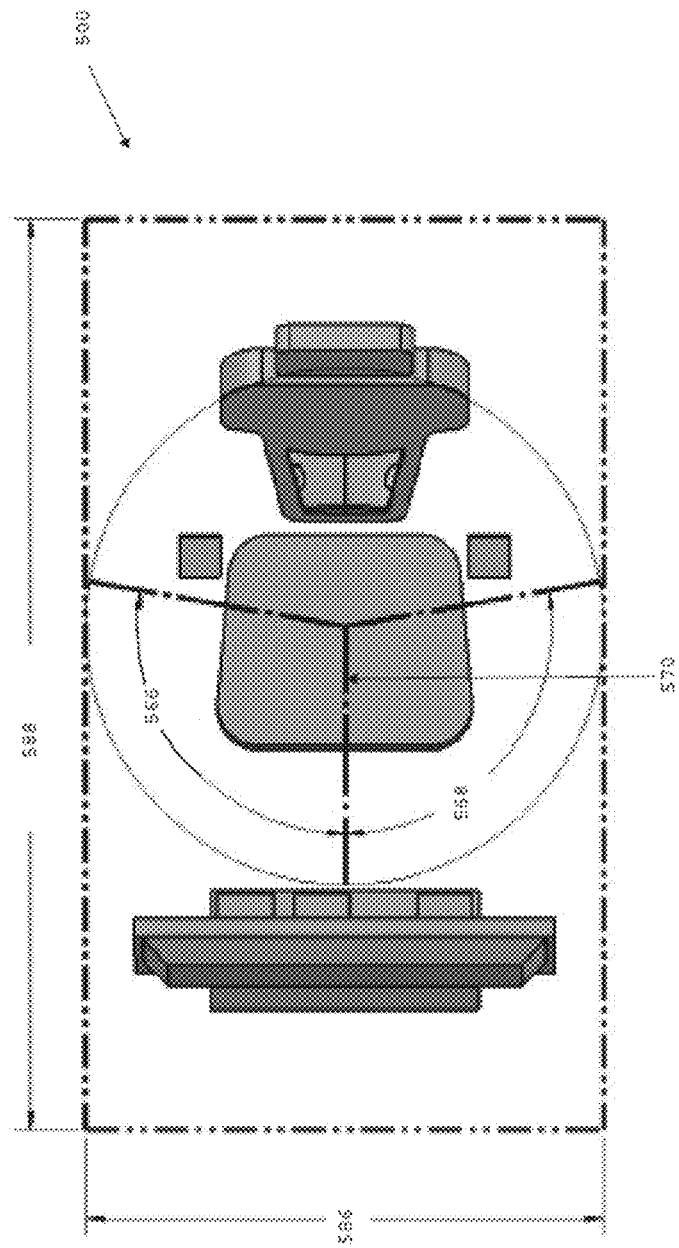

Depending on the configuration of the seat assembly, the seat pan 506 and seat back 510 may be configured to rotate laterally. In some examples, this rotation may facilitate entry and exit of the user from the seat assembly. As shown in FIG. 7B, the amount of maximum lateral rotation 566, 568 as measured from the anterior-posterior axis 570, may be in the range of about 45 degrees to 75 degrees, about 75 degrees to 120 degrees, about 90 degrees to about 140 degrees, or about 100 degrees to about 150 degrees. Although with many user consoles, the amount of maximum lateral rotation 566, 568 will be symmetrical to each side, in other examples, including but not limited to the asymmetric user consoles described below, the mount may be asymmetric, and smaller or not available, on the side with the asymmetric support.

Referring back to FIGS. 6 and 7A, the headrest 570 of the seat assembly, if any, is typically attached to the seat back 510 in either a fixed configuration or an adjustable configuration, but in other examples, may be independently movable of the seat back. When attached to the seat back 510 as in FIGS. 6 and 7A, the headrest 570 will move in conjunction with movements of the seat back 510, but may be configured for additional relative movement relative to the seat back 510. For example, the headrest in FIGS. 6 and 7A is configured to be vertically extendible from the seat back 510, with a minimum distance of zero and a maximum extension distance 572 that is in the range of about 10 cm to 40 cm, about 15 cm to 50 cm, about 20 cm to about 60 cm, or more. Relative to the longitudinal axis of the seat back 510, the headrest 570 may be configured with a maximum rearward tilt angle of zero, but in some variations, may be configured to with maximum rearward tilt angle in the range of about zero to −5 degrees, about zero to −10 degrees, about zero to −15 degrees, or about zero to −30 degrees. The maximum forward tilt angle 574 may be in the range of about zero to 30 degrees, about 10 degrees to 30 degrees, about 15 degrees to about 45 degrees, for example.

The armrest 508 of the seat assembly may be attached to seat pan 506 or seat back 510, and move with the adjustments to those structures, but may also be attached to a different structure of the user console 500, such as the seat shell (not shown) or the base 532, or display mount. In examples, where the armrest 508 moves with the seat pan 506 or the seat shell, the armrest 508 may have a vertical adjustable range with a minimum vertical distance 576 from the horizontal plane through the top center of the seat pan 506 that is in the range of about 15 cm to 25 cm, about 20 cm to 25 cm, about 15 to 50 cm, or about 20 cm to 60 cm or more. The maximum vertical distance 578 may be in the range of about 30 cm to 50 cm, about 40 cm to about 70 cm, about 35 cm to about 80 cm, for example. The armrest 508 may have a horizontal adjustable range with a minimum horizontal distance 580, from an anterior surface of the seat back 510 to the horizontal center of the armrest 508, in the range of about 10 cm to 30 cm, about 15 cm to 25 cm, about 15 to 50 cm, or about 20 cm to 60 cm or more. The maximum horizontal distance 582 may be in the range of about 30 cm to 50 cm, about 40 cm to about 70 cm, about 35 cm to about 80 cm, for example. In further examples, the armrest 508 may also be configured to rotate or tilt in the anterior-posterior direction, with a maximum anterior or forward angle 584 of about 10 degrees to 20 degrees, about 15 degrees to 30 degrees, or about 15 degrees to 45 degrees. The maximum posterior or rearward angle may be zero, or in the range of about zero to 10 degrees, about zero 15 degrees, about 5 degrees to 30 degrees, or about 10 degrees to about 45 degrees.

Referring back to FIG. 7B, the user console 500 has a width 586 that is in the range of about 90 cm to 100 cm, about 80 cm to about 120 cm, or about 90 cm to about 150 cm, or more. The length 588 may be in the range of about 150 cm to 200 cm, about 160 cm to about 250 cm, or about 160 cm to about 180 cm. The size of the user console may facilitate positioning of the user console 500 in a surgical or procedure suite, or through the door(s) of such a suite or room.

The above-described settings for seated, reclined, and elevated configurations of the user console may be further illustrated with reference to FIGS. 9-11. The seat assembly of the user console 900 in FIGS. 9A-9E is in a seated configuration. When the seat assembly is moved to an elevated configuration, as depicted in FIGS. 11A-11E, the seat shell 916 moves superiorly and posteriorly up the posteriorly angled seat support. Where compensation for these adjustments is desired, the display monitor support 906 may, for example, move posteriorly relative to the base, and the display monitor 950 may move superiorly relative to the display support 906. The pedal assembly 904 may also move posteriorly and may tilt downward to a more level/horizontal orientation, to better ergonomically orient to the user's near-vertical or elevated pose. The seat pan is retracted relative to the seat shell and the seat back, and may pivot to a more anteverted orientation. The headrest cushion may also move superiorly up the seat back, and the armrests are moved to a superior location relative to the seat assembly. The support arm of the immersive display may also be moved superiorly relative to the seat assembly, such as by actuated or manually-posed articulated adjustments of the linkages along the immersive display support arm.

FIGS. 10A-10E depict the user console 900 in the reclined configuration. Here, the seat shell 916 has been moved inferiorly and anteriorly down the posteriorly angled seat support 914, with a substantial portion of the seat support above the opening of the seat shell 916. The seat pan is in a retroverted position and the seat back has been tilted posteriorly with the seat back, such that the seat support is substantially residing in the seat back cavity. The headrest cushion may be moved inferiorly, toward the seat back cushion. The armrests have been tilted posteriorly with the seat back. Because of the retroversion of the seat pan, the user may be seated more deeply and lower in the seat shell and relative to the seat back, as compared to in the seated configuration of the seat assembly. In some variations, the support arm of the immersive display 960 may generally maintain an orientation parallel to the base of the user console (e.g., horizontal and parallel to the ground, if the base is horizontal). In some variations, the immersive display 960 may tilt downwards to, for example, maintain an orthogonal optical viewing axis for the user viewing the immersive display 960. Alternatively, in some variations, the proximal portion of the support arm of the immersive display 960 (e.g., the portion coupled to the seat back) may be moved to a lower position such that the support arm tilts posteriorly similar to the arm rests. In this user console the display 940 may or may not be configured to tilt downward to maintain a more orthogonal viewing plane with the user's optical axis. The display support may be moved more posteriorly to maintain or other partially compensate for any change in distance along the user's optical axis resulting from the reclining angle of the seat back. In other examples, anterior displacement of the seat shell down the seat support, and posterior movement of the seat back, are not performed, such as if the anterior displacement of the seat shell down the seat support is sufficient to maintain the desired viewing distance. Where the display support is moved posteriorly, the display support may be configured with a central opening between the lateral support legs, to accommodate the pedal assembly. The pedal assembly may be tilted backward to accommodate the user's recline angle in the seat assembly.

Safety Features

The user console may be further equipped with a "lock out" feature, in which the user console can automatically determine whether a user is in the user console and ready to perform a surgical procedure via the user console. In response to this determination the user console can automatically enable or disable the controls. The user console may include one or more sensors configured to detect the presence or absence of a user in the seat assembly. For example, such a sensor may be disposed in and/or around the seat assembly (e.g., in the seat pan, seat back, head rest, etc.) and include a pressure sensor configured to measure weight in the seat assembly, where a pressure measurement beyond a threshold value indicates presence of a user in the user console. As another example, an IR sensor may be configured to measure heat applied to the seat assembly, where a temperature measurement beyond a threshold value indicates presence a user in the user console. As another example, an optical sensor may be configured to detect an interruption or break in a light beam aimed across the user console, where interruption of the beam indicates presence of a user in the user console. Another example of such sensors is an optical sensor (e.g., in the display monitor, auxiliary display, immersive display, etc.) configured to apply an eye tracking algorithm to determine presence of a user ready to operate the controls of the user console. Furthermore, in some variations, presence of a user in the seating assembly may be determined by receiving a voice command (e.g., by an authorized user), performing voice or facial recognition, receiving approved user login identification, etc.

Certain user manipulations of the user console may also indicate the user's presence. For example, as shown in FIGS. 26A-26C, the user console may have a side entry configuration, in which a user may approach an outward facing, swiveling seat assembly (FIG. 26A) to enter the user console. The user may then swivel the seat assembly to a centered orientation (FIG. 26B) facing the front of the user console. In this example, the seat assembly may be equipped with a switch or other sensor configured to detect when the seat assembly rotates and transitions to the centered orientation, whereupon the controls for remotely operating the surgical instrument may be enabled. Other deliberate user actions (e.g., grasping user interface devices, engaging the pedal assembly, pressing a start button, etc.) may also trigger enablement of the controls. Conversely, opposite actions (swiveling the seat assembly outward, putting down the user interface devices, etc.) may trigger disablement of the controls.

The user console may additionally or alternatively include one or more sensors configured to detect the competency of a user in the seat assembly, such as to check that the user operating the surgical instrument is sufficiently well-rested and/or sober. For example, an optical sensor for performing eye tracking as described above may be used to predict whether a user is sleep-deprived or fatigued (e.g., based on eye movement, blink rate, etc.). As another example, pressure sensors such as those described above may be used to detect sudden shifts or rapid changes in weight distribution in the seat assembly, which may indicate a medical emergency such as a user's seizure. Furthermore, a chemical sensor (e.g., breathalyzer) may be included to check for sobriety based on ethanol traces and the like. These kinds of events may, for example, trigger at least an audible/visible alarm or other warning, and/or a disablement of the controls in order to protect the patient undergoing a surgical procedure.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

The invention claimed is:

1. A user console for controlling a remote surgical robotic instrument comprising:
   an adjustable ergonomic seat assembly comprising a seat pan, wherein the seat assembly is configurable between a seated configuration and an elevated configuration, wherein the seat pan has a higher anteverted position in the elevated configuration than in the seated configuration;
   a display configured to receive real time surgical information; and
   one or more controls for remotely controlling the robotic instrument;
   wherein the display or the one or more controls has multiple positions and changes position automatically according to a seating profile associated with at least one user.

2. The user console of claim 1, wherein the display or the one or more controls is in a higher position when the seat assembly is in the elevated configuration than when the seat assembly is in the seated configuration.

3. The user console of claim 1, wherein the seat assembly further comprises a seat back having multiple angular positions relative to the seat pan.

4. The user console of claim 3, wherein a posterior end of the seat pan is more posterior than a lower end of the seat back when the seat assembly is in the elevated configuration than when the seat assembly is in the seated configuration.

5. The user console of claim 4, further comprising a headrest coupled to the seat back.

6. The user console of claim 1, wherein the seat assembly is further configurable in a reclined configuration.

7. The user console of claim 1, wherein the display or the one or more controls changes position automatically according to any one of a plurality of seating profiles associated with a plurality of users.

8. The user console of claim 1, wherein the one or more controls comprise a handheld user interface device.

9. The user console of claim 8, further comprising a docking station configured to releasably hold the handheld user interface device.

10. The user console of claim 1, wherein the one or more controls comprises a foot-operated control.

11. The user console of claim 10, wherein the one or more controls comprise a foot pedal assembly.

12. The user console of claim 11, wherein the foot pedal assembly is configured to adjustably tilt posteriorly.

13. The user console of claim 10, further comprising a base, wherein the pedal assembly and the seat assembly are mounted on the base.

14. The user console of claim 13, wherein the pedal assembly is configured to translate along the base.

15. The user console of claim 1, further comprising at least one armrest coupled to the seat assembly.

16. The user console of claim 15, wherein the armrest has multiple positions and changes position automatically according to the seating profile.

17. The user console of claim 15, wherein the armrest is in a more superior position relative to the seat pan when the seat assembly is in the elevated configuration than when the seat assembly is in the seated configuration.

18. The user console of claim 1, further comprising a control panel for receiving user information.

19. The user console of claim 1, wherein the display comprises an open display.

20. The user console of claim 1, wherein the display comprises an immersive display.

21. The user console of claim 1, wherein the display or the one or more controls changes position automatically according to a surgical procedure type.

22. The user console of claim 1, wherein the position of the display or the one or more controls is manually adjustable.

23. The user console of claim 1, further comprising a console controller configured to detect the presence or absence of a user in the user console.

24. The user console of claim 23, wherein the console controller detects the presence or absence of a user based on an eye-tracking algorithm.

25. The user console of claim 23, wherein the console controller detects the presence or absence of a user based on at least one sensor in the user console.

26. The user console of claim 25, wherein the console controller detects the presence or absence of a user based on at least one pressure sensor in the user console.

27. The user console of claim 23, wherein the one or more controls is disabled in response to the console controller detecting the absence of a user.

28. The user console of claim 1, further comprising wheels coupled to the seat assembly.

29. The user console of claim 1, wherein at least one of the seat assembly and the one or more controls provides haptic feedback to a user in the user console.

* * * * *